US008143007B2

(12) United States Patent
Devinder et al.

(10) Patent No.: US 8,143,007 B2
(45) Date of Patent: Mar. 27, 2012

(54) NESTED PRIMER SETS FOR AMPLIFYING MOUSE IMMUNOGLOBULIN VARIABLE GENE SEGMENTS

(75) Inventors: Sehgal Devinder, New Delhi (IN); Rohatgi Soma, New Delhi (IN)

(73) Assignee: National Institute of Immunology, New Delhi (IN)

( * ) Notice: Subject to any disclaimer, the term of this patent is extended or adjusted under 35 U.S.C. 154(b) by 328 days.

(21) Appl. No.: 12/381,679

(22) Filed: Mar. 13, 2009

(65) Prior Publication Data
US 2009/0280489 A1 Nov. 12, 2009

(30) Foreign Application Priority Data

Mar. 13, 2008 (IN) .............................. 634/DEL/2008

(51) Int. Cl.
C12Q 1/68 (2006.01)
C12P 19/34 (2006.01)
C07H 21/04 (2006.01)
(52) U.S. Cl. ..................... 435/6.12; 435/91.2; 536/24.33
(58) Field of Classification Search ............. 435/6, 91.2; 536/24.33
See application file for complete search history.

(56) References Cited

U.S. PATENT DOCUMENTS 5,830,663 A * 11/1998 Embleton et al. .................. 435/6
6,258,529 B1 * 7/2001 Berdoz et al. ...................... 435/6

OTHER PUBLICATIONS

Brezinschek, H. P., et al., "Analysis of the Heavy Chain Repertoire of Human Peripheral B Cells Using Single-Cell Polymerase Chain Reaction", *The Journal of Immunology*, 155, (1995) , 190-202.
Chardès, T., et al., "Efficient amplification and direct sequencing of mouse variable regions from any immunoglobulin gene family", *FEBS Letters*, 452, (1999), 386-394.
Chiang, Y. L., et al., "Direct cDNA Cloning of the Rearranged Immunoglobulin Variable Region", *BioTechniques*, 7(4), (1989), 360-366.
Coloma, M. J., et al., "Primer Design for the Cloning of Immunoglobulin Heavy-Chain Leader-Variable Regions from Mouse Hybridoma Cells Using the PCR", *BioTechniques*, 11(2), (1991), 152-154.
Dattamajumdar, A. K., et al., "Rapid cloning of any rearranged mouse immunoglobulin variable genes", *Immunogenetics*, 43(3), (1996), 141-151.
Dohmen, S. E., et al., "Production of recombinant Ig molecules from antigen-selected single B cells and restricted usage of Ig-gene segments by anti-D antibodies", *Journal of Immunological Methods*, 298, (2005), 9-20.
Essono, S., et al., "A general method allowing the design of oligonucleotide primers to amplify the variable regions from immunoglobulin cDNA", *Journal of Immunological Methods*, 279, (2003), 251-266.

Farner, N. L., et al., "Molecular Mechanisms and Selection Influence the Generation of the Human Vλjλ Repertoire", *The Journal of Immunology*, 162, (1999), 2137-2145.
Foster, S. J., et al., "Molecular Mechanisms and Selective Influences That Shape the Kappa Gene Repertoire of IgM+ B Cells", *J. Clin. Invest.*, 99(7), (1997), 1614-1627.
Guo, L., et al., "IgM-mediated signaling is required for the development of a normal B cell memory response", *Molecular Immunology*, 45(4), (2008), 1071-1077.
Jacob, J., et al., "In Situ Studies of the Primary Immune Response to (4-hydroxy-3-nitrophenyl)acetyl. I. The Architecture and Dynamics of Responding Cell Populations", *J. Exp. Med.*, 173(5), 1991 , 1165-1175.
Jacob, J., et al., "Intraclonal generation of antibody mutants in germinal centres", *Nature*, 354(6352), (1991), 389-392.
Jones, S. T., et al., "Materials and Methods—Rapid PCR-Cloning of Full-Length Mouse Immunoglobulin Variable Regions", *Bio/Technology*, 9, (Jan. 1991), 88-89.
Kettleborough, C. A., et al., "Optimization of primers for cloning libraries of mouse immunoglobulin genes using the polymerase chain reaction", *Eur. J. Immunol.*, 23(1), (1993), 206-211.
Kim, H. J., et al., "Chapter 3—Single Cell Analysis of Synovial Tissue B-Cells", *Methods in Molecular Medicine*, vol. 136: Arthritis Research, vol. 2, (2007), 25-37.
Krebber, A., et al., "Reliable cloning of functional antibody variable domains from hybridomas and spleen cell repertoires employing a reengineered phage display system", *Journal of Immunological Methods*, 201, (1997), 35-55.
Lan, F., et al., "Extended fitness of variable region primers by a novel PCR protocol", *Journal of Immunological Methods*, 195, (1996), 27-32.
Larrick, J. W., et al., "Immunoglobulin V Regions of a Bactericidal Anti-*Neisseria meningitidis* Outer Membrane Protein Monoclonal Antibody", *Scand. J. Immunol.*, 32, (1990), 121-128.
Lebœuf, R. D., et al., "Cloning and sequencing of immunoglobulin variable-region genes using degenerate oligodeoxyribonucleotides and polymerase chain reaction", *Gene*, 82(2),(1989), 371-377.
Nicholls, P. J., et al., "An improved method for generating single-chain antibodies from hybridomas", *Journal of Immunological Methods*, 165, (1993) , 81-91.
Orlandi, R., et al., "Cloning Immunoglobulin Variable Domains for Expression by the Polymerase Chain Reaction", *Proc. Natl. Acad. Sci. USA*, 86, (1989), 3833-3837.
Owens, R. J., et al., "The genetic engineering of monoclonal antibodies", *Journal of Immunological Methods*, 168, (1994), 149-165.
Ruberti, F., et al., "The use of the RACE method to clone hybridoma cDNA when V region primers fail", *Journal of Immunological Methods*, 173, (1994), 33-39.

(Continued)

Primary Examiner — Kenneth R. Horlick
(74) Attorney, Agent, or Firm — Schwegman, Lundberg & Woessner, P.A.

(57) ABSTRACT

The present invention provides oligonucleotides for detection of rearrangement of immunoglobulin genes for identifying clonality of cells, cancer cells, hypermutation in immunoglobulin gene, antibody isotype producing cell and/or assaying B cell repertoire in a sample. The oligonucleotides disclosed in the present invention are very specific to the immunoglobulin genes.

8 Claims, 5 Drawing Sheets

OTHER PUBLICATIONS

Sehgal, D., et al., "Analyses of Single B Cells by Polymerase Chain Reaction Reveal Rearranged V (sub H) with Germline Sequences in Spleens of Immunized Adult Rabbits: Implications for B Cell Repertoire Maintenance and Renewal", *The Journal of Immunology*, 161, (1998), 5347-5356.

Seijen, A. M., et al., "Systematic design of mouse Vh gene family-specific Oligonucleotides", *Journal of Immunological Methods*, 254, (2001), 161-168.

Tiller, T., et al., "Efficient generation of monoclonal antibodies from single human B cells by single cell RT-PCR and expression vector cloning", *Journal of Immunological Methods*, (2007), 13 pgs.

Wang, X., et al., "Human immunoglobulin variable gene analysis by single cell RT-PCR", *Journal of Immunological Methods*, 244, (2000), 217-225.

Wang, Y., et al., "Degenerated primer design to amplify the heavy chain variable region from immunoglobulin cDNA", *BMC Bioinformatics*, 7(Suppl. 4), 7 pgs, (2006).

Wang, Z., et al., "Universal PCR amplication of mouse immunoglobulin gene variable regions: the design of degenerate primers and an assessment of the effect of DNA polymerase 3' to 5' exonuclease activity", *Journal of Immunological Methods*, 233, (2000), 167-177.

Zhou, H., et al., "Optimization of primer sequences for mouse scFv repertoire display library construction", *Nucleic Acids Research*, 22(5), (1994), 888-889.

* cited by examiner

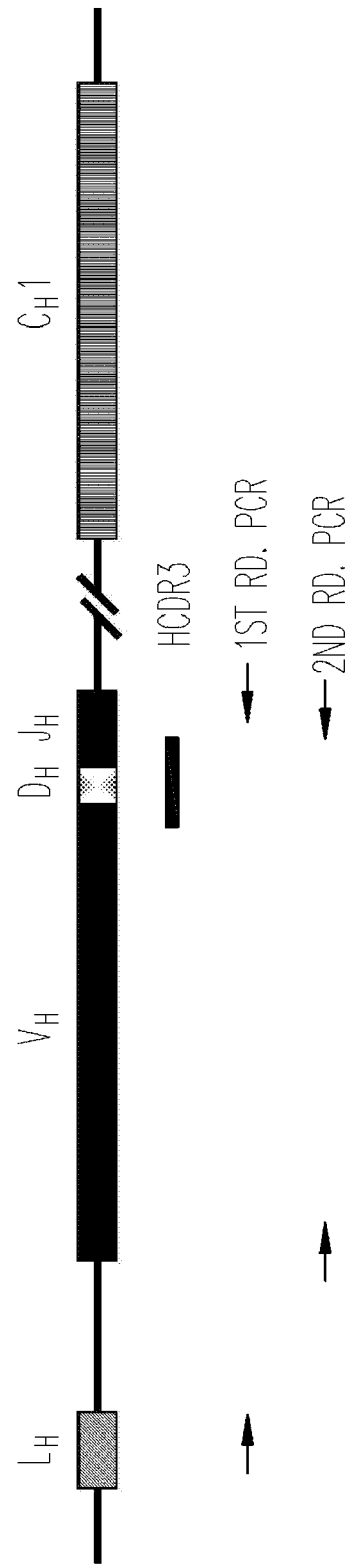
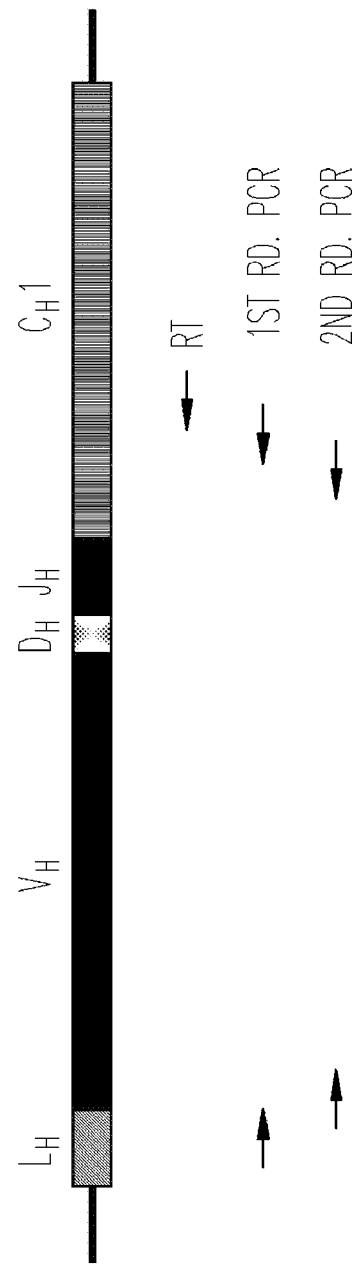
Fig. 1A
Fig. 1B

SEQUENCE LISTING

<160> NUMBER OF SEQ ID NOS: 112

<210> SEQ ID NO 1
<211> LENGTH: 20
<212> TYPE: DNA
<213> ORGANISM: ARTIFICIAL SEQUENCE

```
<220> FEATURE:
<223> OTHER INFORMATION: SYNTHETIC PRIMER

<400> SEQUENCE: 1
agrtycagct gcarcagtct                                         20

<210> SEQ ID NO 2
<211> LENGTH: 19
<212> TYPE: DNA
<213> ORGANISM: ARTIFICIAL SEQUENCE
<220> FEATURE:
<223> OTHER INFORMATION: SYNTHETIC PRIMER

<400> SEQUENCE: 2
aggtccaact gcagcagcc                                          19

<210> SEQ ID NO 3
<211> LENGTH: 21
<212> TYPE: DNA
<213> ORGANISM: ARTIFICIAL SEQUENCE
<220> FEATURE:
<223> OTHER INFORMATION: SYNTHETIC PRIMER

<400> SEQUENCE: 3
gargatrtcc tgyaaggctt c                                       21

<210> SEQ ID NO 4
<211> LENGTH: 20
<212> TYPE: DNA
<213> ORGANISM: ARTIFICIAL SEQUENCE
<220> FEATURE:
<223> OTHER INFORMATION: SYNTHETIC PRIMER

<400> SEQUENCE: 4
argbtgtcct gcaagrcttc                                         20

<210> SEQ ID NO 5
<211> LENGTH: 20
<212> TYPE: DNA
<213> ORGANISM: ARTIFICIAL SEQUENCE
<220> FEATURE:
<223> OTHER INFORMATION: SYNTHETIC PRIMER

<400> SEQUENCE: 5
tctgcctggt gacwttccca                                         20

<210> SEQ ID NO 6
<211> LENGTH: 20
<212> TYPE: DNA
<213> ORGANISM: ARTIFICIAL SEQUENCE
<220> FEATURE:
<223> OTHER INFORMATION: SYNTHETIC PRIMER

<400> SEQUENCE: 6
tgcagctgaa gsagtcagga                                         20

<210> SEQ ID NO 7
<211> LENGTH: 19
<212> TYPE: DNA
<213> ORGANISM: ARTIFICIAL SEQUENCE
<220> FEATURE:
<223> OTHER INFORMATION: SYNTHETIC PRIMER

<400> SEQUENCE: 7
gtgcagcttc aggagtcag                                          19
```

<210> SEQ ID NO 8
<211> LENGTH: 20
<212> TYPE: DNA
<213> ORGANISM: ARTIFICIAL SEQUENCE
<220> FEATURE:
<223> OTHER INFORMATION: SYNTHETIC PRIMER

<400> SEQUENCE: 8
aaccttctca gwcactgtcc                                          20

<210> SEQ ID NO 9
<211> LENGTH: 20
<212> TYPE: DNA
<213> ORGANISM: ARTIFICIAL SEQUENCE
<220> FEATURE:
<223> OTHER INFORMATION: SYNTHETIC PRIMER

<400> SEQUENCE: 9
gaggtgaagc ttctcgagtc                                          20

<210> SEQ ID NO 10
<211> LENGTH: 18
<212> TYPE: DNA
<213> ORGANISM: ARTIFICIAL SEQUENCE
<220> FEATURE:
<223> OTHER INFORMATION: SYNTHETIC PRIMER

<400> SEQUENCE: 10
ggaggtggcc tggtgcag                                            18

<210> SEQ ID NO 11
<211> LENGTH: 20
<212> TYPE: DNA
<213> ORGANISM: ARTIFICIAL SEQUENCE
<220> FEATURE:
<223> OTHER INFORMATION: SYNTHETIC PRIMER

<400> SEQUENCE: 11
gaagtgaagc tggtggagtc                                          20

<210> SEQ ID NO 12
<211> LENGTH: 19
<212> TYPE: DNA
<213> ORGANISM: ARTIFICIAL SEQUENCE
<220> FEATURE:
<223> OTHER INFORMATION: SYNTHETIC PRIMER

<400> SEQUENCE: 12
agcctggagg gtccctgaa                                           19

<210> SEQ ID NO 13
<211> LENGTH: 21
<212> TYPE: DNA
<213> ORGANISM: ARTIFICIAL SEQUENCE
<220> FEATURE:
<223> OTHER INFORMATION: SYNTHETIC PRIMER

<400> SEQUENCE: 13
atgkacttgg gactgarctg t                                        21

<210> SEQ ID NO 14
<211> LENGTH: 20
<212> TYPE: DNA
<213> ORGANISM: ARTIFICIAL SEQUENCE
<220> FEATURE:
<223> OTHER INFORMATION: SYNTHETIC PRIMER

<400> SEQUENCE: 14
gaggagtctg gaggaggctt                                             20

<210> SEQ ID NO 15
<211> LENGTH: 20
<212> TYPE: DNA
<213> ORGANISM: ARTIFICIAL SEQUENCE
<220> FEATURE:
<223> OTHER INFORMATION: SYNTHETIC PRIMER

<400> SEQUENCE: 15
cagtgtgagg tgaagctggt                                             20

<210> SEQ ID NO 16
<211> LENGTH: 20
<212> TYPE: DNA
<213> ORGANISM: ARTIFICIAL SEQUENCE
<220> FEATURE:
<223> OTHER INFORMATION: SYNTHETIC PRIMER

<400> SEQUENCE: 16
tctggaggag gcttggtaca                                             20

<210> SEQ ID NO 17
<211> LENGTH: 21
<212> TYPE: DNA
<213> ORGANISM: ARTIFICIAL SEQUENCE
<220> FEATURE:
<223> OTHER INFORMATION: SYNTHETIC PRIMER

<400> SEQUENCE: 17
ccaggttact ctgaaagagt c                                           21

<210> SEQ ID NO 18
<211> LENGTH: 20
<212> TYPE: DNA
<213> ORGANISM: ARTIFICIAL SEQUENCE
<220> FEATURE:
<223> OTHER INFORMATION: SYNTHETIC PRIMER

<400> SEQUENCE: 18
ctgggatatt gcagccctcc                                             20

<210> SEQ ID NO 19
<211> LENGTH: 21
<212> TYPE: DNA
<213> ORGANISM: ARTIFICIAL SEQUENCE
<220> FEATURE:
<223> OTHER INFORMATION: SYNTHETIC PRIMER

<400> SEQUENCE: 19
tgtggacctt gctattcctg a                                           21

<210> SEQ ID NO 20
<211> LENGTH: 20
<212> TYPE: DNA
<213> ORGANISM: ARTIFICIAL SEQUENCE
<220> FEATURE:
<223> OTHER INFORMATION: SYNTHETIC PRIMER

<400> SEQUENCE: 20
acagatccag ttggtgcagt                                             20

<210> SEQ ID NO 21
<211> LENGTH: 21
<212> TYPE: DNA
<213> ORGANISM: ARTIFICIAL SEQUENCE

```
<220> FEATURE:
<223> OTHER INFORMATION: SYNTHETIC PRIMER

<400> SEQUENCE: 21
tgttggggct gaagtgggtt t                                          21

<210> SEQ ID NO 22
<211> LENGTH: 20
<212> TYPE: DNA
<213> ORGANISM: ARTIFICIAL SEQUENCE
<220> FEATURE:
<223> OTHER INFORMATION: SYNTHETIC PRIMER

<400> SEQUENCE: 22
aggtgtgcat tgtgaggtgc                                            20

<210> SEQ ID NO 23
<211> LENGTH: 21
<212> TYPE: DNA
<213> ORGANISM: ARTIFICIAL SEQUENCE
<220> FEATURE:
<223> OTHER INFORMATION: SYNTHETIC PRIMER

<400> SEQUENCE: 23
atggagtggg aactgagctt a                                          21

<210> SEQ ID NO 24
<211> LENGTH: 20
<212> TYPE: DNA
<213> ORGANISM: ARTIFICIAL SEQUENCE
<220> FEATURE:
<223> OTHER INFORMATION: SYNTHETIC PRIMER

<400> SEQUENCE: 24
gaagtgcagc tgttggagac                                            20

<210> SEQ ID NO 25
<211> LENGTH: 19
<212> TYPE: DNA
<213> ORGANISM: ARTIFICIAL SEQUENCE
<220> FEATURE:
<223> OTHER INFORMATION: SYNTHETIC PRIMER

<400> SEQUENCE: 25
agcttcagga gtcaggacc                                             19

<210> SEQ ID NO 26
<211> LENGTH: 19
<212> TYPE: DNA
<213> ORGANISM: ARTIFICIAL SEQUENCE
<220> FEATURE:
<223> OTHER INFORMATION: SYNTHETIC PRIMER

<400> SEQUENCE: 26
cctggtgaaa ccctcacag                                             19

<210> SEQ ID NO 27
<211> LENGTH: 20
<212> TYPE: DNA
<213> ORGANISM: ARTIFICIAL SEQUENCE
<220> FEATURE:
<223> OTHER INFORMATION: SYNTHETIC PRIMER

<400> SEQUENCE: 27
caggtgcagc ttgtagagac                                            20
```

-continued

```
<210> SEQ ID NO 28
<211> LENGTH: 19
<212> TYPE: DNA
<213> ORGANISM: ARTIFICIAL SEQUENCE
<220> FEATURE:
<223> OTHER INFORMATION: SYNTHETIC PRIMER

<400> SEQUENCE: 28
aggcttggtg aggcctgga                                                 19

<210> SEQ ID NO 29
<211> LENGTH: 21
<212> TYPE: DNA
<213> ORGANISM: ARTIFICIAL SEQUENCE
<220> FEATURE:
<223> OTHER INFORMATION: SYNTHETIC PRIMER

<400> SEQUENCE: 29
atgcagctgg gtcatcttct t                                              21

<210> SEQ ID NO 30
<211> LENGTH: 19
<212> TYPE: DNA
<213> ORGANISM: ARTIFICIAL SEQUENCE
<220> FEATURE:
<223> OTHER INFORMATION: SYNTHETIC PRIMER

<400> SEQUENCE: 30
gaggttcagc tgcagcagt                                                 19

<210> SEQ ID NO 31
<211> LENGTH: 21
<212> TYPE: DNA
<213> ORGANISM: ARTIFICIAL SEQUENCE
<220> FEATURE:
<223> OTHER INFORMATION: SYNTHETIC PRIMER

<400> SEQUENCE: 31
gactggattt ggatcackct c                                              21

<210> SEQ ID NO 32
<211> LENGTH: 21
<212> TYPE: DNA
<213> ORGANISM: ARTIFICIAL SEQUENCE
<220> FEATURE:
<223> OTHER INFORMATION: SYNTHETIC PRIMER

<400> SEQUENCE: 32
caatcccagg ttcacctaca a                                              21

<210> SEQ ID NO 33
<211> LENGTH: 21
<212> TYPE: DNA
<213> ORGANISM: ARTIFICIAL SEQUENCE
<220> FEATURE:
<223> OTHER INFORMATION: SYNTHETIC PRIMER

<400> SEQUENCE: 33
tggagtttgg acttagttgg g                                              21

<210> SEQ ID NO 34
<211> LENGTH: 19
<212> TYPE: DNA
<213> ORGANISM: ARTIFICIAL SEQUENCE
<220> FEATURE:
<223> OTHER INFORMATION: SYNTHETIC PRIMER

<400> SEQUENCE: 34
```

```
gtgaggtgca gctggtgga                                        19

<210> SEQ ID NO 35
<211> LENGTH: 20
<212> TYPE: DNA
<213> ORGANISM: ARTIFICIAL SEQUENCE
<220> FEATURE:
<223> OTHER INFORMATION: SYNTHETIC PRIMER

<400> SEQUENCE: 35
ctyacctgag gagacdgtga                                       20

<210> SEQ ID NO 36
<211> LENGTH: 18
<212> TYPE: DNA
<213> ORGANISM: ARTIFICIAL SEQUENCE
<220> FEATURE:
<223> OTHER INFORMATION: SYNTHETIC PRIMER

<400> SEQUENCE: 36
gtggtccctg cgccccag                                         18

<210> SEQ ID NO 37
<211> LENGTH: 18
<212> TYPE: DNA
<213> ORGANISM: ARTIFICIAL SEQUENCE
<220> FEATURE:
<223> OTHER INFORMATION: SYNTHETIC PRIMER

<400> SEQUENCE: 37
ggtbccttgg ccccagta                                         18

<210> SEQ ID NO 38
<211> LENGTH: 17
<212> TYPE: DNA
<213> ORGANISM: ARTIFICIAL SEQUENCE
<220> FEATURE:
<223> OTHER INFORMATION: SYNTHETIC PRIMER

<400> SEQUENCE: 38
gatgacttca gtgttgt                                          17

<210> SEQ ID NO 39
<211> LENGTH: 16
<212> TYPE: DNA
<213> ORGANISM: ARTIFICIAL SEQUENCE
<220> FEATURE:
<223> OTHER INFORMATION: SYNTHETIC PRIMER

<400> SEQUENCE: 39
cagggatcca kagttc                                           16

<210> SEQ ID NO 40
<211> LENGTH: 16
<212> TYPE: DNA
<213> ORGANISM: ARTIFICIAL SEQUENCE
<220> FEATURE:
<223> OTHER INFORMATION: SYNTHETIC PRIMER

<400> SEQUENCE: 40
caggtcacat tcatcg                                           16

<210> SEQ ID NO 41
<211> LENGTH: 17
<212> TYPE: DNA
<213> ORGANISM: ARTIFICIAL SEQUENCE
```

```
<220> FEATURE:
<223> OTHER INFORMATION: SYNTHETIC PRIMER

<400> SEQUENCE: 41
cacagtgctc atgttca                                              17

<210> SEQ ID NO 42
<211> LENGTH: 16
<212> TYPE: DNA
<213> ORGANISM: ARTIFICIAL SEQUENCE
<220> FEATURE:
<223> OTHER INFORMATION: SYNTHETIC PRIMER

<400> SEQUENCE: 42
agtggctgac ttccaa                                               16

<210> SEQ ID NO 43
<211> LENGTH: 21
<212> TYPE: DNA
<213> ORGANISM: ARTIFICIAL SEQUENCE
<220> FEATURE:
<223> OTHER INFORMATION: SYNTHETIC PRIMER

<400> SEQUENCE: 43
catggccacc agattcttat c                                         21

<210> SEQ ID NO 44
<211> LENGTH: 21
<212> TYPE: DNA
<213> ORGANISM: ARTIFICIAL SEQUENCE
<220> FEATURE:
<223> OTHER INFORMATION: SYNTHETIC PRIMER

<400> SEQUENCE: 44
agacatttgg gaaggactga c                                         21

<210> SEQ ID NO 45
<211> LENGTH: 21
<212> TYPE: DNA
<213> ORGANISM: ARTIFICIAL SEQUENCE
<220> FEATURE:
<223> OTHER INFORMATION: SYNTHETIC PRIMER

<400> SEQUENCE: 45
agggaaatar cccttgacca g                                         21

<210> SEQ ID NO 46
<211> LENGTH: 21
<212> TYPE: DNA
<213> ORGANISM: ARTIFICIAL SEQUENCE
<220> FEATURE:
<223> OTHER INFORMATION: SYNTHETIC PRIMER

<400> SEQUENCE: 46
agggaagtag cctttgacaa g                                         21

<210> SEQ ID NO 47
<211> LENGTH: 20
<212> TYPE: DNA
<213> ORGANISM: ARTIFICIAL SEQUENCE
<220> FEATURE:
<223> OTHER INFORMATION: SYNTHETIC PRIMER

<400> SEQUENCE: 47
ggccagtgga tagachgatg                                           20
```

<210> SEQ ID NO 48
<211> LENGTH: 20
<212> TYPE: DNA
<213> ORGANISM: ARTIFICIAL SEQUENCE
<220> FEATURE:
<223> OTHER INFORMATION: SYNTHETIC PRIMER

<400> SEQUENCE: 48
cagggaccaa gggatagaca                                          20

<210> SEQ ID NO 49
<211> LENGTH: 22
<212> TYPE: DNA
<213> ORGANISM: ARTIFICIAL SEQUENCE
<220> FEATURE:
<223> OTHER INFORMATION: SYNTHETIC PRIMER

<400> SEQUENCE: 49
gaatcaggca gccgattatc ac                                       22

<210> SEQ ID NO 50
<211> LENGTH: 20
<212> TYPE: DNA
<213> ORGANISM: ARTIFICIAL SEQUENCE
<220> FEATURE:
<223> OTHER INFORMATION: SYNTHETIC PRIMER

<400> SEQUENCE: 50
tgggagtgtc agtgggtaga                                          20

<210> SEQ ID NO 51
<211> LENGTH: 21
<212> TYPE: DNA
<213> ORGANISM: ARTIFICIAL SEQUENCE
<220> FEATURE:
<223> OTHER INFORMATION: SYNTHETIC PRIMER

<400> SEQUENCE: 51
tcatggaagc agtgccttta c                                        21

<210> SEQ ID NO 52
<211> LENGTH: 21
<212> TYPE: DNA
<213> ORGANISM: ARTIFICIAL SEQUENCE
<220> FEATURE:
<223> OTHER INFORMATION: SYNTHETIC PRIMER

<400> SEQUENCE: 52
tagagctgag ggttcctgat a                                        21

<210> SEQ ID NO 53
<211> LENGTH: 20
<212> TYPE: DNA
<213> ORGANISM: ARTIFICIAL SEQUENCE
<220> FEATURE:
<223> OTHER INFORMATION: SYNTHETIC PRIMER

<400> SEQUENCE: 53
tctgagagga ggaacatgtc                                          20

<210> SEQ ID NO 54
<211> LENGTH: 21
<212> TYPE: DNA
<213> ORGANISM: ARTIFICIAL SEQUENCE
<220> FEATURE:
<223> OTHER INFORMATION: SYNTHETIC PRIMER

<400> SEQUENCE: 54
tcacctgcaa gacagatagt g                                              21

<210> SEQ ID NO 55
<211> LENGTH: 19
<212> TYPE: DNA
<213> ORGANISM: ARTIFICIAL SEQUENCE
<220> FEATURE:
<223> OTHER INFORMATION: SYNTHETIC PRIMER

<400> SEQUENCE: 55
tgatgaccca ractccact                                                 19

<210> SEQ ID NO 56
<211> LENGTH: 20
<212> TYPE: DNA
<213> ORGANISM: ARTIFICIAL SEQUENCE
<220> FEATURE:
<223> OTHER INFORMATION: SYNTHETIC PRIMER

<400> SEQUENCE: 56
cctgtcagtc ttggagatca                                                20

<210> SEQ ID NO 57
<211> LENGTH: 22
<212> TYPE: DNA
<213> ORGANISM: ARTIFICIAL SEQUENCE
<220> FEATURE:
<223> OTHER INFORMATION: SYNTHETIC PRIMER

<400> SEQUENCE: 57
tttgtcggtt accattggac aa                                             22

<210> SEQ ID NO 58
<211> LENGTH: 18
<212> TYPE: DNA
<213> ORGANISM: ARTIFICIAL SEQUENCE
<220> FEATURE:
<223> OTHER INFORMATION: SYNTHETIC PRIMER

<400> SEQUENCE: 58
gcttgtgctc tggatccc                                                  18

<210> SEQ ID NO 59
<211> LENGTH: 21
<212> TYPE: DNA
<213> ORGANISM: ARTIFICIAL SEQUENCE
<220> FEATURE:
<223> OTHER INFORMATION: SYNTHETIC PRIMER

<400> SEQUENCE: 59
srgatattgt gatgacgcag g                                              21

<210> SEQ ID NO 60
<211> LENGTH: 17
<212> TYPE: DNA
<213> ORGANISM: ARTIFICIAL SEQUENCE
<220> FEATURE:
<223> OTHER INFORMATION: SYNTHETIC PRIMER

<400> SEQUENCE: 60
ctgctgctct gggttcc                                                   17

<210> SEQ ID NO 61
<211> LENGTH: 20
<212> TYPE: DNA
<213> ORGANISM: ARTIFICIAL SEQUENCE

<220> FEATURE:
<223> OTHER INFORMATION: SYNTHETIC PRIMER

<400> SEQUENCE: 61
attgtgctga cccaatctcc                                                   20

<210> SEQ ID NO 62
<211> LENGTH: 20
<212> TYPE: DNA
<213> ORGANISM: ARTIFICIAL SEQUENCE
<220> FEATURE:
<223> OTHER INFORMATION: SYNTHETIC PRIMER

<400> SEQUENCE: 62
cagcttcctg ctaatcagtg                                                   20

<210> SEQ ID NO 63
<211> LENGTH: 20
<212> TYPE: DNA
<213> ORGANISM: ARTIFICIAL SEQUENCE
<220> FEATURE:
<223> OTHER INFORMATION: SYNTHETIC PRIMER

<400> SEQUENCE: 63
awtgtkctca cccagtctcc                                                   20

<210> SEQ ID NO 64
<211> LENGTH: 20
<212> TYPE: DNA
<213> ORGANISM: ARTIFICIAL SEQUENCE
<220> FEATURE:
<223> OTHER INFORMATION: SYNTHETIC PRIMER

<400> SEQUENCE: 64
ctcagatcct tggactthtg                                                   20

<210> SEQ ID NO 65
<211> LENGTH: 18
<212> TYPE: DNA
<213> ORGANISM: ARTIFICIAL SEQUENCE
<220> FEATURE:
<223> OTHER INFORMATION: SYNTHETIC PRIMER

<400> SEQUENCE: 65
gtctccagcc accctgtc                                                     18

<210> SEQ ID NO 66
<211> LENGTH: 18
<212> TYPE: DNA
<213> ORGANISM: ARTIFICIAL SEQUENCE
<220> FEATURE:
<223> OTHER INFORMATION: SYNTHETIC PRIMER

<400> SEQUENCE: 66
tggagtcaca gacycagg                                                     18

<210> SEQ ID NO 67
<211> LENGTH: 21
<212> TYPE: DNA
<213> ORGANISM: ARTIFICIAL SEQUENCE
<220> FEATURE:
<223> OTHER INFORMATION: SYNTHETIC PRIMER

<400> SEQUENCE: 67
tgatgaccca gtctcmcaaa t                                                 21

```
<210> SEQ ID NO 68
<211> LENGTH: 18
<212> TYPE: DNA
<213> ORGANISM: ARTIFICIAL SEQUENCE
<220> FEATURE:
<223> OTHER INFORMATION: SYNTHETIC PRIMER

<400> SEQUENCE: 68
tggagtttca gacccagg                                              18

<210> SEQ ID NO 69
<211> LENGTH: 20
<212> TYPE: DNA
<213> ORGANISM: ARTIFICIAL SEQUENCE
<220> FEATURE:
<223> OTHER INFORMATION: SYNTHETIC PRIMER

<400> SEQUENCE: 69
gcctgtgcag acattgtgat                                            20

<210> SEQ ID NO 70
<211> LENGTH: 18
<212> TYPE: DNA
<213> ORGANISM: ARTIFICIAL SEQUENCE
<220> FEATURE:
<223> OTHER INFORMATION: SYNTHETIC PRIMER

<400> SEQUENCE: 70
ctgctmtggg tatctggt                                              18

<210> SEQ ID NO 71
<211> LENGTH: 20
<212> TYPE: DNA
<213> ORGANISM: ARTIFICIAL SEQUENCE
<220> FEATURE:
<223> OTHER INFORMATION: SYNTHETIC PRIMER

<400> SEQUENCE: 71
cctgtgggga cattgtgatg                                            20

<210> SEQ ID NO 72
<211> LENGTH: 20
<212> TYPE: DNA
<213> ORGANISM: ARTIFICIAL SEQUENCE
<220> FEATURE:
<223> OTHER INFORMATION: SYNTHETIC PRIMER

<400> SEQUENCE: 72
cwtcttgttg ctctggtttc                                            20

<210> SEQ ID NO 73
<211> LENGTH: 20
<212> TYPE: DNA
<213> ORGANISM: ARTIFICIAL SEQUENCE
<220> FEATURE:
<223> OTHER INFORMATION: SYNTHETIC PRIMER

<400> SEQUENCE: 73
acatccrgat gacycagtct                                            20

<210> SEQ ID NO 74
<211> LENGTH: 19
<212> TYPE: DNA
<213> ORGANISM: ARTIFICIAL SEQUENCE
<220> FEATURE:
<223> OTHER INFORMATION: SYNTHETIC PRIMER

<400> SEQUENCE: 74
```

```
gatgtcctct gctcagttc                                              19

<210> SEQ ID NO 75
<211> LENGTH: 20
<212> TYPE: DNA
<213> ORGANISM: ARTIFICIAL SEQUENCE
<220> FEATURE:
<223> OTHER INFORMATION: SYNTHETIC PRIMER

<400> SEQUENCE: 75
ccagatgtga tatccagatg                                             20

<210> SEQ ID NO 76
<211> LENGTH: 18
<212> TYPE: DNA
<213> ORGANISM: ARTIFICIAL SEQUENCE
<220> FEATURE:
<223> OTHER INFORMATION: SYNTHETIC PRIMER

<400> SEQUENCE: 76
cctgctgagt tccttggg                                               18

<210> SEQ ID NO 77
<211> LENGTH: 21
<212> TYPE: DNA
<213> ORGANISM: ARTIFICIAL SEQUENCE
<220> FEATURE:
<223> OTHER INFORMATION: SYNTHETIC PRIMER

<400> SEQUENCE: 77
gccagatgtg atgtycaaat g                                           21

<210> SEQ ID NO 78
<211> LENGTH: 18
<212> TYPE: DNA
<213> ORGANISM: ARTIFICIAL SEQUENCE
<220> FEATURE:
<223> OTHER INFORMATION: SYNTHETIC PRIMER

<400> SEQUENCE: 78
ctgctgctgt ggcttaca                                               18

<210> SEQ ID NO 79
<211> LENGTH: 20
<212> TYPE: DNA
<213> ORGANISM: ARTIFICIAL SEQUENCE
<220> FEATURE:
<223> OTHER INFORMATION: SYNTHETIC PRIMER

<400> SEQUENCE: 79
atccagatga ctcagtctcc                                             20

<210> SEQ ID NO 80
<211> LENGTH: 19
<212> TYPE: DNA
<213> ORGANISM: ARTIFICIAL SEQUENCE
<220> FEATURE:
<223> OTHER INFORMATION: SYNTHETIC PRIMER

<400> SEQUENCE: 80
ccttctcaac ttctgctct                                              19

<210> SEQ ID NO 81
<211> LENGTH: 21
<212> TYPE: DNA
<213> ORGANISM: ARTIFICIAL SEQUENCE
```

```
<220> FEATURE:
<223> OTHER INFORMATION: SYNTHETIC PRIMER

<400> SEQUENCE: 81
cctgatatgt gacatccrva t                                              21

<210> SEQ ID NO 82
<211> LENGTH: 18
<212> TYPE: DNA
<213> ORGANISM: ARTIFICIAL SEQUENCE
<220> FEATURE:
<223> OTHER INFORMATION: SYNTHETIC PRIMER

<400> SEQUENCE: 82
agggcccytg ctcagttt                                                  18

<210> SEQ ID NO 83
<211> LENGTH: 20
<212> TYPE: DNA
<213> ORGANISM: ARTIFICIAL SEQUENCE
<220> FEATURE:
<223> OTHER INFORMATION: SYNTHETIC PRIMER

<400> SEQUENCE: 83
magatgaccc agtctccatc                                                20

<210> SEQ ID NO 84
<211> LENGTH: 18
<212> TYPE: DNA
<213> ORGANISM: ARTIFICIAL SEQUENCE
<220> FEATURE:
<223> OTHER INFORMATION: SYNTHETIC PRIMER

<400> SEQUENCE: 84
atgagggtcc ttgctgag                                                  18

<210> SEQ ID NO 85
<211> LENGTH: 21
<212> TYPE: DNA
<213> ORGANISM: ARTIFICIAL SEQUENCE
<220> FEATURE:
<223> OTHER INFORMATION: SYNTHETIC PRIMER

<400> SEQUENCE: 85
tgagatgtga catccagatg a                                              21

<210> SEQ ID NO 86
<211> LENGTH: 18
<212> TYPE: DNA
<213> ORGANISM: ARTIFICIAL SEQUENCE
<220> FEATURE:
<223> OTHER INFORMATION: SYNTHETIC PRIMER

<400> SEQUENCE: 86
gaggttccag gttcaggt                                                  18

<210> SEQ ID NO 87
<211> LENGTH: 21
<212> TYPE: DNA
<213> ORGANISM: ARTIFICIAL SEQUENCE
<220> FEATURE:
<223> OTHER INFORMATION: SYNTHETIC PRIMER

<400> SEQUENCE: 87
ccagtgtgat gtccagataa c                                              21
```

<210> SEQ ID NO 88
<211> LENGTH: 19
<212> TYPE: DNA
<213> ORGANISM: ARTIFICIAL SEQUENCE
<220> FEATURE:
<223> OTHER INFORMATION: SYNTHETIC PRIMER

<400> SEQUENCE: 88
ccatgaccat gytctcact                                          19

<210> SEQ ID NO 89
<211> LENGTH: 20
<212> TYPE: DNA
<213> ORGANISM: ARTIFICIAL SEQUENCE
<220> FEATURE:
<223> OTHER INFORMATION: SYNTHETIC PRIMER

<400> SEQUENCE: 89
acaactgtga cccagtctcc                                         20

<210> SEQ ID NO 90
<211> LENGTH: 21
<212> TYPE: DNA
<213> ORGANISM: ARTIFICIAL SEQUENCE
<220> FEATURE:
<223> OTHER INFORMATION: SYNTHETIC PRIMER

<400> SEQUENCE: 90
atggaaactc cagcttcatt t                                       21

<210> SEQ ID NO 91
<211> LENGTH: 20
<212> TYPE: DNA
<213> ORGANISM: ARTIFICIAL SEQUENCE
<220> FEATURE:
<223> OTHER INFORMATION: SYNTHETIC PRIMER

<400> SEQUENCE: 91
acacaggctc cagcttctct                                         20

<210> SEQ ID NO 92
<211> LENGTH: 20
<212> TYPE: DNA
<213> ORGANISM: ARTIFICIAL SEQUENCE
<220> FEATURE:
<223> OTHER INFORMATION: SYNTHETIC PRIMER

<400> SEQUENCE: 92
atgagaccgt ctattcagtt                                         20

<210> SEQ ID NO 93
<211> LENGTH: 20
<212> TYPE: DNA
<213> ORGANISM: ARTIFICIAL SEQUENCE
<220> FEATURE:
<223> OTHER INFORMATION: SYNTHETIC PRIMER

<400> SEQUENCE: 93
gtgctcagtg tgacatccag                                         20

<210> SEQ ID NO 94
<211> LENGTH: 21
<212> TYPE: DNA
<213> ORGANISM: ARTIFICIAL SEQUENCE
<220> FEATURE:
<223> OTHER INFORMATION: SYNTHETIC PRIMER

<400> SEQUENCE: 94
tstacttacg tttbatttcc a                                              21

<210> SEQ ID NO 95
<211> LENGTH: 21
<212> TYPE: DNA
<213> ORGANISM: ARTIFICIAL SEQUENCE
<220> FEATURE:
<223> OTHER INFORMATION: SYNTHETIC PRIMER

<400> SEQUENCE: 95
tttbatttcc agcttggtsc c                                              21

<210> SEQ ID NO 96
<211> LENGTH: 16
<212> TYPE: DNA
<213> ORGANISM: ARTIFICIAL SEQUENCE
<220> FEATURE:
<223> OTHER INFORMATION: SYNTHETIC PRIMER

<400> SEQUENCE: 96
tcaagaagca cacgac                                                    16

<210> SEQ ID NO 97
<211> LENGTH: 20
<212> TYPE: DNA
<213> ORGANISM: ARTIFICIAL SEQUENCE
<220> FEATURE:
<223> OTHER INFORMATION: SYNTHETIC PRIMER

<400> SEQUENCE: 97
gcacctccag atgttaactg                                                20

<210> SEQ ID NO 98
<211> LENGTH: 20
<212> TYPE: DNA
<213> ORGANISM: ARTIFICIAL SEQUENCE
<220> FEATURE:
<223> OTHER INFORMATION: SYNTHETIC PRIMER

<400> SEQUENCE: 98
gatggtggga agatggatac                                                20

<210> SEQ ID NO 99
<211> LENGTH: 21
<212> TYPE: DNA
<213> ORGANISM: ARTIFICIAL SEQUENCE
<220> FEATURE:
<223> OTHER INFORMATION: SYNTHETIC PRIMER

<400> SEQUENCE: 99
gcctggaytt cacttatact c                                              21

<210> SEQ ID NO 100
<211> LENGTH: 19
<212> TYPE: DNA
<213> ORGANISM: ARTIFICIAL SEQUENCE
<220> FEATURE:
<223> OTHER INFORMATION: SYNTHETIC PRIMER

<400> SEQUENCE: 100
tcccaggctg ttgtgactc                                                 19

<210> SEQ ID NO 101
<211> LENGTH: 19
<212> TYPE: DNA
<213> ORGANISM: ARTIFICIAL SEQUENCE

```
<220> FEATURE:
<223> OTHER INFORMATION: SYNTHETIC PRIMER

<400> SEQUENCE: 101
tggcctggac tcctctctt                                                  19

<210> SEQ ID NO 102
<211> LENGTH: 20
<212> TYPE: DNA
<213> ORGANISM: ARTIFICIAL SEQUENCE
<220> FEATURE:
<223> OTHER INFORMATION: SYNTHETIC PRIMER

<400> SEQUENCE: 102
caacttgtgc tcactcagtc                                                 20

<210> SEQ ID NO 103
<211> LENGTH: 18
<212> TYPE: DNA
<213> ORGANISM: ARTIFICIAL SEQUENCE
<220> FEATURE:
<223> OTHER INFORMATION: SYNTHETIC PRIMER

<400> SEQUENCE: 103
actcagccaa gctctgtg                                                   18

<210> SEQ ID NO 104
<211> LENGTH: 21
<212> TYPE: DNA
<213> ORGANISM: ARTIFICIAL SEQUENCE
<220> FEATURE:
<223> OTHER INFORMATION: SYNTHETIC PRIMER

<400> SEQUENCE: 104
ctctaggaag cacagtcaaa c                                               21

<210> SEQ ID NO 105
<211> LENGTH: 18
<212> TYPE: DNA
<213> ORGANISM: ARTIFICIAL SEQUENCE
<220> FEATURE:
<223> OTHER INFORMATION: SYNTHETIC PRIMER

<400> SEQUENCE: 105
gycactyacc taggacag                                                   18

<210> SEQ ID NO 106
<211> LENGTH: 20
<212> TYPE: DNA
<213> ORGANISM: ARTIFICIAL SEQUENCE
<220> FEATURE:
<223> OTHER INFORMATION: SYNTHETIC PRIMER

<400> SEQUENCE: 106
aaactactta cctaggacag                                                 20

<210> SEQ ID NO 107
<211> LENGTH: 21
<212> TYPE: DNA
<213> ORGANISM: ARTIFICIAL SEQUENCE
<220> FEATURE:
<223> OTHER INFORMATION: SYNTHETIC PRIMER

<400> SEQUENCE: 107
taggacagtc agtttggttc c                                               21
```

```
<210> SEQ ID NO 108
<211> LENGTH: 20
<212> TYPE: DNA
<213> ORGANISM: ARTIFICIAL SEQUENCE
<220> FEATURE:
<223> OTHER INFORMATION: SYNTHETIC PRIMER

<400> SEQUENCE: 108
aggacagtga ccttggttcc                                           20

<210> SEQ ID NO 109
<211> LENGTH: 16
<212> TYPE: DNA
<213> ORGANISM: ARTIFICIAL SEQUENCE
<220> FEATURE:
<223> OTHER INFORMATION: SYNTHETIC PRIMER

<400> SEQUENCE: 109
acaccagtgt ggcytt                                               16

<210> SEQ ID NO 110
<211> LENGTH: 19
<212> TYPE: DNA
<213> ORGANISM: ARTIFICIAL SEQUENCE
<220> FEATURE:
<223> OTHER INFORMATION: SYNTHETIC PRIMER

<400> SEQUENCE: 110
agctcctcag rggaaggtg                                            19

<210> SEQ ID NO 111
<211> LENGTH: 19
<212> TYPE: DNA
<213> ORGANISM: ARTIFICIAL SEQUENCE
<220> FEATURE:
<223> OTHER INFORMATION: SYNTHETIC PRIMER

<400> SEQUENCE: 111
gaaacacggt gagwgtggg                                            19

<210> SEQ ID NO 112
<211> LENGTH: 19
<212> TYPE: DNA
<213> ORGANISM: ARTIFICIAL SEQUENCE
<220> FEATURE:
<223> OTHER INFORMATION: SYNTHETIC PRIMER

<400> SEQUENCE: 112
gaaacagggt gactgatgg                                            19
```

NESTED PRIMER SETS FOR AMPLIFYING MOUSE IMMUNOGLOBULIN VARIABLE GENE SEGMENTS

CLAIM OF PRIORITY

The present patent application claims the priority benefit of the filing date of Indian Application No. 634/DEL/2008 filed Mar. 13, 2008, the entire content of which is incorporated herein by reference in its entirety.

FIELD OF INVENTION

The present invention concerns the fields of immunology. More specifically, the present invention relates to oligonucleotides for detection of rearrangement of immunoglobulin genes.

BACKGROUND OF THE INVENTION

Humoral immunity relies on the specific recognition and elimination of foreign antigen (Ag), brought about by immunoglobulin (Ig) Ag receptors present on B cells. The humoral immune system needs a vast and diverse array of antibody (Ab) molecules to specifically recognize the extensive and varied world of potential Ags. It achieves this in part by encoding a large array of germline variable (V), diversity (D) and joining (J) gene segments. The germline, junctional and combinatorial diversity, together with Ag dependent changes such as somatic hypermutation and receptor editing, collectively produce a potentially vast diversity of V gene sequences.

The specialized microenvironments present in secondary lymphoid organs like the spleen and lymph nodes, where T-cell dependent Ab responses occur, are referred to as germinal centers. In germinal centers, Ag specific B cells undergo clonal expansion, somatic hypermutation, isotype class switching, affinity maturation, Ag-driven selection and differentiation into memory B cells or plasma cells.

PCR technology has been used for studying various aspects of B cell biology such as B cell repertoire analysis, expression of Ab using phage display systems and detection of B cell clonality in diagnostic haematopathology. Using PCR technology, numerous investigators have tried to devise a universal primer or set of primers for amplifying all possible mouse V gene rearrangements (Chiang et al., 1989; LeBoeuf et al., 1989; Orlandi et al., 1989; Larrick et al., 1990; Coloma et al., 1991; Kettleborough et al., 1993; Nicholls et al., 1993; Zhou et al., 1994; Dattamajumdar et al., 1996; Lan et al., 1996; Krebber et al., 1997). These primers, degenerate or otherwise, were however not successful in amplifying all the V gene segments (Owens and Young, 1994; Ruberti et al., 1994; Wang et al., 2006). Several workers have tried to overcome the shortcomings of the earlier efforts by designing a few, highly degenerate (1- to 128-fold or more degeneracy) primers (Jones and Bendig, 1991; Wang et al., 2000; Essono et al., 2003). In general, highly degenerate primers have higher propensity to lead to cross-family amplification. An alternative approach involves designing a panel of primers with minimum degeneracy (Chardes et al., 1999; Seijen et al., 2001). These studies (Chiang et al., 1989; LeBoeuf et al., 1989; Orlandi et al., 1989; Larrick et al., 1990; Coloma et al., 1991; Jones and Bendig, 1991; Kettleborough et al., 1993; Nicholls et al., 1993; Owens and Young, 1994; Ruberti et al., 1994; Zhou et al., 1994; Dattamajumdar et al., 1996; Lan et al., 1996; Krebber et al., 1997; Chardes et al., 1999; Wang et al., 2000; Seijen et al., 2001; Essono et al., 2003; Wang et al., 2006) designed primers for a standard PCR. Further, they do not report the PCR detection limit achieved using their primer set which is unlikely to be sensitive enough to be able to amplify the rearranged $V_H$ and $V_L$ genes from a single or a small number of B cells. To enhance the sensitivity and specificity of the PCR for analysis of the rearranged $V_H$ and $V_L$ genes from single B cells, researchers working on the human and rabbit systems have resorted to a nested PCR strategy (Brezinschek et al., 1995; Foster et al., 1997; Sehgal et al., 1998; Farner et al., 1999; Dohmen et al., 2005).

The major challenge in using PCR technology for studying mouse Ab genes, whether expressed in homogeneous hybridoma cell lines or a heterogeneous splenic B cell population, is to ensure broad and highly specific amplification. This need arises due to the fact that the mouse V genes show intra- and inter-family sequence variability, and somatically rearrange to generate nearly limitless Ab diversity. Additionally, somatic hypermutation events that coincide with the primer binding sites can potentially adversely affect the efficiency of amplification.

In order to study V gene usage, somatic hypermutation patterns, clonal expansion and selection in Ag-specific splenic B cells in experimental system, one would require a PCR primer set and an amplification strategy that would potentially amplify all possible rearranged V genes from a single or a small number of B cells in a highly sensitive and specific manner. A nested primer set that can potentially amplify the rearranged $V_H$ and $V_L$ genes belonging to any V gene family from single or small number of mouse B cells in a representative and highly specific manner has not been reported.

The present invention discloses a novel nested PCR primer set that amplifies all possible mouse rearranged/expressed $V_H$, $V_\kappa$ and $V_\lambda$ genes from C57BL/6 and BALB/c mice in an isotype-independent manner with minimum cross reactivity, low degeneracy, high specificity and sensitivity, using genomic DNA or total RNA from small number of B cells.

SUMMARY OF THE INVENTION

The present invention relates to oligonucleotides for detection of rearrangement of immunoglobulin genes for identifying clonality of cells, cancer cells, hypermutation in immunoglobulin gene, antibody isotype producing cell and/or assaying B cell repertoire in a sample. The oligonucleotides provided in the present invention amplify all possible mouse rearranged/expressed $V_H$, $V_\kappa$ and $V_\lambda$ genes from C57BL/6 and BALB/c mice in an isotype-independent manner with minimum cross reactivity, low degeneracy, high specificity and sensitivity, using genomic DNA or total RNA from small number of B cells.

One aspect of the present invention relates to a set of oligonucleotides for assaying rearrangement of immunoglobulin genes for identifying clonality of cells, cancer cells, hypermutation in immunoglobulin gene, antibody isotype producing cell and/or assaying B cell repertoire in a sample, wherein nucleotide sequences of said oligonucleotides are as set forth in SEQ ID NO: 1 to 112.

Another aspect of the present invention relates to a set of oligonucleotides for assaying rearrangement of immunoglobulin genes for identifying clonality of cells, cancer cells, hypermutation in immunoglobulin gene, antibody isotype producing cell and/or assaying B cell repertoire in a sample, wherein nucleotide sequences of said set of oligonucleotides is selected from the group consisting of set 1: SEQ ID NO: 1 to 37, SEQ ID NO: 55 to 95 and SEQ ID NO: 99 to 108; and set 44: SEQ ID NO: 1 to 34, SEQ ID NO: 38 to 93, SEQ ID NO: 96 to 104 and SEQ ID NO: 109 to 112.

Another aspect of the present invention relates to a set of oligonucleotides for assaying rearrangement of immunoglobulin genes for identifying clonality of cells, cancer cells, hypermutation in immunoglobulin gene, antibody isotype producing cell and/or assaying B cell repertoire in a sample, wherein nucleotide sequences of said set of oligonucleotides is selected from the group consisting of set 2: SEQ ID NO: 1 to 37, set 3: SEQ ID NO: 1 to 4 and SEQ ID NO: 35-37, set 4: SEQ ID NO: 5 to 6 and SEQ ID NO: 35 to 37, set 5: SEQ ID NO: 7 to 8 and SEQ ID NO: 35-37, set 6: SEQ ID NO: 9 to 10 and SEQ ID NO: 35-37, set 7: SEQ ID NO: 11 to 12 and SEQ ID NO: 35-37; set 8: SEQ ID NO: 13 to 14 and SEQ ID NO: 35-37; set 9: SEQ ID NO: 15 to 16 and SEQ ID NO: 35-37; set 10: SEQ ID NO: 17 to 18 and SEQ ID NO: 35-37; set 11: SEQ ID NO: 19 to 20 and SEQ ID NO: 35-37; set 12: SEQ ID NO: 21-22 and SEQ ID NO: 35-37; set 13: SEQ ID NO: 23 to 24 and SEQ ID NO: 35-37; set 14: SEQ ID NO: 25 to 26 and SEQ ID NO: 35-37; set 15: SEQ ID NO: 27 to 28 and SEQ ID NO: 29 to 30; set 16: SEQ ID NO: 29 to 30 and SEQ ID NO: 35-37; set 17: SEQ ID NO: 31 to 32 and SEQ ID NO: 35-37; and set 18: SEQ ID NO: 33-37.

Still another aspect of the present invention relates to a set of oligonucleotides for assaying rearrangement of immunoglobulin genes for identifying clonality of cells, cancer cells, hypermutation in immunoglobulin gene, antibody isotype producing cell and/or assaying B cell repertoire in a sample, wherein nucleotide sequences of said set of oligonucleotides are as set forth in set 19: SEQ ID NO: 55 to 95 and SEQ ID NO: 99 to 108.

Still another aspect of the present invention relates to a set of oligonucleotides for assaying rearrangement of immunoglobulin genes for identifying clonality of cells, cancer cells, hypermutation in immunoglobulin gene, antibody isotype producing cell and/or assaying B cell repertoire in a sample, wherein nucleotide sequences of said set of oligonucleotides is selected from the group consisting of set 20: SEQ ID NO: 55 to 95; set 21: SEQ ID NO: 55 to 57 and SEQ ID NO: 94 to 95; set 22: SEQ ID NO: 58 to 59 and SEQ ID NO: 94 to 95; set 23: SEQ ID NO: 60 to 61 and SEQ ID NO: 94 to 95; set 24: SEQ ID NO: 62 to 63 and SEQ ID NO: 94 to 95; set 25: SEQ ID NO: 64 to 65 and SEQ ID NO: 94 to 95; set 26: SEQ ID NO: 66 to 67 and SEQ ID NO: 94 to 95; set 27: SEQ ID NO: 68 to 69 and SEQ ID NO: 94 to 95; set 28: SEQ ID NO: 70 to 71 and SEQ ID NO: 94 to 95; set 29: SEQ ID NO: 72 to 73 and SEQ ID NO: 94 to 95; set 30: SEQ ID NO: 74 to 75 and SEQ ID NO: 94 to 95; set 31: SEQ ID NO: 76 to 77 and SEQ ID NO: 94 to 95; set 32: SEQ ID NO: 78 to 79 and SEQ ID NO: 94 to 95; set 33: SEQ ID NO: 80 to 81 and SEQ ID NO: 94 to 95; set 34: SEQ ID NO: 82 to 83 and SEQ ID NO: 94 to 95; set 35: SEQ ID NO: 84 to 85 and SEQ ID NO: 94 to 95; set 36: SEQ ID NO: 86 to 87 and SEQ ID NO: 94 to 95; set 37: SEQ ID NO: 88 to 89 and SEQ ID NO: 94 to 95; set 38: SEQ ID NO: 90 to 91 and SEQ ID NO: 94 to 95; and set 39: SEQ ID NO: 92 to 95.

Still another aspect of the present invention relates to a set of oligonucleotides for assaying rearrangement of immunoglobulin genes for identifying clonality of cells, cancer cells, hypermutation in immunoglobulin gene, antibody isotype producing cell and/or assaying B cell repertoire in a sample, wherein nucleotide sequences of said set of oligonucleotides is selected from the group consisting of set 40: SEQ ID NO: 99 to 108; set 41: SEQ ID NO: 99 to 100 and SEQ ID NO: 105 to 108; set 42: SEQ ID NO: 101 to 102 and SEQ ID NO: 105 to 108; and set 43: SEQ ID NO: 103 to 108.

Further aspect of the present invention relates to a set of oligonucleotides for assaying rearrangement of immunoglobulin genes for identifying clonality of cells, cancer cells, hypermutation in immunoglobulin gene, antibody isotype producing cell and/or assaying B cell repertoire in a sample, wherein nucleotide sequences of said set of oligonucleotides is selected from the group consisting of set 45: SEQ ID NO: 1 to 34, SEQ ID NO: 38-54; set 46: SEQ ID NO: 1 to 34, SEQ ID NO: 38, SEQ ID NO: 43 to 44; set 47: SEQ ID NO: 1 to 34, SEQ ID NO: 39, SEQ ID NO: 45 to 48; set 48: SEQ ID NO: 1 to 34, SEQ ID NO: 40, SEQ ID NO: 49 to 50; set 49: SEQ ID NO: 1 to 34, SEQ ID NO: 41, SEQ ID NO: 51 to 52; set 50: SEQ ID NO: 1 to 34, SEQ ID NO: 42, SEQ ID NO: 53 to 54; set 51: SEQ ID NO: 1 to 4 and SEQ ID NO: 38 to 54; set 52: SEQ ID NO: 5 to 6 and SEQ ID NO: 38 to 54; set 53: SEQ ID NO: 7 to 8 and SEQ ID NO: 38 to 54; set 54: SEQ ID NO: 9 to 10 and SEQ ID NO: 38 to 54; set 55: SEQ ID NO: 11 to 12 and SEQ ID NO: 38 to 54; set 56: SEQ ID NO: 13 to 14 and SEQ ID NO: 38 to 54; set 57: SEQ ID NO: 15 to 16 and SEQ ID NO: 38 to 54; set 58: SEQ ID NO: 17 to 18 and SEQ ID NO: 38 to 54; set 59: SEQ ID NO: 19 to 20 and SEQ ID NO: 38 to 54; set 60: SEQ ID NO: 21 to 22 and SEQ ID NO: 38 to 54; set 61: SEQ ID NO: 23 to 24 and SEQ ID NO: 38 to 54; set 62: SEQ ID NO: 25 to 26 and SEQ ID NO: 38 to 54; set 63: SEQ ID NO: 27 to 28 and SEQ ID NO: 38 to 54; set 64: SEQ ID NO: 29 to 30 and SEQ ID NO: 38 to 54; set 65: SEQ ID NO: 31 to 32 and SEQ ID NO: 38 to 54; and set 66: SEQ ID NO: 33 to 34 and SEQ ID NO: 38 to 54.

Another aspect of the present invention relates to a set of oligonucleotides for assaying rearrangement of immunoglobulin genes for identifying clonality of cells, cancer cells, hypermutation in immunoglobulin gene, antibody isotype producing cell and/or assaying B cell repertoire in a sample, wherein nucleotide sequences of said set of oligonucleotides is selected from the group consisting of set 67: SEQ ID NO: 55 to 93; SEQ ID NO: 96 to 104 and SEQ ID NO: 109 to 112; set 68: SEQ ID NO: 55 to 93 and SEQ ID NO: 96 to 98, set 69: SEQ ID NO: 55 to 57 and SEQ ID NO: 96 to 98, set 70: SEQ ID NO: 58 to 59 and SEQ ID NO: 96 to 98, set 71: SEQ ID NO: 60 to 61 and SEQ ID NO: 96 to 98, set 72: SEQ ID NO: 62 to 63 and SEQ ID NO: 96 to 98, set 73: SEQ ID NO: 64 to 65 and SEQ ID NO: 96 to 98, set 74: SEQ ID NO: 66 to 67 and SEQ ID NO: 96 to 98, set 75: SEQ ID NO: 68 to 69 and SEQ ID NO: 96 to 98, set 76: SEQ ID NO: 70 to 71 and SEQ ID NO: 96 to 98, set 77: SEQ ID NO: 72 to 73 and SEQ ID NO: 96 to 98, set 78: SEQ ID NO: 74 to 75 and SEQ ID NO: 96 to 98, set 79: SEQ ID NO: 76 to 77 and SEQ ID NO: 96 to 98, set 80: SEQ ID NO: 78 to 79 and SEQ ID NO: 96 to 98; set 81: SEQ ID NO: 80 to 81 and SEQ ID NO: 96 to 98; set 82: SEQ ID NO: 82 to 83 and SEQ ID NO: 96 to 98, set 83: SEQ ID NO: 84 to 85 and SEQ ID NO: 96 to 98; set 84: SEQ ID NO: 86 to 87 and SEQ ID NO: 96 to 98; set 85: SEQ ID NO: 88 to 89 and SEQ ID NO: 96 to 98; set 86: SEQ ID NO: 90 to 91 and SEQ ID NO: 96 to 98; set 87: SEQ ID NO: 92 to 93 and SEQ ID NO: 96 to 98; set 88: SEQ ID NO: 99 to 104 and SEQ ID NO: 109 to 112; set 89: SEQ ID NO: 99 to 100 and SEQ ID NO: 109 to 112; set 90: SEQ ID NO: 101 to 102 and SEQ ID NO: 109 to 112; and set 91: SEQ ID NO: 103 to 104 and SEQ ID NO: 109 to 112.

Another aspect of the present invention relates to a set of oligonucleotides for assaying rearrangement of immunoglobulin genes for identifying clonality of cells, cancer cells, hypermutation in immunoglobulin gene, antibody isotype producing cell and/or assaying B cell repertoire in a sample, wherein nucleotide sequences of said oligonucleotides are as set forth in SEQ ID NO: 1 to 54.

Yet another aspect of the present invention relates to a set of oligonucleotides for assaying rearrangement of immunoglobulin genes for identifying clonality of cells, cancer cells, hypermutation in immunoglobulin gene, antibody isotype producing cell and/or assaying B cell repertoire in a sample, wherein nucleotide sequences of said oligonucleotides are as set forth in SEQ ID NO: 55 to 98.

Still another aspect of the present invention relates to a set of oligonucleotides for assaying rearrangement of immunoglobulin genes for identifying clonality of cells, cancer cells, hypermutation in immunoglobulin gene, antibody isotype producing cell and/or assaying B cell repertoire in a sample, wherein nucleotide sequences of said oligonucleotides are as set forth in SEQ ID NO: 98 to 112.

Still another aspect of the present invention relates to a process of assaying rearrangement of immunoglobulin genes for identifying clonality of cells, cancer cells, hypermutation in immunoglobulin gene, antibody isotype producing cell and/or assaying B cell repertoire in a sample using the set of oligonucleotides as set forth in SEQ ID NO: 1-112.

Still another aspect of the present invention relates to a process of assaying rearrangement of immunoglobulin genes for identifying clonality of cells, cancer cells, hypermutation in immunoglobulin gene, antibody isotype producing cell and/or assaying B cell repertoire in a sample; the process comprises providing a sample; providing a first set of oligonucleotides as set forth in SEQ ID NO: 1, SEQ ID NO: 2, SEQ ID NO: 5, SEQ ID NO: 7, SEQ ID NO: 9, SEQ ID NO: 1, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 55, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 99, SEQ ID NO: 101, SEQ ID NO: 103, SEQ ID NO: 105 and SEQ ID NO: 106; performing a first round of polymerase chain reaction to obtain first product; performing second round of polymerase chain reaction using said first product and oligonucleotide as set forth in SEQ ID No. 3, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 37, SEQ ID NO: 56, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 100, SEQ ID NO: 102, SEQ ID NO: 104, SEQ ID NO: 107 and SEQ ID NO: 108; and detecting presence of an amplified product.

Still another aspect of the present invention relates to a process of assaying rearrangement of immunoglobulin genes for identifying clonality of cells, cancer cells, hypermutation in immunoglobulin gene, antibody isotype producing cell and/or assaying B cell repertoire in a sample; the process comprises providing a sample; providing a first set of oligonucleotides as set forth in SEQ ID NO: 1, SEQ ID NO: 2, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 55, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 99, SEQ ID NO: 101, SEQ ID NO: 103, SEQ ID NO: 105 and SEQ ID NO: 106; performing a first round of polymerase chain reaction to obtain first product; performing second round of polymerase chain reaction using said first product and oligonucleotide as set forth in SEQ ID No. 3, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: SEQ ID NO: 26, SEQ ID NO: 28, SEQ ID NO: 30, SEQ ID NO: 32, SEQ ID NO: 34, SEQ ID NO: 44, SEQ ID NO: 47, SEQ ID NO: 48, SEQ ID NO: 50, SEQ ID NO: 52 and SEQ ID NO: 54; detecting presence of an amplified product.

Still another aspect of the present invention relates to a process for constructing library of polynucleotides encoding immunoglobulin genes, said process comprises amplifying immunoglobulin genes using the oligonucleotide sequences as set forth in SEQ ID NO: 1-112 to obtain amplified product; cloning said amplified product in an expression vector to obtain a recombinant expression vector; and transforming said recombinant expression vector in a host cell.

Still another aspect of the present invention relates to a kit for assaying rearrangement of immunoglobulin genes for identifying clonality of cells, cancer cells, hypermutation in immunoglobulin gene, antibody isotype producing cell and/or assaying B cell repertoire in a sample, wherein said kit comprises nucleotide sequences of said oligonucleotides are as set forth in SEQ ID NO: 1 to 112.

Still another aspect of the present invention relates to a kit for assaying rearrangement of immunoglobulin genes for identifying clonality of cells, cancer cells, hypermutation in immunoglobulin gene, antibody isotype producing cell and/or assaying B cell repertoire in a sample, wherein said kit comprises at least one set of oligonucleotides selected from the group consisting of set 1: SEQ ID NO: 1 to 37, SEQ ID NO: 55 to 95 and SEQ ID NO: 99 to 108; and set 44: SEQ ID NO: 1 to 34, SEQ ID NO: 38 to 93, SEQ ID NO: 96 to 104 and SEQ ID NO: 109 to 112.

Still another aspect of the present invention relates to a kit for assaying rearrangement of immunoglobulin genes for identifying clonality of cells, cancer cells, hypermutation in immunoglobulin gene, antibody isotype producing cell and/or assaying B cell repertoire in a sample, wherein said kit comprises at least one set of oligonucleotides selected from the group consisting of set 2: SEQ ID NO: 1 to 37, set 3: SEQ ID NO: 1 to 4 and SEQ ID NO: 35-37, set 4: SEQ ID NO: 5 to 6 and SEQ ID NO: 35 to 37, set 5: SEQ ID NO: 7 to 8 and SEQ ID NO: 35-37, set 6: SEQ ID NO: 9 to 10 and SEQ ID NO: 35-37, set 7: SEQ ID NO: 11 to 12 and SEQ ID NO: 35-37; set 8: SEQ ID NO: 13 to 14 and SEQ ID NO: 35-37; set 9: SEQ ID NO: 15 to 16 and SEQ ID NO: 35-37; set 10: SEQ ID NO: 17 to 18 and SEQ ID NO: 35-37; set 11: SEQ ID NO: 19 to 20 and SEQ ID NO: 35-37; set 12: SEQ ID NO: 21-22 and SEQ ID NO: 35-37; set 13: SEQ ID NO: 23 to 24 and SEQ ID NO: 35-37; set 14: SEQ ID NO: 25 to 26 and SEQ ID NO: 35-37; set 15: SEQ ID NO: 27 to 28 and SEQ ID NO: 29 to 30; set 16: SEQ ID NO: 29 to 30 and SEQ ID NO: 35-37; set 17: SEQ ID NO: 31 to 32 and SEQ ID NO: 35-37; and set 18: SEQ ID NO: 33-37.

Still another aspect of the present invention relates to a kit for assaying rearrangement of immunoglobulin genes for identifying clonality of cells, cancer cells, hypermutation in immunoglobulin gene, antibody isotype producing cell and/or assaying B cell repertoire in a sample, wherein said kit comprises set 19: SEQ ID NO: 55 to 95 and SEQ ID NO: 99 to 108.

Still another aspect of the present invention relates to a kit for assaying rearrangement of immunoglobulin genes for identifying clonality of cells, cancer cells, hypermutation in immunoglobulin gene, antibody isotype producing cell and/or assaying B cell repertoire in a sample, wherein said kit comprises at least one set of oligonucleotides selected from the group consisting of set 20: SEQ ID NO: 55 to 95; set 21: SEQ ID NO: 55 to 57 and SEQ ID NO: 94 to 95; set 22: SEQ ID NO: 58 to 59 and SEQ ID NO: 94 to 95; set 23: SEQ ID NO: 60 to 61 and SEQ ID NO: 94 to 95; set 24: SEQ ID NO: 62 to 63 and SEQ ID NO: 94 to 95; set 25: SEQ ID NO: 64 to 65 and SEQ ID NO: 94 to 95; set 26: SEQ ID NO: 66 to 67 and SEQ ID NO: 94 to 95; set 27: SEQ ID NO: 68 to 69 and SEQ ID NO: 94 to 95; set 28: SEQ ID NO: 70 to 71 and SEQ ID NO: 94 to 95; set 29: SEQ ID NO: 72 to 73 and SEQ ID NO: 94 to 95; set 30: SEQ ID NO: 74 to 75 and SEQ ID NO: 94 to 95; set 31: SEQ ID NO: 76 to 77 and SEQ ID NO: 94 to 95; set 32: SEQ ID NO: 78 to 79 and SEQ ID NO: 94 to 95; set 33: SEQ ID NO: 80 to 81 and SEQ ID NO: 94 to 95; set 34: SEQ ID NO: 82 to 83 and SEQ ID NO: 94 to 95; set 35: SEQ ID NO: 84 to 85 and SEQ ID NO: 94 to 95; set 36: SEQ ID NO: 86 to 87 and SEQ ID NO: 94 to 95; set 37: SEQ ID NO: 88 to 89 and SEQ ID NO: 94 to 95; set 38: SEQ ID NO: 90 to 91 and SEQ ID NO: 94 to 95; and set 39: SEQ ID NO: 92 to 95.

Still another aspect of the present invention relates to a kit for assaying rearrangement of immunoglobulin genes for identifying clonality of cells, cancer cells, hypermutation in immunoglobulin gene, antibody isotype producing cell and/or assaying B cell repertoire in a sample, wherein said kit comprises at least one set of oligonucleotides selected from the group consisting of set 40: SEQ ID NO: 99 to 108; set 41: SEQ ID NO: 99 to 100 and SEQ ID NO: 105 to 108; set 42: SEQ ID NO: 101 to 102 and SEQ ID NO:105 to 108; and set 43: SEQ ID NO: 103 to 108.

Still another aspect of the present invention relates to a kit for assaying rearrangement of immunoglobulin genes for identifying clonality of cells, cancer cells, hypermutation in immunoglobulin gene, antibody isotype producing cell and/or assaying B cell repertoire in a sample, wherein said kit comprises at least one set of oligonucleotides selected from the group consisting of set 45: SEQ ID NO: 1 to 34, SEQ ID NO: 38-54; set 46: SEQ ID NO: 1 to 34, SEQ ID NO: 38, SEQ ID NO: 43 to 44; set 47: SEQ ID NO: 1 to 34, SEQ ID NO: 39, SEQ ID NO: 45 to 48; set 48: SEQ ID NO: 1 to 34, SEQ ID NO: 40, SEQ ID NO: 49 to 50; set 49: SEQ ID NO: 1 to 34, SEQ ID NO: 41, SEQ ID NO: 51 to 52; set 50: SEQ ID NO: 1 to 34, SEQ ID NO: 42, SEQ ID NO: 53 to 54; set 51: SEQ ID NO: 1 to 4 and SEQ ID NO: 38 to 54; set 52: SEQ ID NO: 5 to 6 and SEQ ID NO: 38 to 54; set 53: SEQ ID NO: 7 to 8 and SEQ ID NO: 38 to 54; set 54: SEQ ID NO: 9 to 10 and SEQ ID NO: 38 to 54; set 55: SEQ ID NO: 11 to 12 and SEQ ID NO: 38 to 54; set 56: SEQ ID NO: 13 to 14 and SEQ ID NO: 38 to 54; set 57: SEQ ID NO: 15 to 16 and SEQ ID NO: 38 to 54; set 58: SEQ ID NO: 17 to 18 and SEQ ID NO: 38 to 54; set 59: SEQ ID NO: 19 to 20 and SEQ ID NO: 38 to 54; set 60: SEQ ID NO: 21 to 22 and SEQ ID NO: 38 to 54; set 61: SEQ ID NO: 23 to 24 and SEQ ID NO: 38 to 54; set 62: SEQ ID NO: 25 to 26 and SEQ ID NO: 38 to 54; set 63: SEQ ID NO: 27 to 28 and SEQ ID NO: 38 to 54; set 64: SEQ ID NO: 29 to 30 and SEQ ID NO: 38 to 54; set 65: SEQ ID NO: 31 to 32 and SEQ ID NO: 38 to 54; and set 66: SEQ ID NO: 33 to 34 and SEQ ID NO: 38 to 54.

Still another aspect of the present invention relates to a kit for assaying rearrangement of immunoglobulin genes for identifying clonality of cells, cancer cells, hypermutation in immunoglobulin gene, antibody isotype producing cell and/or assaying B cell repertoire in a sample, wherein said kit comprises at least one set of oligonucleotides selected from the group consisting of set 67: SEQ ID NO: 55 to 93; SEQ ID NO: 96 to 104 and SEQ ID NO: 109 to 112; set 68: SEQ ID NO: 55 to 93 and SEQ ID NO: 96 to 98, set 69: SEQ ID NO: 55 to 57 and SEQ ID NO: 96 to 98, set 70: SEQ ID NO: 58 to 59 and SEQ ID NO: 96 to 98, set 71: SEQ ID NO: 60 to 61 and SEQ ID NO: 96 to 98, set 72: SEQ ID NO: 62 to 63 and SEQ ID NO: 96 to 98, set 73: SEQ ID NO: 64 to 65 and SEQ ID NO: 96 to 98, set 74: SEQ ID NO: 66 to 67 and SEQ ID NO: 96 to 98, set 75: SEQ ID NO: 68 to 69 and SEQ ID NO: 96 to 98, set 76: SEQ ID NO: 70 to 71 and SEQ ID NO: 96 to 98, set 77: SEQ ID NO: 72 to 73 and SEQ ID NO: 96 to 98, set 78: SEQ ID NO: 74 to 75 and SEQ ID NO: 96 to 98, set 79: SEQ ID NO: 76 to 77 and SEQ ID NO: 96 to 98, set 80: SEQ ID NO: 78 to 79 and SEQ ID NO: 96 to 98; set 81: SEQ ID NO: 80 to 81 and SEQ ID NO: 96 to 98; set 82: SEQ ID NO: 82 to 83 and SEQ ID NO: 96 to 98; set 83: SEQ ID NO: 84 to 85 and SEQ ID NO: 96 to 98; set 84: SEQ ID NO: 86 to 87 and SEQ ID NO: 96 to 98; set 85: SEQ ID NO: 88 to 89 and SEQ ID NO: 96 to 98; set 86: SEQ ID NO: 90 to 91 and SEQ ID NO: 96 to 98; set 87: SEQ ID NO: 92 to 93 and SEQ ID NO: 96 to 98; set 88: SEQ ID NO: 99 to 104 and SEQ ID NO: 109 to 112; set 89: SEQ ID NO:99 to 100 and SEQ ID NO: 109 to 112; set 90: SEQ ID NO: 101 to 102 and SEQ ID NO: 109 to 112; and set 91: SEQ ID NO: 103 to 104 and SEQ ID NO: 109 to 112.

BRIEF DESCRIPTION OF DRAWINGS

FIG. 1 shows schematic diagram outlining the nested (RT-) PCR based strategy used. The (RT-) PCR strategy for amplifying the mouse rearranged/expressed $V_H$ genes using genomic DNA from splenocytes (A) and total RNA from splenocytes or hybridomas (B) as starting template is shown.

DETAILED DESCRIPTION OF THE INVENTION

Figure 2A:
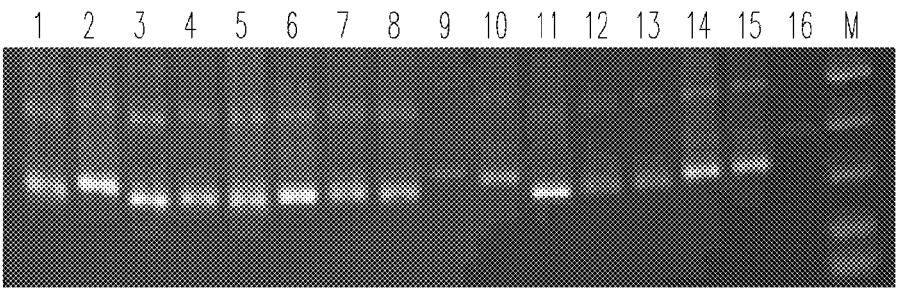
FIG. 2 shows PCR amplification of V gene families from mouse splenocyte genomic DNA. PCR products obtained for individual $V_H$ (A), $V_\kappa$ (B) and $V_\lambda$ (C) gene families (or genes where the family has only one member) using primers having nucleotide sequence as set in SEQ ID NO: 1-112. The name of the $V_H$, $V_\kappa$ and $V_\lambda$ gene family is indicated. '½' in (C) denotes $V_\lambda 1$ and $V_\lambda 2$ genes; M, molecular weight marker (766, 500, 300, 150 and 50 bp).

The present invention discloses a nested PCR targeted to mouse rearranged/expressed immunoglobulin V gene family comprising $V_H$, $V_\kappa$, $V_\lambda$, $J_H$, $J_\kappa$, $J_\lambda$, $C_H$, $C_\kappa$ and $C_\lambda$ genes assay B cell repertoire and/or isotyping antibody producing cells from a sample. The nested PCR disclosed in the present invention is a specific and sensitive tool for amplification of mouse rearranged/expressed immunoglobulin V gene family.

The present invention provides a novel highly specific and sensitive universal nested PCR primer set for (RT-) PCR capable of potentially amplifying the rearranged/expressed $V_H$ and $V_L$ gene belonging to any mouse immunoglobulin V gene family from a single or a small number of B cells.

A database of germline immunoglobulin sequences was used to design 112 primers (SEQ ID NO:1-12) for a nested (RT-) PCR based strategy to cover all $V_H$, $V_L$, $J_H$, $J_L$, $C_H$ and $C_L$ gene families/genes from C57BL/6 and BALB/c mice. 93.7% of the primers had 4-fold or less, while 71.4% had no degeneracy. The proportions of germline V genes to which the primers bind with no, up to 1 and up to 2 mismatches are 59.7%, 84.1% and 94.9%, respectively.

We have validated the broad V gene family coverage provided by this set of 112 (SEQ ID NO: 1-112) primers by amplifying the rearranged/expressed V genes from splenocytes and a panel of 38 hybridomas under conditions where pooled primers and genomic DNA or total RNA was used as starting template.

We experimentally confirmed the V gene family-specific nature of the designed primers for 6 randomly selected $V_H$, 6 $V_\kappa$ and 2 $V_\lambda$ families. Cocktail of constant region specific primers allowed efficient RT-PCR amplification of IgM, IgG, IgA, Igκ and Igλ isotypes.

The primers disclosed in the present invention permitted RT-PCR amplification of IgM, IgG, IgA, Igκ and Igλ isotypes. The broad V gene family coverage and single cell level sensitivity offered by our primer set can be taken advantage of to study B cell repertoire by single cell RT-PCR. Analysis at the single cell level avoids the bias that may be introduced into V region cDNA library construction by the presence of highly variable levels of mRNA in different cells (Wang and Stollar, 2000).

The primers disclosed in the present invention cover all V genes, with the exception of a few pseudogenes. The V gene primers are compatible with all the J- and C region primers. As a consequence of the high sensitivity of the assay, RT-PCR or genomic PCR can be done directly with small number of hybridoma or B cells thus bypassing the need and effort to isolate total RNA or genomic DNA. The amount of RT-PCR amplified product obtained from hybridoma cells is sufficient for sequencing with the $C_H$ or $C_L$ internal primer thus doing away with the cloning step. Due to the high sensitivity and specificity, and broad V gene family coverage, the designed primers have the potential to be used for studying various mouse B cell subsets, to follow progress of B cell lymphomas and test the heterogeneity of B cell populations at the single cell level (Jacob et al., 1991a; Jacob et al., 1991b; Kim and Berek, 2007; Tiller et al., 2007). It would now be possible to amplify and sequence V genes from small numbers of B cells recovered from lesions or during the course of infection. This will facilitate the study of anti-infectious disease Ab repertoire.

The present invention discloses a functional set of nested primers having nucleotide sequence as set forth in SEQ ID NO: 1-112 that cover all mouse $V_H$, $V_\kappa$, $V_\lambda$, $J_H$, $J_\kappa$, $J_\lambda$, $C_H$, $C_\kappa$, and $C_\lambda$ genes. The primer set and the PCR strategy permits amplification of essentially all rearranged $V_H$ and $V_L$ gene families from C57BL/6 and BALB/c mice from either genomic DNA or transcript in a highly sensitive and V gene specific manner. The primers exhibit low degeneracy and cross-family priming, and amplify the rearranged V genes in an isotype independent fashion. The design principle outlined here can be extended to Ig gene systems from other species, other members of the Ig super family such as the T cell receptor and in designing primers for complex multigene families.

The present invention describes that amplification of the rearranged $V_H$ and $V_L$ genes from a mixture of hybridomas occurred in a representative manner. We successfully amplified the expressed/rearranged $V_H$ and $V_L$ gene from a single hybridoma cell by RT-PCR, and 10-15 microdissected B cells from immunohistochemically stained splenic sections by genomic PCR.

The present invention discloses novel universal nested primers for (RT-) PCR amplification of the mouse rearranged/expressed $V_H$ and $V_L$ genes. The versatile and comprehensive set of nested primers disclosed in the present invention are indispensable for applications where sample or template quantity is limiting (as in the case of microdissected or biopsy material) and where broad V gene family coverage is required. These primer sets facilitate study of B cell subsets, ontogeny and B cell lymphomas.

We demonstrated that the amplification of the rearranged $V_H$ and $V_L$ genes from a mixture of hybridomas occurred in a representative manner. We successfully amplified the expressed/rearranged $V_H$ and $V_L$ gene from a single hybridoma cell by RT-PCR, and 10-15 microdissected B cells from immunohistochemically stained splenic sections by genomic PCR.

V gene family-specific nature of the primers (SEQ ID NO: 1-112) disclosed in the present invention is experimentally confirmed for 6 randomly selected $V_H$, 6 $V_\kappa$ and 2 $V_\lambda$ families. Cocktail of constant region specific primers allowed efficient RT-PCR amplification of IgM, IgG, IgA, Igκ and Igλ isotypes.

Most but not all V gene family specific primers designed allow amplification of full-length V genes. These nested primers permit PCR amplification of rearranged V genes belonging to all $V_H$ and $V_L$ gene families from splenocyte genomic DNA. The V gene family-specific nature of the primers was experimentally confirmed for randomly selected 6 $V_H$ and 6 $V_\kappa$ families, and all $V_\lambda$ genes. The broad V gene family coverage of the primer set was experimentally validated by amplifying the rearranged/expressed $V_H$ and $V_L$ genes from splenocytes and a panel of 38 hybridomas under conditions where primer mixes and genomic DNA or total RNA was used as starting template. We observed no or low-level cross-family priming. Pooled constant region specific primers allowed efficient RT-PCR amplification of H and L chain isotypes. The expressed $V_H$ and $V_L$ genes belonging to different V gene families RT-PCR amplified from a mixture of hybridomas in a representative manner.

This, first of its kind, comprehensive set of highly sensitive and specific nested primers that provide broad V gene family coverage will open up new avenues and opportunities to study various aspects of mouse B cell biology.

Designing Universal Nested PCR Primers for Amplification of Mouse Rearranged/Expressed $V_H$ and $V_L$ Genes In order to develop highly specific and sensitive PCR that can potentially amplify mouse rearranged/expressed $V_H$ and $V_L$ gene belonging to any V gene family we adopted a nested strategy. The primers used for first and second (nested) round of PCR are referred to as external and internal primers, respectively. The leader ($L_H$), variable ($V_H$), diversity ($D_H$), joining ($J_H$), constant ($C_H$) and complementary determining region 3 (HCDR3) regions of the Ig H chain are indicated. In most cases, the binding site for the 5' external and internal primer is located in the leader and framework region 1, respectively. The instances were both 5' external and internal primer hybridizes to the framework region 1 are indicated in Tables 1 and 2. The arrows pointing to the right and left indicate the orientation of the sense and antisense primers, respectively. The antisense primer (RT) used for first strand cDNA synthesis binds in the $C_H1$ region. The strategy (not shown) used for (RT-) PCR amplification of the rearranged/expressed $V_\kappa$ and $V_\lambda$ genes was essentially identical to the one used for the H chain (FIG. 1).

Mouse germline Ig sequences were downloaded from international ImMunoGeneTics information system and IgBLAST databases for designing the primers. We focused our primer designing effort on the two most commonly used inbred strains of mice, namely C57BL/6 and BALB/c. The sequences were grouped in 16 $V_H$ (350 members), 19 $V_\kappa$ (164 members), 3 $V_\lambda$ (3 members), 1 $J_H$ (4 members), 1 $J_\kappa$ (5 members), and 1 $J_\lambda$ (5 members) families according to the IMGT nomenclature. MacVector software was used to analyze each Ig gene family. Based on the nucleotide sequence alignment of individual families, we designed a set of external and internal primers targeting conserved motifs in the leader, framework region 1, joining and constant regions of H and L chain genes (FIG. 1).

The 112 oligonucleotide primers (SEQ ID NO: 1-112) designed for amplifying the mouse rearranged/expressed Ig genes are summarized in Tables 1-3. A panel of 17 $V_H$ external, 17 $V_H$ internal, 1 $J_H$ external and 2 $J_H$ internal primers were designed for the H chain. In addition, 5 $C_H$ external, 5 $C_H$ internal and 5 $C_H$ primers for reverse transcribing the Ig transcript ($RTC_H$) were designed for the H chain isotypes IgM, IgG, IgA, IgE and IgD (Table 1). For κ L chain, a panel of 19 $V_\kappa$ external, 20 $V_\kappa$ internal, 1 $J_\kappa$ external, 1 $J_\kappa$ internal, 1 $C_\kappa$ external, 1 $C_\kappa$ internal and 1 $RTC_\kappa$, primers were designed (Table 2). Likewise, for λ L chain, a panel of 3 $V_\lambda$ external, 3 $V_\lambda$ internal, 2 $J_\lambda$ external, 2 $J_\lambda$ internal, 1 $C_\lambda$ external, 2 $C_\lambda$ internal and 1 $RTC_\lambda$ primers were designed (Table 3). The designed primer pairs were tested for their specificity and compatibility using PCR simulating software, Amplify 3. The total number of genes in any given Ig family, sequence of the oligonucleotide primer, position of the primer binding sites of the external and internal primers, fold degeneracy and the number of genes in a given Ig family with 0, 1, 2, 3 or 4 mismatches relative to the primer sequence are detailed in Tables 1-3. The 5' external and internal primers bind in the leader and framework region 1, respectively, in the case of 8 out of 16 (50%) $V_H$ families, 18 out of 19 (94.7%) $V_\kappa$ families and all $V_\lambda$ genes (100%). In the remaining V gene families, both 5' external and internal primers hybridize to framework region 1. Primers designed for 7 out of 16 (43.7%) $V_H$ families, 14 out of 19 (73.7%) $V_\kappa$ families and all $V_\lambda$ genes (100%) allow amplification of full-length V genes.

The primers were designed to cover functional and non-functional (pseudogene) germline Ig genes. In some instances, certain pseudogenes could not be included in designing the primers either because the sequences were too divergent or the available sequence was truncated and did not cover the primer binding site(s) (Tables 1-3). In most cases, single external and internal primers were sufficient to cover all the members of an Ig gene family. However, there were some exceptions. Two external and internal primers were required to cover the 193 genes belonging to the $V_H1$ family. Two internal primers were required to cover the $J_H$ gene segments. Two $C_H$ external and internal primers were required to cover all the IgG isotypes. The instances where 2 primers were required to cover all the members of a L chain family are: 2 $V_\kappa1$ family internal primers, 2 $J_\lambda$ external primers, 2 $J_\lambda$ internal primers and 2 $C_\lambda$ internal primers. On the other hand, single external and internal primers were sufficient to cover $V_\lambda1$ and $V_\lambda2$ genes.

The primers were 17 to 22 nucleotide long with a $T_m$ of 56° C. to 64° C., with the exception of the primers used for the first strand cDNA synthesis, which were 16 to 17 nucleotide long ($T_m=48°$ C. to 50° C.). Majority (71.4%) of the designed primers had no degeneracy and 93.7% percentage had 4-fold or less degeneracy. The proportions of germline Ig genes to which the primers bind with no mismatch, up to 1 mismatch and up to 2 mismatches are 59.7%, 84.1% and 94.9%, respectively. More than half (59%) of the primers ended with a 'G' or 'C' at their 3' end, favouring the extension by the thermostable polymerase and consequently, the efficiency of amplification.

The 5' primers, designed to work for both DNA and RNA templates, are located in the leader or the framework one region (FIG. 1). For genomic PCR, the 3' primers are designed to hybridize to the J region. For amplifying the expressed V gene using RNA as a template, the 3' primers anneal to the $C_H1$ and $C_L$ domain of the H and L chain genes, respectively. The choice between using the J or C region primer depends on the intended application i.e. genomic PCR versus RT-PCR.

Figure 2B:
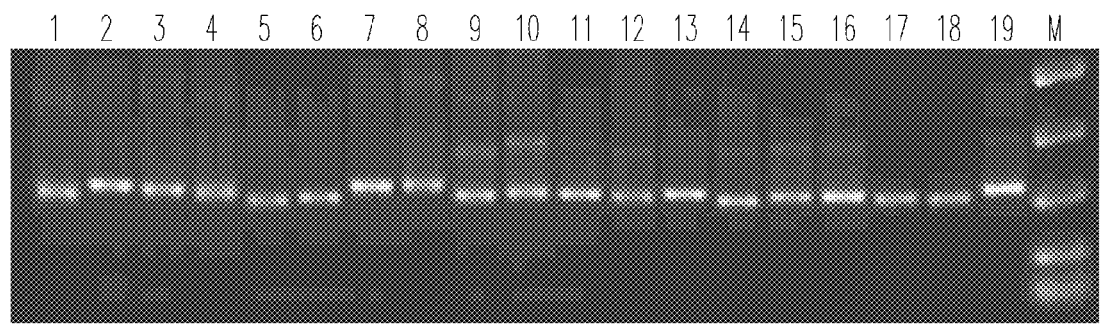
Figure 2C:
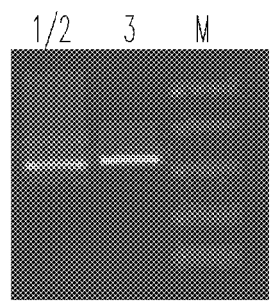

Designed Nested PCR Primers Allow Amplification of the Rearranged V Gene from all $V_H$ and $V_L$ Gene Families A nested PCR strategy was employed for amplifying the rearranged $V_H$ and $V_L$ genes using genomic DNA from splenocytes (FIG. 1A). Primer pairs corresponding to each V gene family were tested individually. In total 16 $V_H$, 19 $V_\kappa$ and 2 $V_\lambda$ PCRs were set up using V gene family targeting primers in conjunction with the corresponding J region primer(s). Amplified products of the expected size (~350 bp) were obtained for 15 $V_H$, 19 $V_\kappa$ and 2 $V_\lambda$ gene families (FIG. 2). The PCR products showed minor variation in size across families, depending upon the position of the 5' internal primer binding site. The size of the PCR product obtained was generally consistent with the position of the binding site of the 5' internal primer of the corresponding V gene family (Tables 1-3). It is highly unlikely that these bands were the result of PCR contamination. This was confirmed by cloning and sequencing the PCR product of 6 randomly selected $V_H$ and $V_\kappa$ families, and all $V_\lambda$ genes.

Figure 3:
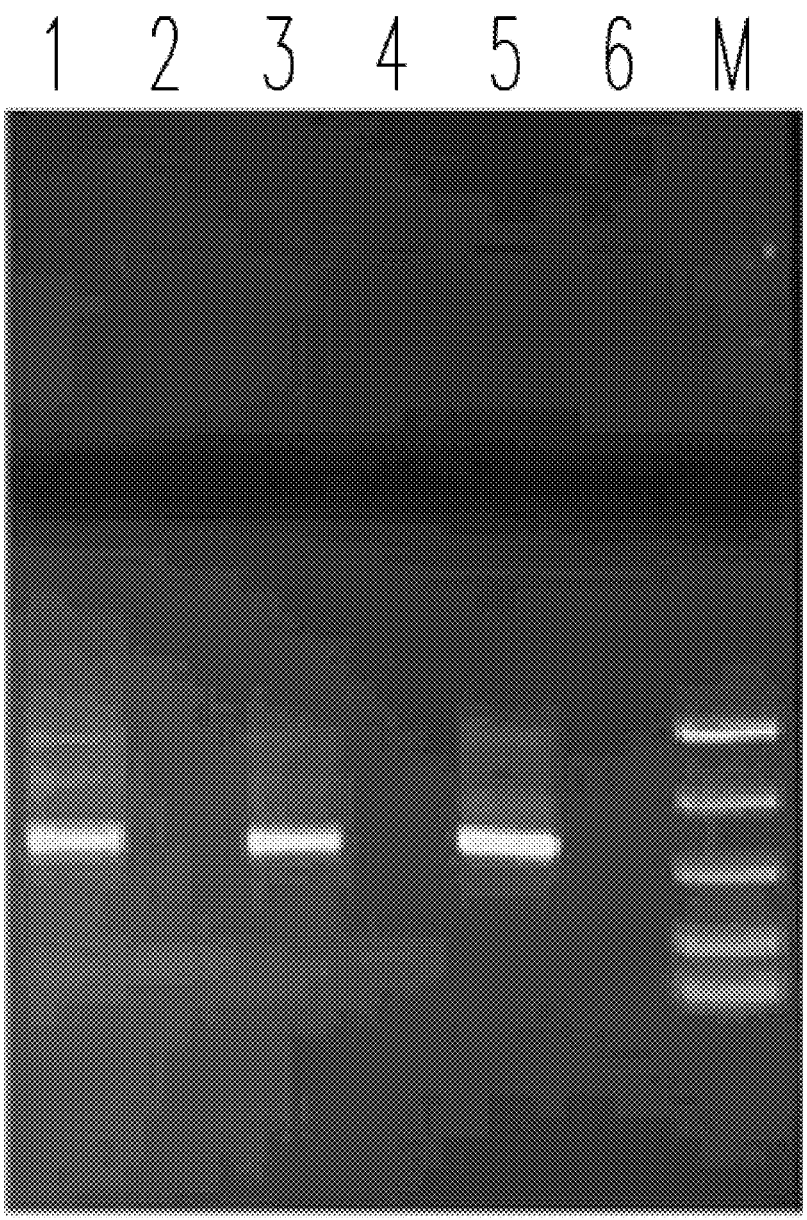
FIG. 3 shows amplification of the rearranged V genes using pooled primers. Nested PCR was performed to amplify the rearranged V genes using genomic DNA from mouse splenocytes and 3 separate cocktails comprising of primers targeting all $V_H$ (lane 1), $V_\kappa$ (lane 3) and $V_\lambda$ (lane 5) gene families. The corresponding negative controls (water only) are in lanes 2, 4 and 6, respectively; M, molecular weight marker (766, 500, 300, 150 and 50 bp).

We tested the compatibility of the primers (SEQ ID NO: 1-112) by setting up 3 separate PCRs with pooled mixes comprising of primers directed at all H-, all κ- and all λ-gene families (FIG. 3, lanes 1, 3 and 5, respectively). The PCRs once again yielded single bands (with no primer dimers) indicating that the primers did not interfere with each other during the amplification process even when present as a complex primer mix. The negative control (water only) did not yield any band (FIG. 3, lanes 2, 4 and 6).

Our amplification strategy requires a second (nested) round of PCR but the additional effort is compensated by the enhanced specificity and sensitivity. Although the primers were designed for amplifying the rearranged/expressed Ig genes from C57BL/6 and BALB/c, they are highly likely to work efficiently for other mouse strains as well, owing to sufficiently high degree of sequence conservation across mice strains. This is illustrated by the amplification of all the $V_H$ and $V_L$ gene families from CBA/J mouse, the recently reported $V_H16$ family being an exception (FIG. 2).

Designed Nested PCR Primers are V Gene Family-Specific

To test whether our primers were V gene family-specific we randomly selected 6 V gene families ($V_H1$, $V_H5$, $V_H8$, $V_\kappa3$, $V_\kappa4$ and $V_\kappa13$) that had 12 to 193 members, 6 V gene families ($V_H4$, $V_H11$, $V_H15$, $V_\kappa11$, $V_\kappa14$ and $V_\kappa17$) that had 2 to 8 members and the 3 $V_\lambda$ genes (Tables 1-3). We constructed independent libraries using V gene family-specific primers and splenocyte genomic DNA as template for 6 $V_H$ and 6 $V_\kappa$ gene families, and the 3 $V_\lambda$ genes. Two independent libraries were generated for the $V_\lambda$ genes, one for $V_\lambda1$ and $V_\lambda2$ genes, and a second one for $V_\lambda3$ gene. The nucleotide sequence was determined for 4-6 recombinants recovered from each library. Sequence analysis revealed that in all instances the rearranged V genes recovered were functional and belonged to the targeted V gene family (Table 4). Analysis of rearranged V genes recovered from libraries generated for V gene families that had 12 or more members showed a broad V gene usage pattern, $V_\kappa13$ family being an exception. $V_\kappa13$ has 18 members of which 15 are pseudogenes. Eleven pseudogenes were not included in designing the primers as their sequences were too divergent (Table 2). gm33, one of the 3 functional members of the $V_\kappa13$ gene family, was observed in the 4 independent $V_\kappa J_\kappa$ rearrangements recovered from the library.

V gene usage was found to be limited in V gene families with 1 to 4 members ($V_H4$, $V_H11$, $V_H15$, $V_\kappa11$, $V_\kappa17$, $V_\lambda\frac{1}{2}$ and $V_\lambda3$) (Table 4). We observed that all the independent rearrangements recovered from $V_H4$, $V_H11$, $V_H15$, and $V_\kappa11$ gene family-specific libraries utilized a single V gene belonging to the corresponding V gene family.

All the 4 independent rearrangements recovered from the $V_H4$ family-specific library utilized X24.2.50 gene. X24.2.50 gene reported (from C57BL/6 mice) in the IMGT and IgBLAST databases has an in-frame stop codon in framework region 2. All the 4 independent rearrangements lack this in-frame stop codon. It is highly unlikely that the nonsense codon somatically mutated to a sense codon in all 4 rearrangements. Our data thus suggests that the homolog of X24.2.50 gene in CBA/J mice, from which our V gene libraries were constructed, is a functional $V_H$ gene.

These data confirm that our primers are V gene family-specific. We have demonstrated this for V gene families with 12 or more members as well as V gene families that have only a couple of members.

Efficient Amplification and Rapid Identification of $V_H$ and $V_L$ Gene Family Expressed in Hybridomas The designed primers were used to amplify the expressed $V_H$ and $V_L$ genes from total RNA isolated from a collection of 38 unique IgM and IgG expressing hybridomas available in our laboratory. We successfully amplified the $V_H$ and $V_L$ genes expressed in from all 38 hybridomas using the primer set (SEQ ID NO: 1-112) and PCR strategy. The RT-PCR amplified product was sequenced using the appropriate $C_H$, $C_\kappa$ or $C_\lambda$ internal primer. Sequence comparison and V gene family assignment for the expressed H and L chain genes was done using IMGT and IgBLAST databases.

Once the identity of the family to which the expressed V gene belongs has been established, one can, if need be, use the corresponding 5' internal primer to sequence the second strand of the purified PCR product. Nucleotide sequence analysis of the $V_H$ genes expressed in the 38 hybridomas indicated that they belonged to 8 out of the 16 $V_H$ families. In addition to the major $V_H$ gene families, $V_H1$, $V_H5$ and $V_H9$, the primers amplified $V_H2$, $V_H3$, $V_H7$, $V_H10$ and $V_H14$ minor $V_H$ gene families. A family with less than 5% of the total number of genes present in our $V_H$ database was classified as a minor family.

Similarly, the $V_L$ genes expressed in the 38 hybridomas were sequenced and analyzed. Thirty seven of the 38 hybridomas expressed κ L chain. The expressed $V_\kappa$ genes belong to 14 out of the 19 $V_\kappa$ families. They are $V_\kappa1$, $V_\kappa2$, $V_\kappa3$, $V_\kappa4$, $V_\kappa5$, $V_\kappa6$, $V_\kappa8$, $V_\kappa9$, $V_\kappa10$, $V_\kappa12$, $V_\kappa13$, $V_\kappa15$, $V_\kappa18$ and $V_\kappa19$ families. Of these $V_\kappa5$, $V_\kappa9$, $V_\kappa10$, $V_\kappa15$, $V_\kappa18$ and $V_\kappa19$ families have 6 (3.7%) or fewer members. The lone λ L chain expressing hybridoma rearranged $V_\lambda2$ and $J_\lambda2$ gene segments. These data demonstrate that our Ig primers are capable of specifically amplifying the expressed $V_H$, $V_\kappa$ and $V_\lambda$ gene families that are very diverse in sequence and size. V gene families that were not represented in the panel of hybridomas may not be involved in the immune response to the immunizing Ag or we may not have sampled enough clones to observe them.

Primers Allow Broad V Gene Family Coverage Under Conditions where Primer Mixes and Splenocytes were Used PCR amplification of the rearranged/expressed $V_H$ and $V_\lambda$ genes using genomic DNA and total RNA from splenocytes as starting template was carried out, the rearranged $V_H$ and $V_\lambda$ genes from splenocyte genomic DNA were amplified using pooled primers that target all $V_H$ families and all $V_\lambda$ genes, respectively (SEQ ID NO:1-112, Tables 1-3). The $V_H$ and $V_\lambda$ PCR products were cloned and the recombinants recovered from the two libraries were sequenced. The nucleotide sequence was analyzed to identify the germline V gene and family utilized. $V_H$ and $V_\lambda$ cDNA libraries were constructed using pooled constant region, and $V_H$ and $V_\lambda$ primer mixes. The summary of the nucleotide sequence analysis is presented in Table 6. The 119 rearranged $V_H$ genomic clones analyzed represented 38 unique $V_H$ genes belonging to 12 of the 15 $V_H$ families present in CBA/J mice. Most of the remaining 81 rearranged $V_H$ genomic clones were independent VDJ rearrangements of the 38 unique $V_H$ genes. In some instances, we observed 2 or more identical copies of the same genomic clone. Of the 53 $V_H$ cDNA clones analyzed 22 were unique and 31 were either independent rearrangements involving the 22 unique $V_H$ genes or identical copies of cDNA clones (Table 6). The 22 unique cDNAs belonged to 10 $V_H$ families. Four $V_H$ genes were found as genomic and cDNA clones. $V_H$ genomic and cDNA clones, when put together, covered 13 $V_H$ families and 56 unique $V_H$ genes. For the λ light chain, all the 3 $V_\lambda$ genes i.e. VL1, VL2 and VLx, were recovered as genomic and cDNA clones. In conclusion, $V_H$ and $V_\lambda$ primer set (SEQ ID NO: 1-112) disclosed in the present invention provides broad V gene family coverage under conditions where primer mixes and splenocytes were used.

Cross-Family Priming and Mutations Introduced by PCR Primers

Use of degenerate primers and primer cocktails (e.g. pooled $V_H$ or $V_L$ primer mixes) can allow broad V family/member coverage. The potential disadvantage of using degenerate primers or primer mixes is that it can lead to introduction of mutation(s) in the annealing region as result of (a) degenerate bases present in the primer, (b) cross-family priming and (c) authentic somatic mutation(s) present in the primer binding site may get replaced by the corresponding nucleotide in the annealing primer during PCR. We studied cross-family priming in the $V_\kappa$ and $V_H$ families. We RT-PCR amplified and cloned the expressed $V_\kappa$ gene from 37 hybridomas using pooled $V_\kappa$ primers. These hybridomas represent 14 of the 19 $V_\kappa$ families and the number of hybridomas that belong to a given $V_\kappa$ gene family ranged from 1 to 7. The nucleotide sequences from the hybridomas were analyzed to identify the $V_\kappa$ internal primer that amplified the expressed $V_\kappa$ gene. In 31 of the 37 (83.8%) hybridomas analyzed, the $V_\kappa$ internal primer used and the amplified $V_\kappa$ gene belonged to the same family indicating low cross-$V_\kappa$ gene family priming and high degree of specificity of the primers. Of the 5 $V_\kappa 1$ gene family expressing hybridomas, 2 were primed by $V_\kappa 4$ primer. None of the 7 $V_\kappa 4$ expressing hybridomas were primed by a $V_\kappa 1$ primer. We also observed cross-$V_\kappa$ gene family priming in 3 other cases.

The issue of cross-family priming was also examined for the $V_H$ gene families. This was addressed in two ways. One, by analyzing the recombinants recovered from a library generated using pooled $V_H$ primers and splenocyte genomic DNA. A $V_H$ cDNA library was generated in parallel using pooled $V_H$ primers and total RNA from splenocytes. The clones recovered from the $V_H$ genomic and cDNA libraries (listed in Table 6) were analyzed to identify the $V_H$ internal primer that amplified the expressed $V_H$ gene and family to which the expressed $V_H$ gene belongs. In the 38 $V_H$ genomic and 22 cDNA clones analyzed, the $V_H$ internal primer used and the amplified $V_H$ gene belonged to the same family with no exceptions. Thus, the $V_H$ primers exhibited high $V_H$ family specificity and no cross-family priming. We avoided the difficulties that can arise as a result of using degenerate primers and primer mixes by limiting the sequence analysis to the region internal to the 5' and 3' internal primer.

Pooled Constant Region Specific Primers Allow Efficient RT-PCR Amplification of H and L Chain Isotypes The use of IgH, Igκ and Igλ specific constant region primers for reverse transcription allows subsequent amplification of only IgH, Igκ and Igλ chain, respectively. In situations where the isotype of the expressed H and L chain is not known e.g. when small numbers of B cells or single B cells are used, the $C_H$ and $C_L$ constant region primers have to be pooled. To test this, total RNA isolated from splenocytes was reverse transcribed using pooled IgM, IgG, IgA, Igκ and Igλ specific constant region primers (listed in Tables 1-3). Equal amount of cDNA was used as template for setting up 6 independent nested PCRs for amplifying IgM, IgG, IgA, Igκ and Igλ V gene transcripts. The IgG transcripts were covered in two separate reactions, one for IgG3 and the second one for the remaining IgG isotypes. The expressed H, κ and λ chain were amplified using the corresponding pooled $V_H$, $V_\kappa$ and $V_\lambda$ primer cocktail, respectively. The second round PCR products were cloned and recombinants recovered from the resultant 6 cDNA isotype specific libraries were sequenced. Analysis of the recombinants revealed that each of the 6 libraries were indeed specific for the intended isotype. No non-specific amplification was observed in any of the isotype specific libraries. Thus, our pooled constant region primers allow efficient and specific RT-PCR amplification of IgM, IgG, IgA, Igκ and Igλ isotypes.

Expressed $V_H$ and $V_L$ Genes Belonging to Different V Gene Families can be Amplified from Pooled Hybridomas in a Representative Manner Since we use pooled $V_H$ and $V_L$ primer sets to amplify the rearranged/expressed $V_H$ and $V_L$ genes, it was important to test for any possible preferential binding of individual primers to selected rearranged/expressed V genes as it can complicate B cell repertoire analysis. We analyzed this by pooling equal amounts of total RNA from 5 previously characterized IgM expressing hybridomas. The $V_H$ genes expressed in these hybridomas belonged to $V_H 1$, $V_H 2$, $V_H 3$, $V_H 7$ and $V_H 14$ gene families. The expressed $V_L$ genes present belonged to $V_\kappa 5$, $V_\kappa 9$, $V_\kappa 12$, $V_\kappa 18$ and $V_\lambda 2$ gene families. We constructed $V_H$ and $V_L$ gene specific cDNA libraries starting with total RNA pooled from hybridomas as template, and cocktails of all $V_H$ and $V_L$ primers. The plasmid DNA recovered from the recombinants obtained from the $V_H$ and $V_L$ cDNA libraries were digested with restriction enzyme(s) that can distinguish the $V_H$ and $V_L$ genes expressed in the hybridomas pooled in the experiment. Using restriction profiling, we recovered the expected 5 expressed $V_H$ and 4 $V_L$ genes from the $V_H$ and $V_L$ cDNA libraries, respectively. The 5 expressed $V_H$ and 4 $V_\kappa$ genes identified by restriction digestion were confirmed by sequencing. In addition to these 4 expressed $V_\kappa$ genes, we found a rearranged $V_\kappa 1$ family member that was rendered non-functional because of a frameshift mutation in framework region 1 and the presence of a nonsense codon in framework region 2. This $V_\kappa J_\kappa$ gene most likely represents a non-productively rearranged allele present in one of the 5 hybridomas. These data suggests that the primer set (SEQ ID NO: 1-112) and RT-PCR strategy amplifies the expressed $V_H$ and $V_L$ genes from a mixture of hybridoma cells in a representative manner.

Nested RT-PCR Amplification of the Expressed V Genes is Highly Sensitive

Figure 4A:
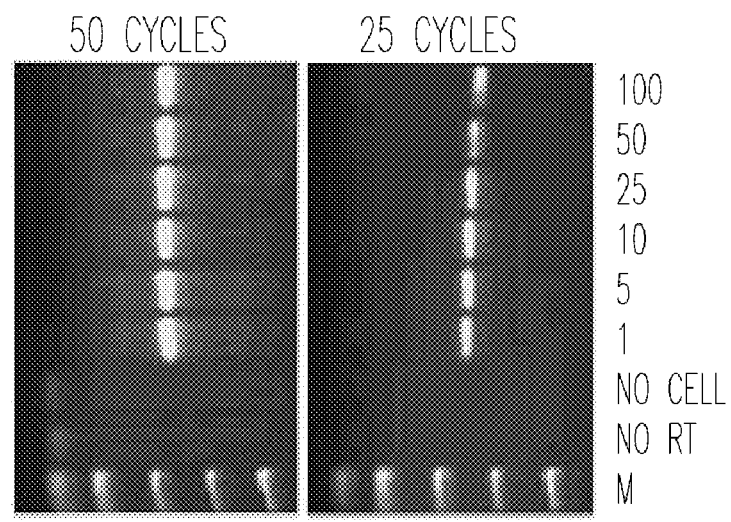
FIG. 4 shows determination of detection limit of the designed primers using RT-PCR. The expressed $V_\kappa$ gene was amplified using $V_\kappa$ pooled primer mix, $C_\kappa$ primer and decreasing numbers of hybridoma cells (100 to 1 cell) (A). The corresponding primers used for the expressed $V_H$ gene were pooled $V_H$ and $C_\mu$ primers (B). 'No cell' and 'no reverse transcriptase' negative controls are shown; M, molecular weight marker (766, 500, 300, 150 and 50 bp).
Figure 4B:
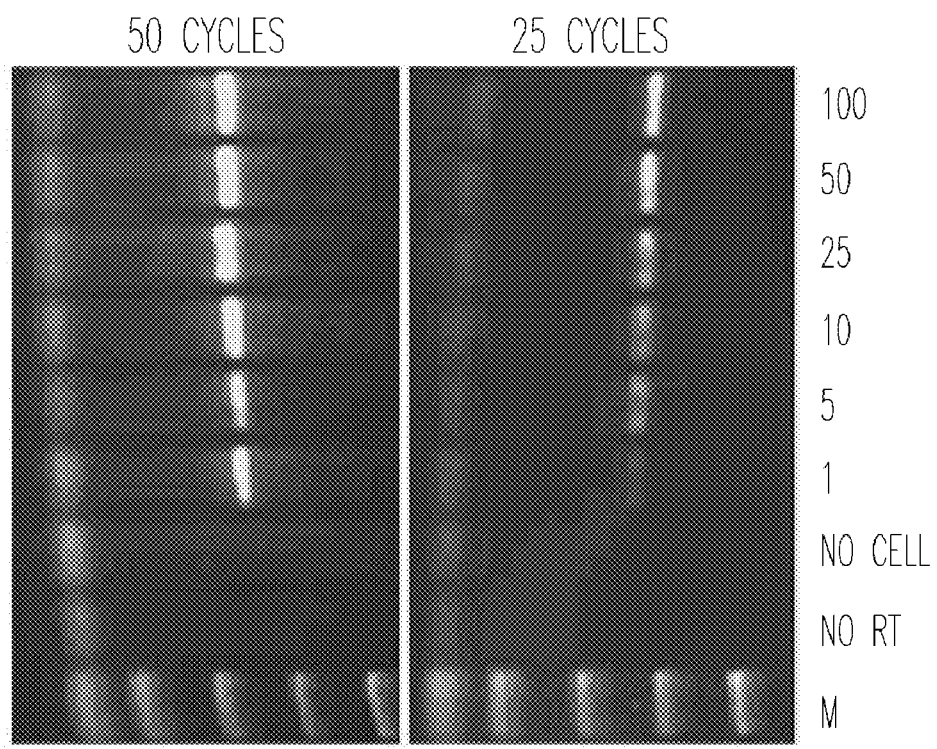

After establishing the broad coverage and specificity of the designed primer set, we set out to determine the sensitivity of our nested (RT-) PCR strategy and primers. We first tested the detection limit of our amplification strategy by performing RT-PCR for the expressed $V_\kappa$ genes using a dilution series ranging from 100 to 1 hybridoma cell (FIG. 4A). Using pooled $V_\kappa$ primer mix and $C_\kappa$ primer, we were able to readily amplify the expressed κ L chain gene from a single hybridoma cell by RT-PCR. Similarly, we amplified the expressed $V_H$ gene from a single hybridoma cell using pooled $V_H$ and $C_\mu$ primers. Although we were able to detect a faint $V_H$ band from a single cell template input (FIG. 4B) but the yield was not sufficient for sequence analysis. We went on to test the effect of increasing the number of PCR amplification cycles for 25 per round of PCR to 50 on the detection limit of the expressed $V_H$ gene. Increasing the PCR cycles from 25 to 50 permitted easy detection of the amplified $V_H$ product from a single hybridoma cell (FIG. 4B, lower panel). Increasing the numbers of PCR cycles increased the yield of the $V_\kappa$ RT-PCR product further. We did not detect any product when hybridoma cell or reverse transcriptase was omitted from the reaction mix (FIG. 4).

Figure 5A:
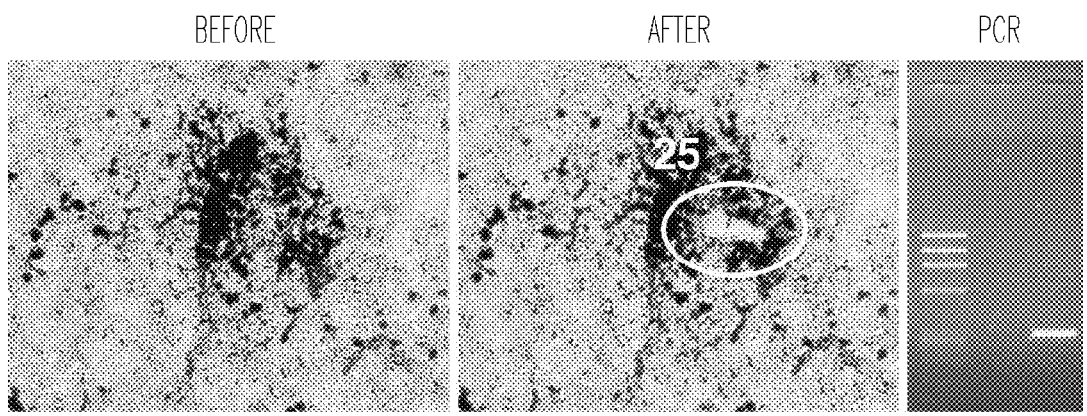
FIG. 5 shows PCR amplification of rearranged $V_H$ and $V_\kappa$ genes from immunohistochemically stained B cells microdissected from splenic sections from naïve BALB/c mice.
Figure 5B:
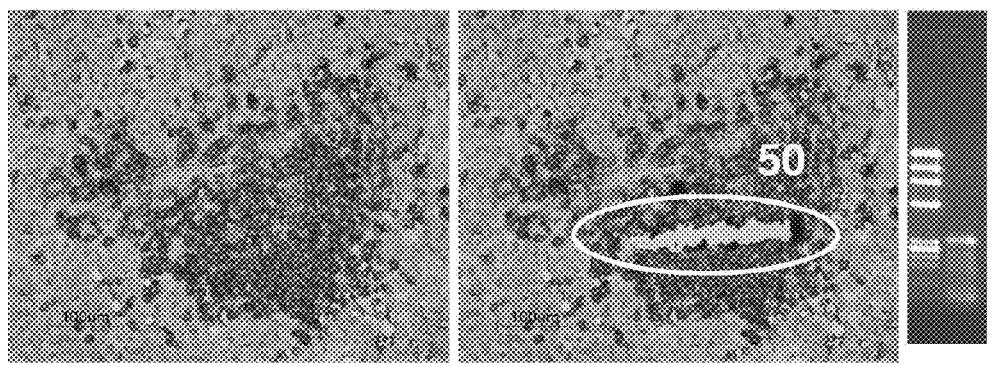
Figure 5C:
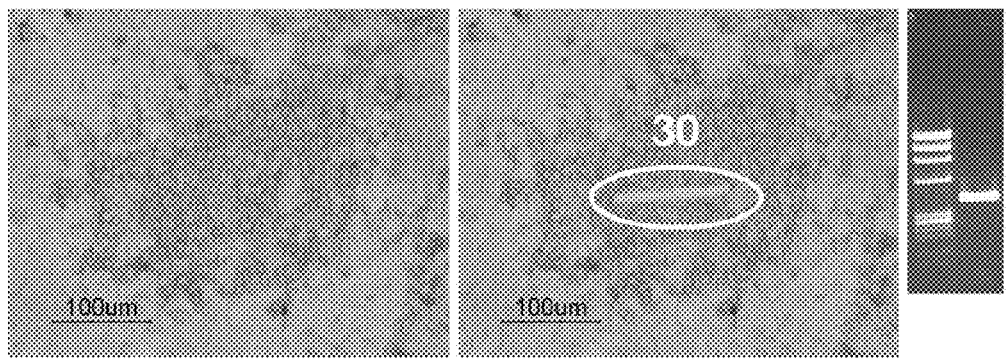

In addition to the hybridomas, we tested the ability of the designed primers to amplify the rearranged $V_H$ and $V_L$ genes from immunohistochemically stained B220[+] B cells microdissected from splenic sections from naïve BALB/c mice. Using genomic DNA based nested PCR strategy and separately pooled $V_H$ and $V_\kappa$ primer mixes we were able to amplify the rearranged $V_H$ and $V_\kappa$ genes from 10 to 15 microdissected B220[+] B cells (FIG. 5). On rare occasions we were able to amplify the rearranged V genes from 4 to 5 microdissected B cells but the amplification was not very consistent and reproducible (data not shown). B220[+] B cells were microdissected from splenic sections using a hydraulic micromanipulator. The rearranged $V_H$ (A) and $V_\kappa$ (B) genes were amplified using $V_H$ and $V_\kappa$ primer mixes, respectively. The images of the stained section taken before and after the B cells were microdissected are shown in the left most and middle columns. The estimated number of B cells microdissected (encircled) from the splenic section is indicated. The amplified rearranged $V_H$ (H) and $V_\kappa$ (κ) gene product obtained using the genomic DNA based nested PCR strategy along with the negative control (buffer only, C) is shown in the right most column (FIG. 5).

In accordance with the present invention in one embodiment there is provided a set of oligonucleotides for assaying rearrangement of immunoglobulin genes for identifying clonality of cells, cancer cells, hypermutation in immunoglobulin gene, antibody isotype producing cell and/or assaying B cell repertoire in a sample, wherein nucleotide sequences of said oligonucleotides are as set forth in SEQ ID NO: 1 to 112.

In one embodiment there is provided the set of oligonucleotides for assaying rearrangement of immunoglobulin genes for identifying clonality of cells, cancer cells, hypermutation in immunoglobulin gene, antibody isotype producing cell and/or assaying B cell repertoire in a sample, wherein nucleotide sequences of said oligonucleotides are as set forth in SEQ ID NO: 1 to 112, wherein said immunoglobin genes are $V_H$, $V_\kappa$ and $V_\lambda$, $J_H$, $J_\kappa$, $J_\lambda$, $C_H$, $C_\kappa$ and $C_\lambda$.

In one embodiment there is provided the set of oligonucleotides for assaying rearrangement of immunoglobulin genes for identifying clonality of cells, cancer cells, hypermutation in immunoglobulin gene, antibody isotype producing cell and/or assaying B cell repertoire in a sample, wherein nucleotide sequences of said oligonucleotides are as set forth in SEQ ID NO: 1 to 112, wherein said antibody is selected from the group consisting of immunoglobulin heavy chain isotypes IgG, IgM, IgA, IgE, and IgD; and light chain isotypes κ and λ.

In another embodiment of the present invention there is provided a set of oligonucleotides for assaying rearrangement of immunoglobulin genes for identifying clonality of cells, cancer cells, hypermutation in immunoglobulin gene, antibody isotype producing cell and/or assaying B cell repertoire in a sample, wherein nucleotide sequences of said set of oligonucleotides is selected from the group consisting of set 1: SEQ ID NO: 1 to 37, SEQ ID NO: 55 to 95 and SEQ ID NO: 99 to 108; and set 44: SEQ ID NO: 1 to 34, SEQ ID NO: 38 to 93, SEQ ID NO: 96 to 104 and SEQ ID NO: 109 to 112.

In another embodiment of the present invention there is provided a set of oligonucleotides for assaying rearrangement of immunoglobulin genes for identifying clonality of cells, cancer cells, hypermutation in immunoglobulin gene, antibody isotype producing cell and/or assaying B cell repertoire in a sample, wherein nucleotide sequences of said set of oligonucleotides is selected from the group consisting of set 1: SEQ ID NO: 1 to 37, SEQ ID NO: 55 to 95 and SEQ ID NO: 99 to 108; and set 44: SEQ ID NO: 1 to 34, SEQ ID NO: 38 to 93, SEQ ID NO: 96 to 104 and SEQ ID NO: 109 to 112, wherein said immunoglobin genes are $V_H$, $V_\kappa$ and $V_\lambda$ genes.

One embodiment of the present invention provides a set of oligonucleotides for assaying rearrangement of immunoglobulin genes for identifying clonality of cells, cancer cells, hypermutation in immunoglobulin gene, antibody isotype producing cell and/or assaying B cell repertoire in a sample, wherein nucleotide sequences of said set of oligonucleotides is selected from the group consisting of set 2: SEQ ID NO: 1 to 37, set 3: SEQ ID NO: 1 to 4 and SEQ ID NO: 35-37, set 4: SEQ ID NO: 5 to 6 and SEQ ID NO: 35 to 37, set 5: SEQ ID NO: 7 to 8 and SEQ ID NO: 35-37, set 6: SEQ ID NO: 9 to 10 and SEQ ID NO: 35-37, set 7: SEQ ID NO: 11 to 12 and SEQ ID NO: 35-37; set 8: SEQ ID NO: 13 to 14 and SEQ ID NO: 35-37; set 9: SEQ ID NO: 15 to 16 and SEQ ID NO: 35-37; set 10: SEQ ID NO: 17 to 18 and SEQ ID NO: 35-37; set 11: SEQ ID NO: 19 to 20 and SEQ ID NO: 35-37; set 12: SEQ ID NO: 21-22 and SEQ ID NO: 35-37; set 13: SEQ ID NO: 23 to 24 and SEQ ID NO: 35-37; set 14: SEQ ID NO: 25 to 26 and SEQ ID NO: 35-37; set 15: SEQ ID NO: 27 to 28 and SEQ ID NO: 35-37; set 16: SEQ ID NO: 29 to 30 and SEQ ID NO: 35-37; set 17: SEQ ID NO: 31 to 32 and SEQ ID NO: 35-37; and set 18: SEQ ID NO: 33-37.

Another embodiment of the present invention provides the set of oligonucleotides for assaying rearrangement of immunoglobulin genes for identifying clonality of cells, cancer cells, hypermutation in immunoglobulin gene, antibody isotype producing cell and/or assaying B cell repertoire in a sample, wherein nucleotide sequences of said set of oligonucleotides is selected from the group consisting of set 2: SEQ ID NO: 1 to 37, set 3: SEQ ID NO: 1 to 4 and SEQ ID NO: 35-37, set 4: SEQ ID NO: 5 to 6 and SEQ ID NO: 35 to 37, set 5: SEQ ID NO: 7 to 8 and SEQ ID NO: 35-37, set 6: SEQ ID NO: 9 to 10 and SEQ ID NO: 35-37, set 7: SEQ ID NO: 11 to 12 and SEQ ID NO: 35-37; set 8: SEQ ID NO: 13 to 14 and SEQ ID NO: 35-37; set 9: SEQ ID NO: 15 to 16 and SEQ ID NO: 35-37; set 10: SEQ ID NO: 17 to 18 and SEQ ID NO: 35-37; set 1: SEQ ID NO:19 to 20 and SEQ ID NO: 35-37; set 12: SEQ ID NO: 21-22 and SEQ ID NO: 35-37; set 13: SEQ ID NO: 23 to 24 and SEQ ID NO: 35-37; set 14: SEQ ID NO: 25 to 26 and SEQ ID NO: 35-37; set 15: SEQ ID NO: 27 to 28 and SEQ ID NO: 29 to 30; set 16: SEQ ID NO: 29 to 30 and SEQ ID NO: 35-37; set 17: SEQ ID NO: 31 to 32 and SEQ ID NO: 35-37; and set 18: SEQ ID NO: 33-37, wherein said immunoglobin genes are $V_H$ genes.

Still another embodiment of the present invention provides a set of oligonucleotides for assaying rearrangement of immunoglobulin genes for identifying clonality of cells, cancer cells, hypermutation in immunoglobulin gene, antibody isotype producing cell and/or assaying B cell repertoire in a sample, wherein nucleotide sequences of said set of oligonucleotides are as set forth in set 19: SEQ ID NO: 55 to 95 and SEQ ID NO: 99 to 108.

Still another embodiment of the present invention provides the set of oligonucleotides for assaying rearrangement of immunoglobulin genes for identifying clonality of cells, cancer cells, hypermutation in immunoglobulin gene, antibody isotype producing cell and/or assaying B cell repertoire in a sample, wherein nucleotide sequences of said set of oligonucleotides are as set forth in set 19: SEQ ID NO: 55 to 95 and SEQ ID NO: 99 to 108, wherein said immunoglobin genes are $V_L$ genes.

Yet another embodiment of the present invention provides a set of oligonucleotides for assaying rearrangement of immunoglobulin genes for identifying clonality of cells, cancer cells, hypermutation in immunoglobulin gene, antibody isotype producing cell and/or assaying B cell repertoire in a sample, wherein nucleotide sequences of said set of oligonucleotides is selected from the group consisting of set 20: SEQ ID NO: 55 to 95; set 21: SEQ ID NO: 55 to 57 and SEQ ID NO: 94 to 95; set 22: SEQ ID NO: 58 to 59 and SEQ ID NO: 94 to 95; set 23: SEQ ID NO: 60 to 61 and SEQ ID NO: 94 to 95; set 24: SEQ ID NO: 62 to 63 and SEQ ID NO: 94 to 95; set 25: SEQ ID NO: 64 to 65 and SEQ ID NO: 94 to 95; set 26: SEQ ID NO: 66 to 67 and SEQ ID NO: 94 to 95; set 27: SEQ ID NO: 68 to 69 and SEQ ID NO: 94 to 95; set 28: SEQ ID NO: 70 to 71 and SEQ ID NO: 94 to 95; set 29: SEQ ID NO: 72 to 73 and SEQ ID NO: 94 to 95; set 30: SEQ ID NO: 74 to 75 and SEQ ID NO: 94 to 95; set 31: SEQ ID NO: 76 to 77 and SEQ ID NO: 94 to 95; set 32: SEQ ID NO: 78 to 79 and SEQ ID NO: 94 to 95; set 33: SEQ ID NO: 80 to 81 and SEQ ID NO: 94 to 95; set 34: SEQ ID NO: 82 to 83 and SEQ ID NO: 94 to 95; set 35: SEQ ID NO: 84 to 85 and SEQ ID NO: 94 to 95; set 36: SEQ ID NO: 86 to 87 and SEQ ID NO: 94 to 95; set 37: SEQ ID NO: 88 to 89 and SEQ ID NO: 94 to 95; set 38: SEQ ID NO: 90 to 91 and SEQ ID NO: 94 to 95; and set 39: SEQ ID NO: 92 to 95.

Yet another embodiment of the present invention provides the set of oligonucleotides for assaying rearrangement of immunoglobulin genes for identifying clonality of cells, cancer cells, hypermutation in immunoglobulin gene, antibody isotype producing cell and/or assaying B cell repertoire in a sample, wherein nucleotide sequences of said set of oligonucleotides is selected from the group consisting of set 20: SEQ ID NO: 55 to 95; set 21: SEQ ID NO: 55 to 57 and SEQ ID NO: 94 to 95; set 22: SEQ ID NO: 58 to 59 and SEQ ID NO: 94 to 95; set 23: SEQ ID NO: 60 to 61 and SEQ ID NO: 94 to 95; set 24: SEQ ID NO: 62 to 63 and SEQ ID NO: 94 to 95; set 25: SEQ ID NO: 64 to 65 and SEQ ID NO: 94 to 95; set 26: SEQ ID NO: 66 to 67 and SEQ ID NO: 94 to 95; set 27: SEQ ID NO: 68 to 69 and SEQ ID NO: 94 to 95; set 28: SEQ ID NO: 70 to 71 and SEQ ID NO: 94 to 95; set 29: SEQ ID NO: 72 to 73 and SEQ ID NO: 94 to 95; set 30: SEQ ID NO: 74 to 75 and SEQ ID NO: 94 to 95; set 31: SEQ ID NO: 76 to 77 and SEQ ID NO: 94 to 95; set 32: SEQ ID NO: 78 to 79 and SEQ ID NO: 94 to 95; set 33: SEQ ID NO: 80 to 81 and SEQ ID NO: 94 to 95; set 34: SEQ ID NO: 82 to 83 and SEQ ID NO: 94 to 95; set 35: SEQ ID NO: 84 to 85 and SEQ ID NO: 94 to 95; set 36: SEQ ID NO: 86 to 87 and SEQ ID NO: 94 to 95; set 37: SEQ ID NO: 88 to 89 and SEQ ID NO: 94 to 95; set 38: SEQ ID NO: 90 to 91 and SEQ ID NO: 94 to 95; and set 39: SEQ ID NO: 92 to 95, wherein said immunoglobin genes are $V_\kappa$ genes.

Further embodiment of the present invention provides a set of oligonucleotides for assaying rearrangement of immunoglobulin genes for identifying clonality of cells, cancer cells, hypermutation in immunoglobulin gene, antibody isotype producing cell and/or assaying B cell repertoire in a sample, wherein nucleotide sequences of said set of oligonucleotides is selected from the group consisting of set 40: SEQ ID NO: 99 to 108; set 41: SEQ ID NO: 99 to 100 and SEQ ID NO: 105 to 108; set 42: SEQ ID NO: 101 to 102 and SEQ ID NO: 105 to 108; and set 43: SEQ ID NO: 103 to 108.

Further embodiment of the present invention provides the set of oligonucleotides for assaying rearrangement of immunoglobulin genes for identifying clonality of cells, cancer cells, hypermutation in immunoglobulin gene, antibody isotype producing cell and/or assaying B cell repertoire in a sample, wherein nucleotide sequences of said set of oligonucleotides is selected from the group consisting of set 40: SEQ ID NO: 99 to 108; set 41: SEQ ID NO: 99 to 100 and SEQ ID NO: 105 to 108; set 42: SEQ ID NO: 101 to 102 and SEQ ID NO: 105 to 108; and set 43: SEQ ID NO: 103 to 108, wherein said immunoglobin genes are $V_\lambda$ genes.

The present invention further provides a set of oligonucleotides for assaying rearrangement of immunoglobulin genes for identifying clonality of cells, cancer cells, hypermutation in immunoglobulin gene, antibody isotype producing cell and/or assaying B cell repertoire in a sample, wherein nucleotide sequences of said set of oligonucleotides is selected from the group consisting of set 45: SEQ ID NO: 1 to 34, SEQ ID NO: 38-54; set 46: SEQ ID NO: 1 to 34, SEQ ID NO: 38, SEQ ID NO: 43 to 44; set 47: SEQ ID NO: 1 to 34, SEQ ID NO: 39, SEQ ID NO: 45 to 48; set 48: SEQ ID NO: 1 to 34, SEQ ID NO: 40, SEQ ID NO: 49 to 50; set 49: SEQ ID NO: 1 to 34, SEQ ID NO: 41, SEQ ID NO: 51 to 52; set 50: SEQ ID NO: 1 to 34, SEQ ID NO: 42, SEQ ID NO: 53 to 54; set 51: SEQ ID NO: 1 to 4 and SEQ ID NO: 38 to 54; set 52: SEQ ID NO: 5 to 6 and SEQ ID NO: 38 to 54; set 53: SEQ ID NO: 7 to 8 and SEQ ID NO: 38 to 54; set 54: SEQ ID NO: 9 to 10 and SEQ ID NO: 38 to 54; set 55: SEQ ID NO: 11 to 12 and SEQ ID NO: 38 to 54; set 56: SEQ ID NO: 13 to 14 and SEQ ID NO: 38 to 54; set 57: SEQ ID NO: 15 to 16 and SEQ ID NO: 38 to 54; set 58: SEQ ID NO: 17 to 18 and SEQ ID NO: 38 to 54; set 59: SEQ ID NO: 19 to 20 and SEQ ID NO: 38 to 54; set 60: SEQ ID NO: 21 to 22 and SEQ ID NO: 38 to 54; set 61: SEQ ID NO: 23 to 24 and SEQ ID NO: 38 to 54; set 62: SEQ ID NO: 25 to 26 and SEQ ID NO: 38 to 54; set 63: SEQ ID NO: 27 to 28 and SEQ ID NO: 38 to 54; set 64: SEQ ID NO: 29 to 30 and SEQ ID NO: 38 to 54; set 65: SEQ ID NO: 31 to 32 and SEQ ID NO: 38 to 54; and set 66: SEQ ID NO: 33 to 34 and SEQ ID NO: 38 to 54, wherein said immunoglobin genes are expressed heavy chain genes.

Another embodiment of the present invention provides a set of oligonucleotides for assaying rearrangement of immunoglobulin genes for identifying clonality of cells, cancer cells, hypermutation in immunoglobulin gene, antibody isotype producing cell and/or assaying B cell repertoire in a sample, wherein nucleotide sequences of said set of oligonucleotides is selected from the group consisting of set 67: SEQ ID NO: 55 to 93; SEQ ID NO: 96 to 104 and SEQ ID NO: 109 to 112; set 68: SEQ ID NO: 55 to 93 and SEQ ID NO: 96 to 98, set 69: SEQ ID NO: 55 to 57 and SEQ ID NO: 96 to 98, set 70: SEQ ID NO: 58 to 59 and SEQ ID NO: 96 to 98, set 71: SEQ ID NO: 60 to 61 and SEQ ID NO: 96 to 98, set 72: SEQ ID NO: 62 to 63 and SEQ ID NO: 96 to 98, set 73: SEQ ID NO: 64 to 65 and SEQ ID NO: 96 to 98, set 74: SEQ ID NO: 66 to 67 and SEQ ID NO: 96 to 98, set 75: SEQ ID NO: 68 to 69 and SEQ ID NO: 96 to 98, set 76: SEQ ID NO: 70 to 71 and SEQ ID NO: 96 to 98, set 77: SEQ ID NO: 72 to 73 and SEQ ID NO: 96 to 98, set 78: SEQ ID NO: 74 to 75 and SEQ ID NO: 96 to 98, set 79: SEQ ID NO: 76 to 77 and SEQ ID NO: 96 to 98, set 80: SEQ ID NO: 78 to 79 and SEQ ID NO: 96 to 98; set 81: SEQ ID NO: 80 to 81 and SEQ ID NO: 96 to 98; set 82: SEQ ID NO: 82 to 83 and SEQ ID NO: 96 to 98; set 83: SEQ ID NO: 84 to 85 and SEQ ID NO: 96 to 98; set 84: SEQ ID NO: 86 to 87 and SEQ ID NO: 96 to 98; set 85: SEQ ID NO: 88 to 89 and SEQ ID NO: 96 to 98; set 86: SEQ ID NO: 90 to 91 and SEQ ID NO: 96 to 98; set 87: SEQ ID NO: 92 to 93 and SEQ ID NO: 96 to 98; set 88: SEQ ID NO: 99 to 104 and SEQ ID NO: 109 to 112; set 89: SEQ ID NO: 99 to 100 and SEQ ID NO: 109 to 112; set 90: SEQ ID NO: 101 to 102 and SEQ ID NO: 109 to 112; and set 91: SEQ ID NO: 103 to 104 and SEQ ID NO: 109 to 112.

Another embodiment of the present invention provides a set of oligonucleotides for assaying rearrangement of immunoglobulin genes for identifying clonality of cells, cancer cells, hypermutation in immunoglobulin gene, antibody isotype producing cell and/or assaying B cell repertoire in a sample, wherein nucleotide sequences of said set of oligonucleotides is selected from the group consisting of set 67:

SEQ ID NO: 55 to 93; SEQ ID NO: 96 to 104 and SEQ ID NO: 109 to 112; set 68: SEQ ID NO: 55 to 93 and SEQ ID NO: 96 to 98, set 69: SEQ ID NO: 55 to 57 and SEQ ID NO: 96 to 98, set 70: SEQ ID NO: 58 to 59 and SEQ ID NO: 96 to 98, set 71: SEQ ID NO: 60 to 61 and SEQ ID NO: 96 to 98, set 72: SEQ ID NO: 62 to 63 and SEQ ID NO: 96 to 98, set 73: SEQ ID NO: 64 to 65 and SEQ ID NO: 96 to 98, set 74: SEQ ID NO: 66 to 67 and SEQ ID NO: 96 to 98, set 75: SEQ ID NO: 68 to 69 and SEQ ID NO: 96 to 98, set 76: SEQ ID NO: 70 to 71 and SEQ ID NO: 96 to 98, set 77: SEQ ID NO: 72 to 73 and SEQ ID NO: 96 to 98, set 78: SEQ ID NO: 74 to 75 and SEQ ID NO: 96 to 98, set 79: SEQ ID NO: 76 to 77 and SEQ ID NO: 96 to 98, set 80: SEQ ID NO: 78 to 79 and SEQ ID NO: 96 to 98; set 81: SEQ ID NO: 80 to 81 and SEQ ID NO: 96 to 98; set 82: SEQ ID NO: 82 to 83 and SEQ ID NO: 96 to 98; set 83: SEQ ID NO: 84 to 85 and SEQ ID NO: 96 to 98; set 84: SEQ ID NO: 86 to 87 and SEQ ID NO: 96 to 98; set 85: SEQ ID NO: 88 to 89 and SEQ ID NO: 96 to 98; set 86: SEQ ID NO: 90 to 91 and SEQ ID NO: 96 to 98; set 87: SEQ ID NO: 92 to 93 and SEQ ID NO: 96 to 98; set 88: SEQ ID NO: 99 to 104 and SEQ ID NO: 109 to 112; set 89: SEQ ID NO: 99 to 100 and SEQ ID NO: 109 to 112; set 90: SEQ ID NO: 101 to 102 and SEQ ID NO: 109 to 112; and set 91: SEQ ID NO: 103 to 104 and SEQ ID NO: 109 to 112, wherein said immunoglobin genes are expressed light chain genes.

In yet another embodiment there is provided a set of oligonucleotides for assaying rearrangement of immunoglobulin genes for identifying clonality of cells, cancer cells, hypermutation in immunoglobulin gene, antibody isotype producing cell and/or assaying B cell repertoire in a sample, wherein nucleotide sequences of said oligonucleotides are as set forth in SEQ ID NO: 1 to 54.

In yet another embodiment there is provided a set of oligonucleotides for assaying rearrangement of immunoglobulin genes for identifying clonality of cells, cancer cells, hypermutation in immunoglobulin gene, antibody isotype producing cell and/or assaying B cell repertoire in a sample, wherein nucleotide sequences of said oligonucleotides are as set forth in SEQ ID NO: 1 to 54, wherein said immunoglobin genes are $V_H$, $J_H$, and $C_H$ In yet another embodiment there is provided a set of oligonucleotides for assaying rearrangement of immunoglobulin genes for identifying clonality of cells, cancer cells, hypermutation in immunoglobulin gene, antibody isotype producing cell and/or assaying B cell repertoire in a sample, wherein nucleotide sequences of said oligonucleotides are as set forth in SEQ ID NO: 55 to 98.

In yet another embodiment there is provided a set of oligonucleotides for assaying rearrangement of immunoglobulin genes for identifying clonality of cells, cancer cells, hypermutation in immunoglobulin gene, antibody isotype producing cell and/or assaying B cell repertoire in a sample, wherein nucleotide sequences of said oligonucleotides are as set forth in SEQ ID NO: 55 to 98, wherein said immunoglobin genes are $V_\kappa$, $J_\kappa$, and $C_\kappa$ gene.

In yet another embodiment there is provided a set of oligonucleotides for assaying rearrangement of immunoglobulin genes for identifying clonality of cells, cancer cells, hypermutation in immunoglobulin gene, antibody isotype producing cell and/or assaying B cell repertoire in a sample, wherein nucleotide sequences of said oligonucleotides are as set forth in SEQ ID NO: 98 to 112.

In yet another embodiment there is provided a set of oligonucleotides for assaying rearrangement of immunoglobulin genes for identifying clonality of cells, cancer cells, hypermutation in immunoglobulin gene, antibody isotype producing cell and/or assaying B cell repertoire in a sample, wherein nucleotide sequences of said oligonucleotides are as set forth in SEQ ID NO: 98 to 112, wherein said immunoglobin genes are $V_\lambda$, $J_\lambda$, and $C_\lambda$ gene.

The set of oligonucleotides as disclosed in the present invention are useful for detection of cancer, wherein the cancer is B cell lymphoma. One embodiment provides a hybridoma cell for identifying clonality of the cells.

Further embodiment of the present invention provides a process of assaying rearrangement of immunoglobulin genes for identifying clonality of cells, cancer cells, hypermutation in immunoglobulin gene, antibody isotype producing cell and/or assaying B cell repertoire in a sample using the set of oligonucleotides as set forth in SEQ ID NO: 1-112.

The present invention also provides a process of assaying rearrangement of immunoglobulin genes for identifying clonality of cells, cancer cells, hypermutation in immunoglobulin gene, antibody isotype producing cell and/or assaying B cell repertoire in a sample; the process comprises providing a sample; providing a first set of oligonucleotides as set forth in SEQ ID NO: 1, SEQ ID NO: 2, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 55, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 99, SEQ ID NO: 101, SEQ ID NO: 103, SEQ ID NO: 105 and SEQ ID NO: 106; performing a first round of polymerase chain reaction to obtain first product; performing second round of polymerase chain reaction using said first product and oligonucleotide as set forth in SEQ ID No. 3, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 37, SEQ ID NO: 56, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 100, SEQ ID NO: 102, SEQ ID NO: 104, SEQ ID NO: 107 and SEQ ID NO: 108; and detecting presence of an amplified product.

In another embodiment of the present invention there is provided a process of assaying rearrangement of immunoglobulin genes for identifying clonality of cells, cancer cells, hypermutation in immunoglobulin gene, antibody isotype producing cell and/or assaying B cell repertoire in a sample; the process comprises providing a sample; providing a first set of oligonucleotides as set forth in SEQ ID NO: 1, SEQ ID NO: 2, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 55, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 99, SEQ ID NO: 101, SEQ ID NO: 103, SEQ ID NO: 105 and SEQ ID NO: 106; performing a first round of polymerase chain reaction to obtain first product; performing second round of polymerase chain reaction using said first product and oligonucleotide as set forth in SEQ ID No. 3, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: SEQ ID NO: 26, SEQ ID NO: 28, SEQ ID NO: 30, SEQ ID NO: 32, SEQ ID NO: 34, SEQ ID NO: 44, SEQ ID NO: 47, SEQ ID NO: 48, SEQ ID NO: 50, SEQ ID NO: 52 and SEQ ID NO: 54; and detecting presence of an amplified product.

Yet another embodiment of the present invention relates to cancer, wherein said cancer is B cell lymphoma.

Yet another embodiment of the present invention relates to cell, wherein said cell is a hybridoma cell.

Yet another embodiment of the present invention relates to wherein said sample is a B cell.

Further there is provided a process for constructing library of polynucleotides encoding immunoglobulin genes, the process comprises amplifying immunoglobulin genes using the oligonucleotide sequences as set forth in SEQ ID NO: 1-112 to obtain amplified product; cloning said amplified product in an expression vector to obtain a recombinant expression vector; and transforming said recombinant expression vector in a host cell.

One embodiment of the present invention provides a prokaryotic expression vector.

Another embodiment of the present invention provides a host cell wherein the host cell is *E. coli*.

In addition the present invention a kit for assaying rearrangement of immunoglobulin genes for identifying clonality of cells, cancer cells, hypermutation in immunoglobulin gene, antibody isotype producing cell and/or assaying B cell repertoire in a sample, wherein said kit comprises nucleotide sequences of said oligonucleotides are as set forth in SEQ ID NO: 1 to 112.

In another embodiment of the present invention there is provided a kit for assaying rearrangement of immunoglobulin genes for identifying clonality of cells, cancer cells, hypermutation in immunoglobulin gene, antibody isotype producing cell and/or assaying B cell repertoire in a sample, wherein said kit comprises at least one set of oligonucleotides selected from the group consisting of set 1: SEQ ID NO: 1 to 37, SEQ ID NO: 55 to 95 and SEQ ID NO: 99 to 108; and set 44: SEQ ID NO: 1 to 34, SEQ ID NO: 38 to 93, SEQ ID NO: 96 to 104 and SEQ ID NO: 109 to 112.

In still another embodiment of the present invention there is provided a kit for assaying rearrangement of immunoglobulin genes for identifying clonality of cells, cancer cells, hypermutation in immunoglobulin gene, antibody isotype producing cell and/or assaying B cell repertoire in a sample, wherein said kit comprises at least one set of oligonucleotides selected from the group consisting of set 2: SEQ ID NO: 1 to 37, set 3: SEQ ID NO: 1 to 4 and SEQ ID NO: 35-37, set 4: SEQ ID NO: 5 to 6 and SEQ ID NO: 35 to 37, set 5: SEQ ID NO: 7 to 8 and SEQ ID NO: 35-37, set 6: SEQ ID NO: 9 to 10 and SEQ ID NO: 35-37, set 7: SEQ ID NO: 11 to 12 and SEQ ID NO: 35-37; set 8: SEQ ID NO: 13 to 14 and SEQ ID NO: 35-37; set 9: SEQ ID NO: 15 to 16 and SEQ ID NO: 35-37; set 10: SEQ ID NO: 17 to 18 and SEQ ID NO: 35-37; set 11: SEQ ID NO: 19 to 20 and SEQ ID NO: 35-37; set 12: SEQ ID NO: 21-22 and SEQ ID NO: 35-37; set 13: SEQ ID NO: 23 to 24 and SEQ ID NO: 35-37; set 14: SEQ ID NO: 25 to 26 and SEQ ID NO: 35-37; set 15: SEQ ID NO: 27 to 28 and SEQ ID NO: 29 to 30; set 16: SEQ ID NO: 29 to 30 and SEQ ID NO: 35-37; set 17: SEQ ID NO: 31 to 32 and SEQ ID NO: 35-37; and set 18: SEQ ID NO: 33-37.

In still yet another embodiment of the present invention there is provided a kit for assaying rearrangement of immunoglobulin genes for identifying clonality of cells, cancer cells, hypermutation in immunoglobulin gene, antibody isotype producing cell and/or assaying B cell repertoire in a sample, wherein said kit comprises set 19: SEQ ID NO: 55 to 95 and SEQ ID NO: 99 to 108.

In further embodiment of the present invention there is provided a A kit for assaying rearrangement of immunoglobulin genes for identifying clonality of cells, cancer cells, hypermutation in immunoglobulin gene, antibody isotype producing cell and/or assaying B cell repertoire in a sample, wherein said kit comprises at least one set of oligonucleotides selected from the group consisting of set 20: SEQ ID NO: 55 to 95; set 21: SEQ ID NO: 55 to 57 and SEQ ID NO: 94 to 95; set 22: SEQ ID NO: 58 to 59 and SEQ ID NO: 94 to 95; set 23: SEQ ID NO: 60 to 61 and SEQ ID NO: 94 to 95; set 24: SEQ ID NO: 62 to 63 and SEQ ID NO: 94 to 95; set 25: SEQ ID NO: 64 to 65 and SEQ ID NO: 94 to 95; set 26: SEQ ID NO: 66 to 67 and SEQ ID NO: 94 to 95; set 27: SEQ ID NO: 68 to 69 and SEQ ID NO: 94 to 95; set 28: SEQ ID NO: 70 to 71 and SEQ ID NO: 94 to 95; set 29: SEQ ID NO: 72 to 73 and SEQ ID NO: 94 to 95; set 30: SEQ ID NO: 74 to 75 and SEQ ID NO: 94 to 95; set 31: SEQ ID NO: 76 to 77 and SEQ ID NO: 94 to 95; set 32: SEQ ID NO: 78 to 79 and SEQ ID NO: 94 to 95; set 33: SEQ ID NO: 80 to 81 and SEQ ID NO: 94 to 95; set 34: SEQ ID NO: 82 to 83 and SEQ ID NO: 94 to 95; set 35: SEQ ID NO: 84 to 85 and SEQ ID NO: 94 to 95; set 36: SEQ ID NO: 86 to 87 and SEQ ID NO: 94 to 95; set 37: SEQ ID NO: 88 to 89 and SEQ ID NO: 94 to 95; set 38: SEQ ID NO: 90 to 91 and SEQ ID NO: 94 to 95; and set 39: SEQ ID NO: 92 to 95.

The present invention also provides a kit for assaying rearrangement of immunoglobulin genes for identifying clonality of cells, cancer cells, hypermutation in immunoglobulin gene, antibody isotype producing cell and/or assaying B cell repertoire in a sample, wherein said kit comprises at least one set of oligonucleotides selected from the group consisting of set 40: SEQ ID NO: 99 to 108; set 41: SEQ ID NO: 99 to 100 and SEQ ID NO: 105 to 108; set 42: SEQ ID NO: 101 to 102 and SEQ ID NO: 105 to 108; and set 43: SEQ ID NO: 103 to 108.

The present invention further provides a kit for assaying rearrangement of immunoglobulin genes for identifying clonality of cells, cancer cells, hypermutation in immunoglobulin gene, antibody isotype producing cell and/or assaying B cell repertoire in a sample, wherein said kit comprises at least one set of oligonucleotides selected from the group consisting of set 45: SEQ ID NO: 1 to 34, SEQ ID NO: 38-54; set 46: SEQ ID NO: 1 to 34, SEQ ID NO: 38, SEQ ID NO: 43 to 44; set 47: SEQ ID NO: 1 to 34, SEQ ID NO: 39, SEQ ID NO: 45 to 48; set 48: SEQ ID NO: 1 to 34, SEQ ID NO: 40, SEQ ID NO: 49 to 50; set 49: SEQ ID NO: 1 to 34, SEQ ID NO: 41, SEQ ID NO: 51 to 52; set 50: SEQ ID NO: 1 to 34, SEQ ID NO: 42, SEQ ID NO: 53 to 54; set 51: SEQ ID NO: 1 to 4 and SEQ ID NO: 38 to 54; set 52: SEQ ID NO: 5 to 6 and SEQ ID NO: 38 to 54; set 53: SEQ ID NO: 7 to 8 and SEQ ID NO: 38 to 54; set 54: SEQ ID NO: 9 to 10 and SEQ ID NO: 38 to 54; set 55: SEQ ID NO: 11 to 12 and SEQ ID NO: 38 to 54; set 56: SEQ ID NO: 13 to 14 and SEQ ID NO: 38 to 54; set 57: SEQ ID NO: 15 to 16 and SEQ ID NO: 38 to 54; set 58: SEQ ID NO: 17 to 18 and SEQ ID NO: 38 to 54; set 59: SEQ ID NO: 19 to 20 and SEQ ID NO: 38 to 54; set 60: SEQ ID NO: 21 to 22 and SEQ ID NO: 38 to 54; set 61: SEQ ID NO: 23 to 24 and SEQ ID NO: 38 to 54; set 62: SEQ ID NO: 25 to 26 and SEQ ID NO: 38 to 54; set 63: SEQ ID NO: 27 to 28 and SEQ ID NO: 38 to 54; set 64: SEQ ID NO: 29 to 30 and SEQ ID NO: 38 to 54; set 65: SEQ ID NO: 31 to 32 and SEQ ID NO: 38 to 54; and set 66: SEQ ID NO: 33 to 34 and SEQ ID NO:38 to 54.

The present invention further provides a kit for assaying rearrangement of immunoglobulin genes for identifying clonality of cells, cancer cells, hypermutation in immunoglobulin gene, antibody isotype producing cell and/or assaying B cell repertoire in a sample, wherein said kit comprises at least one set of oligonucleotides selected from the group consisting of set 67: SEQ ID NO: 55 to 93; SEQ ID NO: 96 to 104 and SEQ ID NO:109 to 112; set 68: SEQ ID NO: 55 to 93 and SEQ ID NO: 96 to 98, set 69: SEQ ID NO: 55 to 57 and SEQ ID NO: 96 to 98, set 70: SEQ ID NO: 58 to 59 and SEQ ID NO: 96 to 98, set 71: SEQ ID NO: 60 to 61 and SEQ ID NO: 96 to 98, set 72: SEQ ID NO: 62 to 63 and SEQ ID NO: 96 to 98, set 73: SEQ ID NO: 64 to 65 and SEQ ID NO: 96 to 98, set 74: SEQ ID NO: 66 to 67 and SEQ ID NO: 96 to 98, set 75: SEQ ID NO: 68 to 69 and SEQ ID NO: 96 to 98, set 76: SEQ ID NO: 70 to 71 and SEQ ID NO: 96 to 98, set 77: SEQ ID NO: 72 to 73 and SEQ ID NO: 96 to 98, set 78: SEQ ID NO: 74 to 75 and SEQ ID NO: 96 to 98, set 79: SEQ ID NO: 76 to 77 and SEQ ID NO: 96 to 98, set 80: SEQ ID NO: 78 to 79 and SEQ ID NO: 96 to 98; set 81: SEQ ID NO: 80 to 81 and SEQ ID NO: 96 to 98; set 82: SEQ ID NO: 82 to 83 and SEQ ID NO: 96 to 98; set 83: SEQ ID NO: 84 to 85 and SEQ ID NO: 96 to 98; set 84: SEQ ID NO: 86 to 87 and SEQ ID NO: 96 to 98; set 85: SEQ ID NO: 88 to 89 and SEQ ID NO: 96 to 98; set 86: SEQ ID NO: 90 to 91 and SEQ ID NO: 96 to 98; set 87: SEQ ID NO: 92 to 93 and SEQ ID NO: 96 to 98; set 88: SEQ ID NO: 99 to 104 and SEQ ID NO: 109 to 112; set 89: SEQ ID NO: 99 to 100 and SEQ ID NO: 109 to 112; set 90: SEQ ID NO: 101 to 102 and SEQ ID NO: 109 to 112; and set 91: SEQ ID NO: 103 to 104 and SEQ ID NO: 109 to 112.

EXAMPLES

It should be understood that the following examples described herein are for illustrative purposes only and that various modifications or changes in light will be suggested to persons skilled in the art and are to be included within the spirit and purview of this application and the scope of the appended claims.

Example 1

BALB/c and CBA/J inbred strains of mice were from The Jackson Laboratory, and were bred and maintained in the Small Animal Facility of the National Institute of Immunology. Mice used for experiments were 6 to 8 wk old. Approval from the Institutional Animal Ethics Committee was obtained for all experimental procedures involving animals.

PCR Amplification of Rearranged $V_H$ and $V_L$ Genes from Splenocyte Genomic DNA Genomic DNA was isolated from $2 \times 10^7$ splenocytes from CBA/J mice using a commercially available genomic DNA isolation kit following the manufacturer's instructions (Qiagen, Germany).

A nested PCR was performed for amplifying the rearranged $V_H$ and $V_L$ gene families. Family targeted PCRs were set up for each V gene family using H chain primer sets 3-18, κ L chain primer sets 21-39 and λ L chain primer sets 41-43 (Table 6) and genomic DNA from splenocytes. The 50 μl first round PCR mix consisted of 1× PCR buffer 1,200 μM dNTPs, 0.25 μM external 5' (V gene) and 3' (J region) primers each, and 2.5 U of AmpliTaq DNA polymerase (Applied Biosystems, USA).

Touchdown PCR was set up on a GeneAmp 2700 PCR System (Applied Biosystems, USA). The touchdown part of the PCR programme started with an initial denaturation step at 95° C. for 2 min. This was followed by denaturation at 94° C. for 1 min, annealing at 62° C. for 1 min and an extension at 72° C. for 1 min. The annealing temperature was decreased from 62° C. to 52° C. over 5 cycles at the rate of 2° C. per cycle. This was followed by 25 cycles consisting of denaturation at 94° C. for 1 min, annealing at 52° C. for 1 min and an extension at 72° C. for 1 min. A final extension step was carried out at 72° C. for 10 min. The composition of the reaction mixture and cycling parameters for the second round PCR were same as were used for the first round PCR except that 2 μl of the unpurified first round PCR product served as template for the second round PCR in place of splenocyte genomic DNA. The amplified products were analyzed on a 0.9% agarose gel.

The melting temperature ($T_m$ in ° C.) of the primers was calculated using the formula [(4× number of G or C nucleotides in the primer sequence)+(2× number of A or T nucleotides in the primer sequence)].

Primers for First round of PCR: $V_H1$ family SEQ ID NO. 1 and 2; $V_H2$ family SEQ ID NO. 5; $V_H3$ family SEQ ID NO. 7; $V_H4$ family SEQ ID NO. 9; $V_H5$ family SEQ ID NO. 11; $V_H6$ family SEQ ID NO. 13; $V_H7$ family SEQ ID NO. 15; $V_H8$ family SEQ ID NO. 17; $V_H9$ family SEQ ID NO. 19; $V_H10$ family SEQ ID NO. 21; $V_H11$ family SEQ ID NO. 23; $V_H12$ family SEQ ID NO. 25; $V_H13$ family SEQ ID NO. 27; $V_H14$ family SEQ ID NO. 29; $V_H15$ family SEQ ID NO. 31; $V_H16$ family SEQ ID NO. 33 in conjunction with SEQ ID NO. 35 plus $V_\kappa 1$ family SEQ ID NO. 55; $V_\kappa 2$ family SEQ ID NO. 58; $V_\kappa 3$ family SEQ ID NO. 60; $V_\kappa 4$ family SEQ ID NO. 62; $V_\kappa 5$ family SEQ ID NO. 64; $V_\kappa 6$ family SEQ ID NO. 66; $V_\kappa 7$ family SEQ ID NO. 68; $V_\kappa 8$ family SEQ ID NO. 70; $V_\kappa 9$ family SEQ ID NO. 72; $V_\kappa 10$ family SEQ ID NO. 74; $V_\kappa 11$ family SEQ ID NO. 76; $V_\kappa 12$ family SEQ ID NO. 78; $V_\kappa 13$ family SEQ ID NO. 80; $V_\kappa 14$ family SEQ ID NO. 82; $V_\kappa 15$ family SEQ ID NO. 84; $V_\kappa 16$ family SEQ ID NO. 86; $V_\kappa 17$ family SEQ ID NO. 88; $V_\kappa 18$ family SEQ ID NO. 90; $V_\kappa 19$ family SEQ ID NO. 92 in conjunction with SEQ ID NO 94 plus $V_\lambda 1$ and $V_\lambda 2$ SEQ ID NO. 99; $V_\lambda 3$ SEQ ID NO. 101; $V_\lambda 4, V_\lambda 5, V_\lambda 6, V_\lambda 7$ and $V_\lambda 8$ SEQ ID NO. 103 in conjunction with SEQ ID NO 105 and 106.

Primers for Second round of PCR: $V_H1$ family SEQ ID NO. 3 and 4; $V_H2$ family SEQ ID NO. 6; $V_H3$ family SEQ ID NO. 8; $V_H4$ family SEQ ID NO. 10; $V_H5$ family SEQ ID NO. 12; $V_H6$ family SEQ ID NO. 14; $V_H7$ family SEQ ID NO. 16; $V_H8$ family SEQ ID NO. 18; $V_H9$ family SEQ ID NO. 20; $V_H10$ family SEQ ID NO. 22; $V_H11$ family SEQ ID NO. 24; $V_H12$ family SEQ ID NO. 26; $V_H13$ family SEQ ID NO. 28; $V_H14$ family SEQ ID NO. 30; $V_H15$ family SEQ ID NO. 32; $V_H16$ family SEQ ID NO. 34 in conjunction with SEQ ID NO. 36 and 37 plus $V_\kappa 1$ family SEQ ID NO. 56 and 57; $V_\kappa 2$ family SEQ ID NO. 59; $V_\kappa 3$ family SEQ ID NO. 61; $V_\kappa 4$ family SEQ ID NO. 63; $V_\kappa 5$ family SEQ ID NO. 65; $V_\kappa 6$ family SEQ ID NO. 67; $V_\kappa 7$ family SEQ ID NO. 69; $V_\kappa 8$ family SEQ ID NO. 71; $V_\kappa 9$ family SEQ ID NO. 73; $V_\kappa 10$ family SEQ ID NO. 75; $V_\kappa 11$ family SEQ ID NO. 77; $V_\kappa 12$ family SEQ ID NO. 79; $V_\kappa 13$ family SEQ ID NO. 81; $V_\kappa 14$ family SEQ ID NO. 83; $V_\kappa 15$ family SEQ ID NO. 85; $V_\kappa 16$ family SEQ ID NO. 87; $V_\kappa 17$ family SEQ ID NO. 89; $V_\kappa 18$ family SEQ ID NO. 91; $V_\kappa 19$ family SEQ ID NO. 93 in conjunction with SEQ ID NO. 95 plus $V_\lambda 1$ and $V_\lambda 2$ SEQ ID NO. 100; V$_\lambda$3 SEQ ID NO. 102; V$_\lambda$4, V$_\lambda$5, V$_\lambda$6, V$_\lambda$7 and V$_\lambda$8 SEQ ID NO. 104 in conjunction with SEQ ID NO. 107 and 108.

Example 2

Construction of Rearranged V Gene Family-Specific Libraries

V gene family-specific primers and AmpliTaq DNA polymerase were used for amplifying 6 randomly selected V$_H$ (V$_H$1, V$_H$4, V$_H$5, V$_H$8, V$_H$11 and V$_H$15) and 6 V$_\kappa$ (V$_\kappa$3, V$_\kappa$4, V$_\kappa$11, V$_\kappa$13, V$_\kappa$14 and V$_\kappa$17) families and the 3 V$_\lambda$ (i.e. V$_\lambda$1, V$_\lambda$2 and V$_\lambda$3) genes using splenocyte genomic DNA from CBA/J mice. The PCR products obtained were purified using columns (RBC, Taiwan), cloned in TOPO-TA cloning vector (Invitrogen, USA) and transformed into *E. coli* strain XL1 Blue. Four to six recombinants from each V gene family-specific library were sequenced using an automated DNA sequencer. IMGT and IgBLAST databases were used to assign the germline gene segments utilized in the H and L chain. L chains with the same V$_L$ and J$_L$ gene segments were considered independent rearrangements if the V$_L$ to J$_L$ junctions were different. Rearranged V genes recovered from the libraries that had identical sequences were scored once.

The V$_H$1, V$_H$4, V$_H$5, V$_H$8, V$_H$11 and V$_H$15 families were amplified by nested PCR using primer sets 3, 6, 7, 10, 13 and 17, respectively. The V$_\kappa$3, V$_\kappa$4, V$_\kappa$11, V$_\kappa$13, V$_\kappa$14 and V$_\kappa$17 families were amplified by nested PCR using primer sets 23, 24, 31, 33, 34 and 37, respectively. The V$_\lambda$1 and V$_\lambda$2, and V$_\lambda$3 gene were amplified by nested PCR using primer sets 41 and 42, respectively (Table 6).

A library targeting the complete complement of immunoglobulin H and L chain rearrangements can be constructed using H chain primer sets 3-18, κ L chain primer sets 21-39 and λ L chain primer sets 41-43 (Table 6).

Example 3

Preparation of Pooled 5' External and Internal Primer Mixes

For applications where the identity of the rearranged/expressed V$_H$ and V$_L$ gene is not known, we used pooled primer mixes for (RT-) PCR. Separate external and internal primer mixes were made for V$_H$, V$_\kappa$ and V$_\lambda$ gene families. The V$_H$ external primer mix was prepared by pooling 17 external primers targeting all the V$_H$ gene families at a concentration of 2 μM each (Table 1). Similarly, the V$_H$ internal primer mix was prepared by pooling the 17 internal primers targeting all the V$_H$ gene families. Likewise, external and internal primer mixes were made for the V$_\kappa$ and V$_\lambda$ gene families (Table 2 and Table 3).

Pooled 5' external V$_H$ primer mix consisted of primers SEQ ID NO. 1, SEQ ID NO. 2, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31 and SEQ ID NO; 33.

Pooled 5' external V$_\kappa$ primer mix consisted of primers SEQ ID NO. 55, SEQ ID NO. 58, SEQ ID NO. 60, SEQ ID NO. 62, SEQ ID NO. 64, SEQ ID NO. 66, SEQ ID NO. 68, SEQ ID NO. 70, SEQ ID NO. 72, SEQ ID NO. 74, SEQ ID NO. 76, SEQ ID NO. 78, SEQ ID NO. 80, SEQ ID NO. 82, SEQ ID NO. 84, SEQ ID NO. 86, SEQ ID NO. 88, SEQ ID NO. 90 and SEQ ID NO: 92.

Pooled 5' external V$_\lambda$ primer mix consisted of primers SEQ ID NO. 99, SEQ ID NO. 101 and SEQ ID NO: 103.

Pooled 5' internal V$_H$ primer mix consisted of primers SEQ ID NO. 3, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32 and SEQ ID NO: 34.

Pooled 5' internal V$_\kappa$ primer mix consisted of primers SEQ ID NO. 56, SEQ ID NO. 57, SEQ ID NO. 59, SEQ ID NO. 61, SEQ ID NO. 63, SEQ ID NO. 65, SEQ ID NO. 67, SEQ ID NO. 69, SEQ ID NO. 71, SEQ ID NO. 73, SEQ ID NO. 75, SEQ ID NO. 77, SEQ ID NO. 79, SEQ ID NO. 81, SEQ ID NO. 83, SEQ ID NO. 85, SEQ ID NO. 87, SEQ ID NO. 89, SEQ ID NO. 91 and SEQ ID NO: 93.

Pooled 5' internal V$_\lambda$ primer mix consisted of primers SEQ ID NO. 100, SEQ ID NO. 102 and SEQ ID NO: 104.

Each 5' external and internal primer was used at a final concentration of 0.1 μM in the first and second round PCR. The same 5' primer mixes were used for amplifying the rearranged/expressed V$_H$ and V$_L$ genes from splenocyte genomic DNA or total RNA from splenocytes/hybridomas. The 3' were used at a final concentration of 0.25 μM as described above. J$_H$ or J$_L$ (for genomic DNA template) and C$_H$ or C$_L$ (for RNA template) primers were used as antisense primers.

For genomic DNA template:

J$_H$ external primer SEQ ID NO. 35; J$_H$ internal primers SEQ ID NO. 36 and SEQ ID NO. 37; J$_\kappa$ external primer SEQ ID NO. 94; J$_\kappa$ internal primer SEQ ID NO. 95; J$_\lambda$ external primer SEQ ID NO. 105 and SEQ ID NO. 106; J$_\lambda$ internal primer SEQ ID NO. 107 and SEQ ID NO. 108.

For RNA template:

Pooled 3' RT primer mix: SEQ ID NOs. 38-42, SEQ ID NO. 96 and SEQ ID NO. 109.

Pooled 3'C$_H$ external primer mix comprised of SEQ ID NO. 43, SEQ ID NO. 45, SEQ ID NO. 46, SEQ ID NO. 49, SEQ ID NO. 51 and SEQ ID NO. 53.

The 3' C$_\kappa$ external primer was SEQ ID NO. 97.

The 3' C$_\lambda$ external primer was SEQ ID NO. 110.

Pooled 3'C$_H$ internal primer mix comprised of SEQ ID NO. 44, SEQ ID NO. 47, SEQ ID NO. 48, SEQ ID NO. 50, SEQ ID NO. 52, and SEQ ID NO; 54.

The 3'C$_\kappa$ internal primer was SEQ ID NO. 98.

Pooled 3' C$_\lambda$ internal primer mix comprised of SEQ ID NO. 111 and SEQ ID NO: 112.

Example 4 cDNA Synthesis and PCR Amplification of Rearranged V$_H$ and V$_L$ Genes from Hybridomas Total RNA was extracted from $10^7$ hybridoma cells using a commercially available RNA isolation kit following the manufacturer's instructions (Qiagen, Germany). The purified RNA was quantitated spectrophotometrically. The first strand cDNA for the expressed H and L chain was synthesized using a commercially available RT-PCR kit (Applied Biosystems, USA) and C$_H$ or C$_L$ RT antisense primers (FIG. 1 and Tables 1-3, SEQ ID NO: 1-112). For H chain isotype specific RT primer was used for the reverse transcription reaction. The corresponding primers used for the κ and λ chains were RTC$_\kappa$ and RTC$_\lambda$, respectively. The 20 μl reverse transcription reaction mixture consisted of 1×PCR buffer II, 0.75 μM antisense primer, 10 mM dNTP mix, 5 mM MgCl$_2$, 1 U of RNase inhibitor, 50 U of MuLV reverse transcriptase (Applied Biosystems, USA) and 10 μg of total RNA. The reaction was performed at 42° C. for 1 h. Reverse transcriptase was inactivated by incubating at 99° C. for 5 min. Five μl of unpurified cDNA was used as a template for the first round PCR. The concentration of the components and cycling parameters were the same as described above for the genomic PCR except that PCR buffer 1, AmpliTaq DNA polymerase, and J region primers were replaced by Pfu Ultra Hotstart buffer, Pfu Ultra Hotstart DNA polymerase (Stratagene, USA) and C region primers, respectively. For experiments involving low copy templates e.g. small numbers of B cells or single B cells, Taq DNA polymerase was preferred over Pfu DNA polymerase because of its higher amplification efficiency.

Example 5

Determination of Detection Limit by RT-PCR

For determining the detection limit by RT-PCR, hybridoma cells (IgM, κ) suspended in diethyl pyrocarbonate treated PBS were first counted using a haemocytometer and used in the range of 1 to 100 cells. The expressed $V_κ$ and $V_H$ gene was amplified using $V_κ$ and $V_H$ pooled primers respectively, in conjunction with corresponding constant region primers, as described above. In addition, a second set of RT-PCRs were set up where the amplification cycles were increased from 25 to 50 for the first and second round PCR. The amplified product was analyzed on a 0.9% agarose gel.

Pooled 3' RT primer mix: SEQ ID NOs. 38-42 and SEQ ID NO; 96.

Pooled 5' external $V_H$ primer mix consisted of primers SEQ ID NO. 1, SEQ ID NO. 2, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO: 31 and SEQ ID NO. 33.

Pooled 5' external $V_κ$ primer mix consisted of primers SEQ ID NO. 55, SEQ ID NO. 58, SEQ ID NO. 60, SEQ ID NO. 62, SEQ ID NO. 64, SEQ ID NO. 66, SEQ ID NO. 68, SEQ ID NO. 70, SEQ ID NO. 72, SEQ ID NO. 74, SEQ ID NO. 76, SEQ ID NO. 78, SEQ ID NO. 80, SEQ ID NO. 82, SEQ ID NO. 84, SEQ ID NO. 86, SEQ ID NO. 88, SEQ ID NO. 90 and SEQ ID NO. 92.

Pooled 5' internal $V_H$ primer mix consisted of primers SEQ ID NO. 3, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32 and SEQ ID NO. 34.

Pooled 5' internal $V_κ$ primer mix consisted of primers SEQ ID NO. 56, SEQ ID NO. 57, SEQ ID NO. 59, SEQ ID NO. 61, SEQ ID NO. 63, SEQ ID NO. 65, SEQ ID NO. 67, SEQ ID NO. 69, SEQ ID NO. 71, SEQ ID NO. 73, SEQ ID NO. 75, SEQ ID NO. 77, SEQ ID NO. 79, SEQ ID NO. 81, SEQ ID NO. 83, SEQ ID NO. 85, SEQ ID NO. 87, SEQ ID NO. 89, SEQ ID NO. 91 and SEQ ID NO. 93.

Pooled 3'$C_H$ external primer mix comprised of SEQ ID NO. 43, SEQ ID NO. 45, SEQ ID NO. 46, SEQ ID NO. 49, SEQ ID NO. 51 and SEQ ID NO. 53.

The 3'$C_κ$ external primer mix was SEQ ID NO. 97.
Pooled 3'$C_H$ internal primer mix comprised of SEQ ID NO. 44, SEQ ID NO. 47, SEQ ID NO. 48, SEQ ID NO. 50, SEQ ID NO. 52, and SEQ ID NO. 54.

The 3'$C_κ$ internal primer was SEQ ID NO. 98.

Example 6

Sequencing and Sequence Analysis of the (RT)-PCR Amplified Rearranged/Expressed $V_H$ and $V_L$ Genes RT-PCR amplified $V_H$ and $V_L$ genes expressed in the hybridomas were column- or gel-purified (Qiagen, Germany) and sequenced using the appropriate $C_H$, $C_κ$ or $C_λ$ internal antisense primer (FIG. 1 and Tables 1-3). The nucleotide sequence was analyzed with MacVector software. The family to which the expressed $V_H$ and $V_L$ genes belong was assigned using IMGT and IgBLAST databases. Once the V gene family was identified, we used the corresponding 5' internal primer to sequence the second strand of the amplified product. In some experiments the (RT-) PCR product was cloned and recombinants from the resultant genomic/cDNA library were sequenced. Irrespective of whether the amplified product was sequenced directly or sequence was from a recombinant clone, the nucleotide sequence analysis was restricted to the sequence internal to the 5' and 3' internal primer. This was done to prevent mutations introduced by the primer during (RT-) PCR from affecting the sequence analysis.

Example 7

RT-PCR Amplification of H and L Chain Transcripts from Splenocytes Using Pooled Constant Region Specific Primers Total RNA was isolated from splenocytes from BALB/c mice as described above for hybridomas. The RT-PCR protocol used for hybridomas was followed for splenocytes with the following modifications. First strand cDNA was synthesized for H and L chain transcripts from splenocytes using pooled constant region specific primers. $RTC_μ$, $RTC_γ$, $RTC_α$, $RTC_κ$ and $RTC_λ$ were used at a final concentration of 0.15 μM each (Tables 1-3). Three μL of unpurified cDNA was used as template for amplifying IgM, IgG, IgA, Igκ and Igλ V gene transcripts in separate nested PCRs as described above. Independent PCRs were setup for IgG3 and the remaining IgG isotypes; IgD and IgE isotypes were not analyzed. The constant region specific primer cocktail was used in the first and second round PCR at a final concentration of 0.25 μM and each primer was present in equimolar concentration. The appropriate (external or internal) $V_H$, $V_κ$ and $V_λ$ primer pool was used for PCR amplifying the expressed IgH, Igκ and Igλ V genes, respectively. The second round PCR product was cloned in pCR2.1-TOPO (Invitrogen, USA) and transformed into TOP10 E. coli strain. The nucleotide sequence of the recombinants obtained from the resultant 6 cDNA libraries was analyzed as described above.

Pooled 5' external $V_H$ primer mix consisted of primers SEQ ID NO. 1, SEQ ID NO. 2, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31 and SEQ ID NO. 33.

Pooled 5' external $V_κ$ primer mix consisted of primers SEQ ID NO. 55, SEQ ID NO. 58, SEQ ID NO. 60, SEQ ID NO. 62, SEQ ID NO. 64, SEQ ID NO. 66, SEQ ID NO. 68, SEQ ID NO. 70, SEQ ID NO. 72, SEQ ID NO. 74, SEQ ID NO. 76, SEQ ID NO. 78, SEQ ID NO. 80, SEQ ID NO. 82, SEQ ID NO. 84, SEQ ID NO. 86, SEQ ID NO. 88, SEQ ID NO. 90 and SEQ ID NO. 92.

Pooled 5' external $V_λ$ primer mix consisted of primers SEQ ID NO. 99, SEQ ID NO. 101 and SEQ ID NO. 103.

Pooled 5' internal $V_H$ primer mix consisted of primers SEQ ID NO. 3, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32 and SEQ ID NO. 34.

Pooled 5' internal $V_κ$ primer mix consisted of primers SEQ ID NO. 56, SEQ ID NO. 57, SEQ ID NO. 59, SEQ ID NO. 61, SEQ ID NO. 63, SEQ ID NO. 65, SEQ ID NO. 67, SEQ ID NO. 69, SEQ ID NO. 71, SEQ ID NO. 73, SEQ ID NO. 75, SEQ ID NO. 77, SEQ ID NO. 79, SEQ ID NO. 81, SEQ ID NO. 83, SEQ ID NO. 85, SEQ ID NO. 87, SEQ ID NO. 89, SEQ ID NO. 91 and SEQ ID NO: 93.

Pooled 5' internal $V_\lambda$ primer mix consisted of primers SEQ ID NO. 100, SEQ ID NO. 102 and SEQ ID NO. 104.

Example 8

Identification of the Expressed $V_H$ and $V_L$ Genes from Pooled Hybridomas

Equal amounts (200 ng/hybridoma) of total RNA from 5 previously characterized IgM expressing hybridomas were mixed, and cDNA synthesized using H and L chain constant region specific antisense primers in 2 separate reverse transcription reactions. The expressed $V_H$ and $V_L$ genes in the hybridomas belonged to $V_H1, V_H2, V_H3, V_H7$ and $V_H14$, and $V_\kappa5, V_\kappa9, V_\kappa12, V_\kappa18$ and $V_\lambda2$ gene families. Separate cocktails comprising of all $V_H$ and $V_L$ (containing of both K and $\lambda$) primers and AmpliTaq DNA polymerase were used to amplify the expressed $V_H$ and $V_L$ genes from the cDNA pool. The H and L chain RT-PCR products were purified and separate libraries were constructed in TOPO-TA cloning vector. The ligated DNA was transformed in *E. Coli* strain XL1 Blue. Plasmid DNA isolated from the recombinants was digested with restriction enzyme(s) that can distinguish the $V_H$ and $V_L$ genes expressed in the 5 hybridomas. The recombinants selected after restriction profiling were confirmed by nucleotide sequencing.

Example 9

Staining, Microdissection and PCR Amplification of the Rearranged $V_H$ and $V_L$ Genes from Splenic B Cells Spleen from naive BALB/c mice were embedded in OCT, frozen over liquid nitrogen vapours, and stored at –70° C. till further use. Seven micron sections were cut using a cryostat microtome (Thermo Shandon, UK), collected on glass slides and stored at –70° C. until required. For staining, the splenic sections were washed with PBS, blocked using 2% bovine serum albumin (Vector Laboratories, USA) and incubated with rat anti-mouse B220 primary Ab (GE Biosciences, USA). The splenic sections were further incubated with horseradish peroxidase labeled goat anti-rat Ig. The B220$^+$ cells were visualized using 3,3'-diaminobenzidine (Vector Laboratories, USA) and $H_2O_2$. The sections were washed with water and dehydrated in ethanol (once in 75% ethanol for 30 s, once in 95% ethanol for 30 s and thrice in absolute ethanol for 2 min each). The splenic section was subjected to three changes of xylene. The microdissection was performed using a hydraulic micromanipulator (Narashige, Japan) assembled on an inverted microscope (Nikon, Japan). Ten to fifteen B220$^+$ cells were microdissected from the immunohistochemically stained splenic section, transferred to a 0.2 ml PCR tube containing 10 µl of 1×PCR buffer (Applied Biosystems, USA) and stored at –20° C. until required. The rearranged $V_H$ and $V_\kappa$ genes were directly PCR amplified from the microdissected B cells using pooled primer mixes comprising of primers targeting all the $V_H$ and $V_\kappa$ gene families, and the corresponding J region primer(s) as described above. The number of B cells microdissected was estimated by comparing the image of the stained section taken before and after microdissection.

Example 10

The rearranged H chain were amplified by nested PCR using splenocyte genomic DNA as template. The 50 µl first round PCR mix consisted of 1×PCR buffer 1,200 µM dNTPs, 0.25 µM external 5' (V gene) and 3' (J region) primers each, and 2.5 units of AmpliTaq DNA polymerase (Applied Biosystems, USA). Touchdown PCR was set up on a GeneAmp 2700 PCR System (Applied Biosystems, USA). The touchdown part of the PCR programme started with an initial denaturation step at 95° C. for 2 min. This was followed by denaturation at 94° C. for 1 min, annealing at 62° C. for 1 min and an extension at 72° C. for 1 min. The annealing temperature was decreased from 62° C. to 52° C. over 5 cycles at the rate of 2° C. per cycle. This was followed by 25 cycles consisting of denaturation at 94° C. for 1 min, annealing at 52° C. for 1 min and an extension at 72° C. for 1 min. A final extension step was carried out at 72° C. for 10 min. The first round primer mix comprised of SEQ ID NOs: 1, 2, 5, 7, 9, 11, 13, 15, 17, 19, 21, 23, 25, 27, 29, 31, 33 and 35. The composition of the reaction mixture and cycling parameters for the second round PCR were same as were used for the first round PCR except that 2 µl of the unpurified first round PCR product served as template for the second round PCR in place of splenocyte genomic DNA. The second round primer set comprised of SEQ ID NOs. 3, 4, 6, 8, 10, 12, 14, 16, 18, 20, 22, 24, 26, 28, 30, 32, 34, 36 and 37.

Example 10 describes the process of amplifying rearranged H chain by nested PCR using splenocyte genomic DNA as template. The same process can be repeated for amplifying the κ and λ L chains using the corresponding primers described in Table 1-3.

Example 11

The rearranged H chains were amplified by nested PCR using total or polyA$^+$ RNA as template. The 20 µl reverse transcription reaction mixture consisted of 1×PCR buffer II, 0.75 µM antisense primer, 10 mM dNTP mix, 5 mM MgCl2, 1 U of RNase inhibitor, 50 U of MuLV reverse transcriptase (Applied Biosystems, USA) and 10 µg of total RNA. The reaction was performed at 42° C. for 1 h. Reverse transcriptase was inactivated by incubating at 99° C. for 5 min. The reverse transcription reaction was done using a primer mix comprising of SEQ ID NOs. 38-42.

The 50 µl first round PCR mix consisted of 1×PCR buffer 1,200 µM dNTPs, 0.25 µM external 5' (V gene) and 3' (C region) primers each, and 2.5 units of Pfu Ultra Hotstart buffer and Pfu Ultra Hotstart DNA polymerase (Stratagene, USA) (Applied Biosystems, USA). Touchdown PCR was set up on a GeneAmp 2700 PCR System (Applied Biosystems, USA). The touchdown part of the PCR programme started with an initial denaturation step at 95° C. for 2 min. This was followed by denaturation at 94° C. for 1 min, annealing at 62° C. for 1 min and an extension at 72° C. for 1 min. The annealing temperature was decreased from 62° C. to 52° C. over 5 cycles at the rate of 2° C. per cycle. This was followed by 25 cycles consisting of denaturation at 94° C. for 1 min, annealing at 52° C. for 1 min and an extension at 72° C. for 1 min. A final extension step was carried out at 72° C. for 10 min. The first round PCR was done using a primer set consisting of SEQ ID NO: 1, 2, 5, 7, 9, 11, 13, 15, 17, 19, 21, 23, 25, 27, 29, 31, 33, 43, 45, 46, 49, 51 and 53. Five µl of unpurified cDNA was used as a template for the first round PCR. The composition of the reaction mixture and cycling parameters for the second round PCR were same as were used for the first round PCR except that 2 µl of the unpurified first round PCR product served as template for the second round PCR in place of genomic DNA. The primer set for the second round PCR comprised of SEQ ID No. 3, 4, 6, 8, 10, 12, 14, 16, 18, 20, 22, 24, 26, 28, 30, 32, 34, 44, 47, 48, 50, 52 and 54.

Example 11 describes the process of amplifying the rearranged H chain by nested PCR using total or polyA+ RNA as template. The same process can be used for amplifying the κ and λ L chains using the corresponding primers described in Table 1-3.

BIBLIOGRAPHY

Brezinschek, H. P., Brezinschek, R. I. and Lipsky, P. E. (1995) Analysis of the heavy chain repertoire of human peripheral B cells using single-cell polymerase chain reaction. J Immunol 155, 190-202.

Chardes, T., Villard, S., Ferrieres, G., Piechaczyk, M., Cerutti, M., Devauchelle, G. and Pau, B. (1999) Efficient amplification and direct sequencing of mouse variable regions from any immunoglobulin gene family. FEBS Lett 452, 386-94.

Chiang, Y. L., Sheng-Dong, R., Brow, M. A. and Larrick, J. W. (1989) Direct cDNA cloning of the rearranged immunoglobulin variable region. Biotechniques 7, 360-6.

Coloma, M. J., Larrick, J. W., Ayala, M. and Gavilondo-Cowley, J. V. (1991) Primer design for the cloning of immunoglobulin heavy-chain leader-variable regions from mouse hybridoma cells using the PCR. Biotechniques 11, 152-4, 156. Dattamajumdar, A. K., Jacobson, D. P., Hood, L. E. and Osman, G. E. (1996) Rapid cloning of any rearranged mouse immunoglobulin variable genes. Immunogenetics 43, 141-51.

Dohmen, S. E., Mulder, A., Verhagen, O. J., Eijsink, C., Franke-van Dijk, M. E. and van der Schoot, C. E. (2005) Production of recombinant Ig molecules from antigen-selected single B cells and restricted usage of Ig-gene segments by anti-D antibodies. J Immunol Methods 298, 9-20.

Essono, S., Frobert, Y., Grassi, J., Creminon, C. and Boquet, D. (2003) A general method allowing the design of oligonucleotide primers to amplify the variable regions from immunoglobulin cDNA. J Immunol Methods 279, 251-66.

Framer, N. L., Dorner, T. and Lipsky, P. E. (1999) Molecular mechanisms and selection influence the generation of the human V lambda J lambda repertoire. J Immunol 162, 2137-45.

Foster, S. J., Brezinschek, H. P., Brezinschek, R. I. and Lipsky, P. E. (1997) Molecular mechanisms and selective influences that shape the kappa gene repertoire of IgM+ B cells. J Clin Invest 99, 1614-27.

Guo, L., Zhang, X., Zheng, B. and Han, S. (2008) IgM-mediated signaling is required for the development of a normal B cell memory response. Mol Immunol 45, 1071-7.

Jacob, J., Kassir, R. and Kelsoe, G. (1991a) In situ studies of the primary immune response to (4-hydroxy-3-nitrophenyl)acetyl. I. The architecture and dynamics of responding cell populations. J Exp Med 173, 1165-75.

Jacob, J., Kelsoe, G., Rajewsky, K. and Weiss, U. (1991b) Intraclonal generation of antibody mutants in germinal centres. Nature 354, 389-92.

Jones, S. T. and Bendig, M. M. (1991) Rapid PCR-cloning of full-length mouse immunoglobulin variable regions. Biotechnology (N Y) 9, 88-9.

Kettleborough, C. A., Saldanha, J., Ansell, K. H. and Bendig, M. M. (1993) Optimization of primers for cloning libraries of mouse immunoglobulin genes using the polymerase chain reaction. Eur J Immunol 23, 206-11.

Kim, H. J. and Berek, C. (2007) Single cell analysis of synovial tissue B-cells. Methods Mol Med 136, 25-37.

Krebber, A., Bornhauser, S., Burmester, J., Honegger, A., Willuda, J., Bosshard, H. R. and Pluckthun, A. (1997) Reliable cloning of functional antibody variable domains from hybridomas and spleen cell repertoires employing a reengineered phage display system. J Immunol Methods 201, 35-55.

Lan, F., Umeda, M. and Inoue, K. (1996) Extended fitness of variable region primers by a novel PCR protocol. J Immunol Methods 195, 27-32.

Larrick, J. W., Coloma, M. J., del Valle, J., Fernandez, M. E., Fry, K. E. and Gavilondo-Cowley, J. V. (1990) Immunoglobulin V regions of a bactericidal anti-*Neisseria meningitidis* outer membrane protein monoclonal antibody. Scand J Immunol 32, 121-8.

LeBoeuf, R. D., Galin, F. S., Hollinger, S. K., Peiper, S. C. and Blalock, J. E. (1989) Cloning and sequencing of immunoglobulin variable-region genes using degenerate oligodeoxyribonucleotides and polymerase chain reaction. Gene 82, 371-7.

Nicholls, P. J., Johnson, V. G., Blanford, M. D. and Andrew, S. M. (1993) An improved method for generating single-chain antibodies from hybridomas. J Immunol Methods 165, 81-91.

Orlandi, R., Gussow, D. H., Jones, P. T. and Winter, G. (1989) Cloning immunoglobulin variable domains for expression by the polymerase chain reaction. Proc Natl Acad Sci USA 86, 3833-7.

Owens, R. J. and Young, R. J. (1994) The genetic engineering of monoclonal antibodies. J Immunol Methods 168, 149-65.

Ruberti, F., Cattaneo, A. and Bradbury, A. (1994) The use of the RACE method to clone hybridoma cDNA when V region primers fail. J Immunol Methods 173, 33-9.

Sehgal, D., Schiaffella, E., Anderson, A. O. and Mage, R. G. (1998) Analyses of single B cells by polymerase chain reaction reveal rearranged $V_H$ with germline sequences in spleens of immunized adult rabbits: implications for B cell repertoire maintenance and renewal. J Immunol 161, 5347-56.

Seijen, A. M., Seijen, H. G. and Bos, N. A. (2001) Systematic design of mouse Vh gene family-specific oligonucleotides. J Immunol Methods 254, 161-8.

Tiller, T., Meffre, E., Yurasov, S., Tsuiji, M., Nussenzweig, M. C. and Wardemann, H. (2007) Efficient generation of monoclonal antibodies from single human B cells by single cell RT-PCR and expression vector cloning. J Immunol Methods.

Wang, Y., Chen, W., Li, X. and Cheng, B. (2006) Degenerated primer design to amplify the heavy chain variable region from immunoglobulin cDNA. BMC Bioinformatics 7 Suppl 4, S9.

Wang, Z., Raifui, M., Howard, M., Smith, L., Hansen, D., Goldsby, R. and Ratner, D. (2000) Universal PCR amplification of mouse immunoglobulin gene variable regions: the design of degenerate primers and an assessment of the effect of DNA polymerase 3' to 5' exonuclease activity. J Immunol Methods 233, 167-77.

Wang, X. and Stollar, B. D. (2000) Human immunoglobulin variable region gene analysis by single cell RT-PCR. J Immunol Methods 244, 217-225.

Zhou, H., Fisher, R. J. and Papas, T. S. (1994) Optimization of primer sequences for mouse scFv repertoire display library construction. Nucleic Acids Res 22, 888-9.

TABLE 1

Oligonucleotide primers for PCR amplification of rearranged $V_H$ genes from genomic DNA and total RNA

| Family or gene[a] | Total no. of genes (%)[b] | External primers[c] | Fold Deg[d] | Mismatches[e] 0 | 1 | 2 | 3 | 4 | Internal primers | Fold Deg | Mismatches 0 | 1 | 2 | 3 | 4 |
|---|---|---|---|---|---|---|---|---|---|---|---|---|---|---|---|
| $V_H1$[f] | 193 (55) | agRtYcagctgcaRcagtct aggtccaactgcagcagcc | 8 1 | 103 | 42 | 10 | 6 | 3 | gaRgatRtcctgYaaggcttc aRgBtgtcctgcaagRcttc | 8 12 | 126 | 37 | 18 | 2 | 1 |
| $V_H2$[g] | 14 (4) | tctgcctggtgacWttccca | 2 | 7 | | 1 | 1 | | tgcagctgaagSagtcagga | 2 | 9 | 1 | | | |
| $V_H3$ | 9 (2.6) | gtgcagcttcaggagtcag | 1 | 6 | 2 | | | 1 | aaccttctcagWcactgtcc | 2 | | 4 | 5 | | |
| $V_H4$ | 3 (0.9) | gaggtgaagcttctcgagtc | 1 | 2 | 1 | | | | ggaggtggcctggtgcag | 1 | 3 | | | | |
| $V_H5$[h] | 52 (14.8) | gaagtgaagctggtggagtc | 1 | 5 | 9 | 20 | 5 | | agcctggagggtccctgaa | 1 | 2 | 34 | 6 | 1 | 4 |
| $V_H6$[i] | 6 (1.7) | atgKacttgggactgaRctgt | 4 | 2 | 3 | | | | gaggagtctggaggaggctt | 1 | 3 | 2 | 1 | | |
| $V_H7$ | 7 (2) | cagtgtgaggtgaagctggt | 1 | 5 | 2 | | | | tctggaggaggcttggtaca | 1 | 6 | 1 | | | |
| $V_H8$[j] | 22 (6.3) | ccaggttactctgaaagagtc | 1 | 11 | 2 | 3 | 3 | | ctgggatattgcagccctcc | 1 | 4 | 8 | 6 | 1 | |
| $V_H9$[k] | 21 (6) | tgtggaccttgctattcctga | 1 | 13 | 4 | | 1 | | acagatccagttggtgcagt | 1 | 15 | 6 | | | |
| $V_H10$[l] | 8 (2.3) | tgttggggctgaagtgggttt | 1 | 5 | 2 | | | | aggtgtgcattgtgaggtgc | 1 | 7 | 1 | | | |
| $V_H11$ | 3 (0.9) | atggagtgggaactgagctta | 1 | 3 | | | | | gaagtgcagctgttggagac | 1 | 3 | | | | |
| $V_H12$ | 2 (0.6) | agcttcaggagtcaggacc | 1 | 2 | | | | | cctggtgaaaccctcacag | 1 | 2 | | | | |
| $V_H13$ | 2 (0.6) | caggtgcagcttgtagagac | 1 | 2 | | | | | aggcttggtgaggcctgga | 1 | 2 | | | | |
| $V_H14$[m] | 5 (1.4) | atgcagctgggtcatcttctt | 1 | 2 | 1 | 1 | | | gaggttcagctgcagcagt | 1 | 5 | | | | |
| $V_H15$ | 2 (0.6) | gactggatttggatcacKctc | 2 | 1 | 1 | | | | caatcccaggttcacctacaa | 1 | 2 | | | | |
| $V_H16$ | 1 (0.3) | tggagtttggacttagttggg | 1 | 1 | | | | | gtgaggtgcagctggtgga | 1 | 1 | | | | |
| $J_H$ | 4 | ctYacctgaggagacDgtga | 6 | 2 | 1 | 1 | | | gtggtccctgcgcccag ggtBccttggcccagta | 1 3 | 2 | 2 | | | |
| RTCμ | 1 | gatgacttcagtgttgt | 1 | 1 | | | | | | | | | | | |
| RTCγ | 5 | cagggatccaKagttc | 1 | 4 | 1 | | | | | | | | | | |
| RTCα | 1 | caggtcacattcatcg | 1 | 1 | | | | | | | | | | | |
| RTCε | 1 | cacagtgctcatgttca | 1 | 1 | | | | | | | | | | | |
| RTCδ[n] | 1 | agtggctgacttccaa | 1 | 1 | | | | | | | | | | | |
| Cμ | 1 | catggccaccagattcttatc | 1 | 1 | | | | | agacatttgggaaggactgac | 1 | 1 | | | | |
| Cγ | 5 | agggaaataRcccttgaccag agggaagtagcctttgacaag | 1 1 | 4 | 1 | | | | ggccagtggatagacHgatg cagggaccaagggatagaca | 3 1 | 5 | | | | | |
| Cα | 1 | gaatcaggcagccgattatcac | 1 | 1 | | | | | tgggagtgtcagtgggtaga | 1 | 1 | | | | |

TABLE 1-continued

Oligonucleotide primers for PCR amplification of rearranged $V_H$ genes from genomic DNA and total RNA

| Family or gene[a] | Total no. of genes (%)[b] | External primers[c] | Fold Deg[d] | Mismatches[e] 0 | 1 | 2 | 3 | 4 | Internal primers | Fold Deg | Mismatches 0 | 1 | 2 | 3 | 4 |
|---|---|---|---|---|---|---|---|---|---|---|---|---|---|---|---|
| Cε | 1 | tcatggaagcagtgcctttac | 1 | 1 | | | | | tagagctgagggttcctgata | 1 | 1 | | | | |
| Cδ[n] | 1 | tctgagaggaggaacatgtc | 1 | 1 | | | | | tcacctgcaagacagatagtg | 1 | 1 | | | | |

[a]The 16 pseudogenes that are grouped as 'unclassified' in the mouse germline $V_H$ IgBLAST database were very diverse in sequence and were not analyzed for designing primers.
[b]The number of germline sequences present in the family analyzed. The proportion of genes contributed by a given family to the total number of genes present in our $V_H$ database is given in parenthesis.
[c]All oligonucleotide primers are listed in 5' to 3' direction. The degenerate bases are shown in upper case. IUPAC code for mix bases: M, a/c; R, a/g; W, a/t; Y, c/t; S, c/g; K, g/t; H, a/c/t; V, a/c/g; D, a/g/t; B, c/g/t; N, a/c/g/t.
[d]Fold degeneracy.
[e]Number of sequences with the indicated number of mismatches vis-à-vis the primer sequence.
[f]Eight sequences (AF455996, AF455989, AF455290, AF458189, AF459867, AF455983, AF303885 and AY672647) were incomplete and were excluded from the analysis. In addition, 21 sequences (not listed here) were not considered for designing the external primer, as they were incomplete at the 5' end. The pseudogene J558.57pg.152 was not considered for designing the internal primer, as it was too divergent.
[g]Four pseudogenes (Q52.12pg.39, Q52.6pg.17, Q52.4pg.12 and Q52.1pg.2) either lacked the leader sequence or were too divergent in sequence and were not considered for designing the primers. The database entry U53526 (a functional gene) was not complete at the 5' end and was not considered while designing the external primer.
[h]Five pseudogenes (7183.3pg.5, 7183.5pg.7, 7183.11pg.19, 7183.17pg.31 and 7183.21pg.38) were too divergent in sequence and were not considered for designing the primers. The sequences of eight functional genes (M18314, AF120462, AF290963, AF428078, U04228, U04230, U04231 and X67409) were incomplete at the 5' end and could not be included while designing the external primer.
[i]GenBank entry X03398 lacked the leader sequence and was not considered for designing the external primer.
[j]Three pseudogenes 3609.2pg.138, 3609.10pg.167 and 3609N.1pg.68 were too divergent in sequence and were excluded from the analysis.
[k]The sequences of three functional genes (L14364, L14367 and L14368) were incomplete at the 5' end and could not be included while designing the external primer.
[l]Pseudogene VH10.2pg.89 was not included in designing the external primer, as the sequence was incomplete at the 5' end.
[m]X55934 was not included for designing the external primer, as sequence was incomplete at the 5' end.
[n]Under special experimental settings (Guo et al., 2008) one may be interested in analyzing the IgD repertoire.

TABLE 2

Oligonucleotide primers for PCR amplification of rearranged $V_κ$ genes from genomic DNA and total RNA

| Family or gene | Total no. of genes (%) | External primers | Fold Deg | Mismatches 0 | 1 | 2 | 3 | 4 | Internal primers | Fold Deg | Mismatches 0 | 1 | 2 | 3 | 4 |
|---|---|---|---|---|---|---|---|---|---|---|---|---|---|---|---|
| $V_κ1$[a] | 13 (7.9) | tgatgacccaRactccact | 2 | 8 | 1 | 2 | | | cctgtcagtcttggagatca<br>tttgtcggttaccattggacaa | 1<br>1 | 7 | 1 | 2 | 1 | |
| $V_κ2$[b] | 11 (6.7) | gcttgtgctctggatccc | 1 | 3 | 3 | | 1 | | SRgatattgtgatgacgcagg | 4 | 3 | 1 | 1 | 2 | |
| $V_κ3$ | 12 (7.3) | ctgctgctctgggttcc | 1 | 10 | 1 | | 1 | | attgtgctgacccaatctcc | 1 | 8 | 1 | 1 | 2 | |
| $V_κ4$[c] | 33 (20.1) | cagcttcctgctaatcagtg | 1 | 20 | 8 | 1 | | 1 | aWtgtKctcacccagtctcc | 4 | 23 | 6 | | | 1 |
| $V_κ5$ | 6 (3.7) | ctcagatccttggacttHtg | 3 | | 5 | 1 | | | gtctccagccaccctgtc | 1 | 5 | 1 | | | |
| $V_κ6$ | 12 (7.3) | tggagtcacagacYcagg | 2 | 1 | 6 | 4 | 1 | | tgatgacccagtctcMcaaat | 2 | 4 | 6 | 2 | | |
| $V_κ7$ | 1 (0.6) | tggagtttcagacccagg | 1 | 1 | | | | | gcctgtgcagacattgtgat | 1 | 1 | | | | |
| $V_κ8$ | 13 (7.9) | ctgctMtgggtatctggt | 2 | 7 | 6 | | | | cctgtggggacattgtgatg | 1 | 7 | 1 | 4 | 1 | |
| $V_κ9$ | 6 (3.7) | cWtcttgttgctctggtttc | 2 | 3 | 3 | | | | acatccRgatgacYcagtct | 4 | 4 | 2 | | | |
| $V_κ10$ | 3 (1.8) | gatgtcctctgctcagttc | 1 | 3 | | | | | ccagatgtgatatccagatg | 1 | 2 | 1 | | | |

TABLE 2-continued

Oligonucleotide primers for PCR amplification of
rearranged $V_\kappa$ genes from genomic DNA and total RNA

| Family or gene | Total no. of genes (%) | External primers | Fold Deg | Mismatches 0 | 1 | 2 | 3 | 4 | Internal primers | Fold Deg | Mismatches 0 | 1 | 2 | 3 | 4 |
|---|---|---|---|---|---|---|---|---|---|---|---|---|---|---|---|
| $V_\kappa 11$ | 4 (2.4) | cctgctgagttccttggg | 1 | 1 | | 1 | 2 | | gccagatgtgatgtYcaaatg | 2 | 1 | 3 | | | |
| $V_\kappa 12^d$ | 13 (7.9) | ctgctgctgtggcttaca | 1 | 8 | 1 | 1 | 1 | | atccagatgactcagtctcc | 1 | 7 | 3 | 3 | | |
| $V_\kappa 13^e$ | 18 | ccttctcaacttctgctct | 1 | 2 | | 1 | | 4 | cctgatatgtgacatccRVat | 6 | 4 | 2 | 1 | | |
| $V_\kappa 14^f$ | 8 (4.9) | agggcccYtgctcagttt | 2 | 1 | 3 | 1 | | | Magatgacccagtctccatc | 2 | 2 | 1 | 2 | | |
| $V_\kappa 15^g$ | 5 (3.1) | atgagggtccttgctgag | 1 | 1 | | | 1 | | tgagatgtgacatccagatga | 1 | 2 | | | | |
| $V_\kappa 16$ | 1 (0.6) | gaggttccaggttcaggt | 1 | 1 | | | | | ccagtgtgatgtccagataac | 1 | 1 | | | | |
| $V_\kappa 17$ | 3 (1.8) | ccatgaccatgYtctcact | 2 | 2 | 1 | | | | acaactgtgacccagtctcc | 1 | 2 | 1 | | | |
| $V_\kappa 18$ | 1 (0.6) | atggaaactccagcttcattt | 1 | 1 | | | | | acacaggctccagcttctct | 1 | 1 | | | | |
| $V_\kappa 19$ | 1 (0.6) | atgagaccgtctattcagtt | 1 | 1 | | | | | gtgctcagtgtgacatccag | 1 | 1 | | | | |
| $J_\kappa$ | 5 | tStacttacgtttBatttcca | 6 | 2 | 1 | 1 | 1 | | tttBatttccagcttggtScc | 6 | 2 | | 3 | | |
| $RTC_\kappa$ | 1 | tcaagaagcacacgac | 1 | 1 | | | | | | | | | | | |
| $C_\kappa$ | 1 | gcacctccagatgttaactg | 1 | 1 | | | | | gatggtgggaagatggatac | 1 | 1 | | | | |

Also refer to the Table 1 footnotes.
[a] Two pseudogenes (AJ231202 and AJ231204) were not included in the analysis as the sequences were too divergent.
[b] Four pseudogenes (AJ132682, AJ231261, AJ231265 and AJ231266) were not included in the analysis as the sequences were too divergent.
[c] Two pseudogenes (AJ231220, AJ231230) and a functional gene (AJ231226) were not included in the analysis as the sequences were too divergent.
[d] J00546 could not be included in designing the external primer as the GenBank entry does not cover the leader sequence. The database entry AJ235950 could not be included in designing the external primer as the sequence was too divergent.
[e] Eleven pseudogenes (AJ132671-76, AJ132678-81 and AJ231272) were not included in the analysis as the sequences were too divergent.
[f] Three pseudogenes (AJ231237, AJ231246 and AJ231249) were not included in the analysis as the sequences were too divergent.
[g] Three pseudogenes (AJ231251, AJ231268 and AJ231270) were not included in the analysis as the sequences were too divergent.

TABLE 3

Oligonucleotide primers for PCR amplification of
rearranged $V_\lambda$ genes from genomic DNA and total RNA

| Family or Gene | Total no. of genes (%) | External primers | Fold Deg | Mismatches 0 | 1 | Internal primers | Fold Deg | Mismatches 0 | 2 |
|---|---|---|---|---|---|---|---|---|---|
| $V_\lambda 1/2$ | 2 (66.7) | gcctggaYttcacttatactc | 2 | 2 | | tcccaggctgttgtgactc | 1 | 2 | |
| $V_\lambda 3$ | 1 (33.3) | tggcctggactcctctctt | 1 | 1 | | caacttgtgctcactcagtc | 1 | 1 | |
| $V_\lambda 4/5/6/$ | 5 | actcagccaagctctgtg | 1 | 5 | | ctctaggaagcacagtcaaac | 1 | 5 | |
| $J_\lambda^b$ | 5 | gYcactYacctaggacag<br>aaactacttacctaggacag | 4<br>1 | 3 | 1 | taggacagtcagtttggttcc<br>aggacagtgaccttggttcc | 1<br>1 | 3 | 1 |
| $RTC_\lambda$ | 4 | acaccagtgtggcYtt | 2 | 3 | 1 | | | | |

TABLE 3-continued

Oligonucleotide primers for PCR amplification of rearranged $V_\lambda$ genes from genomic DNA and total RNA

| Family or Gene | Total no. of genes (%) | External primers | Fold Deg | Mismatches 0 | Mismatches 1 | Internal primers | Fold Deg | Mismatches 0 | Mismatches 2 |
|---|---|---|---|---|---|---|---|---|---|
| $C_\lambda$ | 4 | agctcctcagRggaaggtg | 2 | 3 | 1 | gaaacacggtgagWgtggg | 2 | 3 | 1 |
|  |  |  |  |  |  | gaaacagggtgactgatgg | 1 |  |  |

[a] This set of genes are absent in C57BL/6, BALB/c and other common laboratory mice (IMGT; http://imgt.cines.fr). We did not detect any PCR product with CBA/J splenocyte genomic DNA.;
[b] The pseudogene $J_\lambda 3P$ was not included in the analysis.

TABLE 4

Sequence analysis of rearranged V genes recovered from $V_H$, $V_\kappa$ and $V_\lambda$ gene family-specific libraries

| Gene family | Recombinants analyzed | V | D | J |
|---|---|---|---|---|
| *Heavy chain* | | | | |
| $V_H 1$ | 6 | J558.47.137 | DSP2.x | $J_H 4$ |
|  |  | J558.11 | DFL16.1, DFL16.2[a] | $J_H 4$ |
|  |  | V6 | DSP2.9 | $J_H 3$ |
|  |  | V6 | DST4.3, DST4.2, DST4-BALB/c[a] | $J_H 4$ |
|  |  | V6 | DSP2.12 | $J_H 4$ |
|  |  | V23 | DQ52-C57BL/6, DQ52-BALB/c[a] | $J_H 2$ |
| $V_H 4$ | 4 | X24.2.50 | DSP2.x | $J_H 1$ |
|  |  | X24.2.50 | DSP2.x | $J_H 2$ |
|  |  | X24.2.50 | DQ52-C57BL/6 | $J_H 1$ |
|  |  | X24.2.50 | DSP2.9 | $J_H 2$ |
| $V_H 5$ | 4 | VH7183.a24.40 | DSP2.x | $J_H 3$ |
|  |  | VH7183.a28.48 | DFL16.1j | $J_H 1$ |
|  |  | VH7183.1j | DSP2.2 | $J_H 4$ |
| $V_H 8$ | 4 | 3609.7.153 | DSP2.x | $J_H 4$ |
|  |  | 3609.4.142 | DQ52-BALB/c | $J_H 1$ |
|  |  | 3609.12.174 | DSP2.x | $J_H 2$ |
|  |  | 3609.12.174 | DSP2.x | $J_H 3$ |
| $V_H 11$ | 5 | VH11.1.48 | DSP2.12 | $J_H 4$ |
|  |  | VH11.1.48 | DSP2.13 | $J_H 1$ |
|  |  | VH11.1.48 | DSP2.5, DSP2.7, DSP2.8[a] | $J_H 1$ |
|  |  | VH11.1.48 | DSP2.x, DSP2.8[a] | $J_H 4$ |
| $V_H 15$ | 5 | VH15B | DQ52-C57BL/6 | $J_H 2$ |
|  |  | VH15B | DSP2.9 | $J_H 4$ |
|  |  | VH15B | DSP2.x | $J_H 2$ |
|  |  | VH15B | DSP2.13 | $J_H 2$ |
| *κ light chain* | | | | |
| $V_\kappa 3$ | 4 | 21-4 |  | $J_\kappa 1$ |
|  |  | 21-10 |  | $J_\kappa 2$ |
|  |  | 21-5 |  | $J_\kappa 1$ |
| $V_\kappa 4$ | 5 | ko4 |  | $J_\kappa 1$ |
|  |  | ko4 |  | $J_\kappa 2$ |
|  |  | kk4 |  | $J_\kappa 2$ |
|  |  | kn4 |  | $J_\kappa 1$ |
|  |  | ah4 |  | $J_\kappa 1$ |
| $V_\kappa 11$ | 6 | if11 |  | $J_\kappa 1, J_\kappa 5$[a] |
|  |  | if11 |  | $J_\kappa 1$ |
|  |  | if11 |  | $J_\kappa 1$ |
|  |  | if11 |  | $J_\kappa 1$ |
|  |  | if11 |  | $J_\kappa 1$ |
|  |  | if11 |  | $J_\kappa 2$ |
| $V_\kappa 13$ | 4 | gm33 |  | $J_\kappa 1$ |
|  |  | gm33 |  | $J_\kappa 1$ |
|  |  | gm33 |  | $J_\kappa 1$ |
|  |  | gm33 |  | $J_\kappa 2$ |
| $V_\kappa 14$ | 2 | ba9 |  | $J_\kappa 2$ |
|  |  | cb9 |  | $J_\kappa 1$ |
| $V_\kappa 17$ | 4 | bw20 |  | $J_\kappa 2$ |
|  |  | bt20 |  | $J_\kappa 2$ |
|  |  | bt20 |  | $J_\kappa 2$ |
|  |  | bt20 |  | $J_\kappa 4$ |
| *λ light chain* | | | | |
| $V_\lambda 1/2$ | 4 | VL1 |  | $J_\lambda 2$ |
|  |  | VL2 |  | $J_\lambda 1$ |
|  |  | VL2 |  | $J_\lambda 2$ |
| $V_\lambda 3$ | 4 | VLx |  | $J_\lambda 2$ |

[a] Any one of the 2 or 3 gene fragments listed may have been used in the Ig rearrangement.

TABLE 5

Comparative analysis of degree of degeneracy in V gene primer sets designed

| Reference | V genes covered | No. of primers | Degeneracy range | Average degeneracy |
|---|---|---|---|---|
| LeBoeuf et al., 1989 | $V_H$, $V_\kappa$ | 2 | 432-576 | 504 |
| Larrick et al., 1990 | $V_H$, $V_\kappa$ | 2 | 32-128 | 80 |
| Coloma et al., 1991 | $V_H$ | 4 | 32-512 | 280 |
| Lan et al., 1996 | $V_H$, $V_\kappa$ | 4 | 1-512 | 152.3 |
| Wang et al., 2000 | $V_H$, $V_\kappa$ | 8 | 1-256 | 66.4 |
| Kettleborough et al., 1993 | $V_H$, $V_\kappa$ | 17 | 4-128 | 43 |
| Jones and Bendig, 1991 | $V_H$, $V_\kappa$ | 23 | 1-128 | 14.7 |
| Essono et al., 2003 | $V_H$, $V_\kappa$ | 31 | 1-147456 | 6090.1 |
| Chardes et al., 1999 | $V_H$, $V_\kappa$ | 63 | 1-12 | 2.5 |
| Seijen et al., 2001 | $V_H$ | 16 | 1-3 | 1.6 |
| The present invention | $V_H$, $V_\kappa$, $V_\lambda$ | 77[a] | 1-12 | 1.8 |

[a] An analysis of all our V gene primers (38 external and 39 internal) is presented here for comparison purposes.

TABLE 6

Summary

| PCR template | Gene family | Primer SEQ ID Number | Primer Set No. |
|---|---|---|---|
| Genomic DNA | All rearranged $V_H$, $V_\kappa$ and $V_\lambda$ | 1-37 + 55-95 + 99-108 | Set 1 |
| | All rearranged $V_H$ | 1-37 | Set 2 |
| | $V_H$1 family | 1-4 + 35-37 | Set 3 |
| | $V_H$2 family | 5-6 + 35-37 | Set 4 |
| | $V_H$3 family | 7-8 + 35-37 | Set 5 |
| | $V_H$4 family | 9-10 + 35-37 | Set 6 |
| | $V_H$5 family | 11-12 + 35-37 | Set 7 |
| | $V_H$6 family | 13-14 + 35-37 | Set 8 |
| | $V_H$7 family | 15-16 + 35-37 | Set 9 |
| | $V_H$8 family | 17-18 + 35-37 | Set 10 |
| | $V_H$9 family | 19-20 + 35-37 | Set 11 |
| | $V_H$10 family | 21-22 + 35-37 | Set 12 |
| | $V_H$11 family | 23-24 + 35-37 | Set 13 |
| | $V_H$12 family | 25-26 + 35-37 | Set 14 |
| | $V_H$13 family | 27-28 + 35-37 | Set 15 |
| | $V_H$14 family | 29-30 + 35-37 | Set 16 |
| | $V_H$15 family | 31-32 + 35-37 | Set 17 |
| | $V_H$16 family | 33-37 | Set 18 |
| | All rearranged $V_L$ | 55-95 + 99-108 | Set 19 |
| | All rearranged $V_\kappa$ | 55-95 | Set 20 |
| | $V_\kappa$1 family | 55-57 + 94-95 | Set 21 |
| | $V_\kappa$2 family | 58-59 + 94-95 | Set 22 |
| | $V_\kappa$3 family | 60-61 + 94-95 | Set 23 |
| | $V_\kappa$4 family | 62-63 + 94-95 | Set 24 |
| | $V_\kappa$5 family | 64-65 + 94-95 | Set 25 |
| | $V_\kappa$6 family | 66-67 + 94-95 | Set 26 |
| | $V_\kappa$7 family | 68-69 + 94-95 | Set 27 |
| | $V_\kappa$8 family | 70-71 + 94-95 | Set 28 |
| | $V_\kappa$9 family | 72-73 + 94-95 | Set 29 |
| | $V_\kappa$10 family | 74-75 + 94-95 | Set 30 |
| | $V_\kappa$11 family | 76-77 + 94-95 | Set 31 |
| | $V_\kappa$12 family | 78-79 + 94-95 | Set 32 |
| | $V_\kappa$13 family | 80-81 + 94-95 | Set 33 |
| | $V_\kappa$14 family | 82-83 + 94-95 | Set 34 |
| | $V_\kappa$15 family | 84-85 + 94-95 | Set 35 |
| | $V_\kappa$16 family | 86-87 + 94-95 | Set 36 |
| | $V_\kappa$17 family | 88-89 + 94-95 | Set 37 |
| | $V_\kappa$18 family | 90-91 + 94-95 | Set 38 |
| | $V_\kappa$19 family | 92-95 | Set 39 |
| | All rearranged $V_\lambda$ | 99-108 | Set 40 |
| | $V_\lambda$1 and $V_\lambda$2 genes | 99-100 + 105-108 | Set 41 |
| | $V_\lambda$3 gene | 101-102 + 105-108 | Set 42 |
| | $V_\lambda$4, $V_\lambda$5, $V_\lambda$6, $V_\lambda$7 and $V_\lambda$8 genes | 103-108 | Set 43 |
| Total or poly A$^+$ RNA | Total expressed $V_H$, $V_\kappa$ and $V_\lambda$ | 1-34 + 38-93 + 96-104 + 109-112 | Set 44 |
| | All expressed H chains | 1-34 + 38-54 | Set 45 |
| | IgM isotype | 1-34 + 38 + 43-44 | Set 46 |
| | IgG isotype | 1-34 + 39 + 45-48 | Set 47 |
| | IgA isotype | 1-34 + 40 + 49-50 | Set 48 |
| | IgE isotype | 1-34 + 41 + 51-52 | Set 49 |
| | IgD isotype | 1-34 + 42 + 53-54 | Set 50 |
| | $V_H$1 family (all $V_H$ isotypes) | 1-4 + 38-54 | Set 51 |
| | $V_H$2 family (all $V_H$ isotypes) | 5-6 + 38-54 | Set 52 |
| | $V_H$3 family (all $V_H$ isotypes) | 7-8 + 38-54 | Set 53 |
| | $V_H$4 family (all $V_H$ isotypes) | 9-10 + 38-54 | Set 54 |
| | $V_H$5 family (all $V_H$ isotypes) | 11-12 + 38-54 | Set 55 |
| | $V_H$6 family (all $V_H$ isotypes) | 13-14 + 38-54 | Set 56 |
| | $V_H$7 family (all $V_H$ isotypes) | 15-16 + 38-54 | Set 57 |
| | $V_H$8 family (all $V_H$ isotypes) | 17-18 + 38-54 | Set 58 |
| | $V_H$9 family (all $V_H$ isotypes) | 19-20 + 38-54 | Set 59 |
| | $V_H$10 family (all $V_H$ isotypes) | 21-22 + 38-54 | Set 60 |
| | $V_H$11 family (all $V_H$ isotypes) | 23-24 + 38-54 | Set 61 |
| | $V_H$12 family (all $V_H$ isotypes) | 25-26 + 38-54 | Set 62 |
| | $V_H$13 family (all $V_H$ isotypes) | 27-28 + 38-54 | Set 63 |
| | $V_H$14 family (all $V_H$ isotypes) | 29-30 + 38-54 | Set 64 |
| | $V_H$15 family (all $V_H$ isotypes) | 31-32 + 38-54 | Set 65 |
| | $V_H$16 family (all $V_H$ isotypes) | 33-34 + 38-54 | Set 66 |
| | All expressed L chains | 55-93 + 96-104 + 109-112 | Set 67 |
| | All expressed κL chains | 55-93 + 96-98 | Set 68 |
| | $V_\kappa$1 family | 55-57 + 96-98 | Set 69 |
| | $V_\kappa$2 family | 58-59 + 96-98 | Set 70 |
| | $V_\kappa$3 family | 60-61 + 96-98 | Set 71 |
| | $V_\kappa$4 family | 62-63 + 96-98 | Set 72 |

TABLE 6-continued

Summary

| PCR template | Gene family | Primer SEQ ID Number | Primer Set No. |
|---|---|---|---|
| | V$_\kappa$5 family | 64-65 + 96-98 | Set 73 |
| | V$_\kappa$6 family | 66-67 + 96-98 | Set 74 |
| | V$_\kappa$7 family | 68-69 + 96-98 | Set 75 |
| | V$_\kappa$8 family | 70-71 + 96-98 | Set 76 |
| | V$_\kappa$9 family | 72-73 + 96-98 | Set 77 |
| | V$_\kappa$10 family | 74-75 + 96-98 | Set 78 |
| | V$_\kappa$11 family | 76-77 + 96-98 | Set 79 |
| | V$_\kappa$12 family | 78-79 + 96-98 | Set 80 |
| | V$_\kappa$13 family | 80-81 + 96-98 | Set 81 |
| | V$_\kappa$14 family | 82-83 + 96-98 | Set 82 |
| | V$_\kappa$15 family | 84-85 + 96-98 | Set 83 |
| | V$_\kappa$16 family | 86-87 + 96-98 | Set 84 |
| | V$_\kappa$17 family | 88-89 + 96-98 | Set 85 |
| | V$_\kappa$18 family | 90-91 + 96-98 | Set 86 |
| | V$_\kappa$19 family | 92-93 + 96-98 | Set 87 |
| | All expressed λL chains | 99-104 + 109-112 | Set 88 |
| | V$_\lambda$1 and V$_\lambda$2 genes | 99-100 + 109-112 | Set 89 |
| | V$_\lambda$3 gene | 101-102 + 109-112 | Set 90 |
| | V$_\lambda$4, V$_\lambda$5, V$_\lambda$6, V$_\lambda$7 and V$_\lambda$8 genes | 103-104 + 109-112 | Set 91 |

| Sequence | SEQ ID |
|---|---|
| agRtYcagctgcaRcagtct | SEQ ID NO: 1 |
| aggtccaactgcagcagcc | SEQ ID NO: 2 |
| gaRgatRtcctgYaaggcttc | SEQ ID NO: 3 |
| aRgBtgtcctgcaagRcttc | SEQ ID NO: 4 |
| tctgcctggtgacWttccca | SEQ ID NO: 5 |
| tgcagctgaagSagtcagga | SEQ ID NO: 6 |
| gtgcagcttcaggagtcag | SEQ ID NO: 7 |
| aaccttctcagWcactgtcc | SEQ ID NO: 8 |
| gaggtgaagcttctcgagtc | SEQ ID NO: 9 |
| ggaggtggcctggtgcag | SEQ ID NO: 10 |
| gaagtgaagctggtggagtc | SEQ ID NO: 11 |
| agcctggagggtccctgaa | SEQ ID NO: 12 |
| atgKacttgggactgaRctgt | SEQ ID NO: 13 |
| gaggagtctggaggaggctt | SEQ ID NO: 14 |
| cagtgtgaggtgaagctggt | SEQ ID NO: 15 |
| tctggaggaggcttggtaca | SEQ ID NO: 16 |
| ccaggttactctgaaagagtc | SEQ ID NO: 17 |
| ctgggatattgcagccctcc | SEQ ID NO: 18 |
| tgtggaccttgctattcctga | SEQ ID NO: 19 |
| acagatccagttggtgcagt | SEQ ID NO: 20 |
| tgttggggctgaagtgggttt | SEQ ID NO: 21 |
| aggtgtgcattgtgaggtgc | SEQ ID NO: 22 |
| atggagtgggaactgagctta | SEQ ID NO: 23 |
| gaagtgcagctgttggagac | SEQ ID NO: 24 |
| agcttcaggagtcaggacc | SEQ ID NO: 25 |
| cctggtgaaaccctcacag | SEQ ID NO: 26 |
| caggtgcagcttgtagagac | SEQ ID NO: 27 |
| aggcttggtgaggcctgga | SEQ ID NO: 28 |
| atgcagctgggtcatcttctt | SEQ ID NO: 29 |
| gaggttcagctgcagcagt | SEQ ID NO: 30 |
| gactggatttggatcacKctc | SEQ ID NO: 31 |
| caatcccaggttcacctacaa | SEQ ID NO: 32 |
| tggagtttggacttagttggg | SEQ ID NO: 33 |
| gtgaggtgcagctggtgga | SEQ ID NO: 34 |
| ctYacctgaggagacDgtga | SEQ ID NO: 35 |
| gtggtccctgcgcccag | SEQ ID NO: 36 |
| ggtBccttggccccagta | SEQ ID NO: 37 |
| gatgacttcagtgttgt | SEQ ID NO: 38 |
| cagggatccaKagttc | SEQ ID NO: 39 |
| caggtcacattcatcg | SEQ ID NO: 40 |
| cacagtgctcatgttca | SEQ ID NO: 41 |
| agtggctgacttccaa | SEQ ID NO: 42 |
| catggccaccagattcttatc | SEQ ID NO: 43 |
| agacatttgggaaggactgac | SEQ ID NO: 44 |
| agggaaataRcccttgaccag | SEQ ID NO: 45 |
| agggaagtagcctttgacaag | SEQ ID NO: 46 |
| ggccagtggatagacHgatg | SEQ ID NO: 47 |
| cagggaccaagggatagaca | SEQ ID NO: 48 |
| gaatcaggcagccgattatcac | SEQ ID NO: 49 |
| tgggagtgtcagtgggtaga | SEQ ID NO: 50 |

| | |
|---|---|
| tcatggaagcagtgcctttac | SEQ ID NO: 51 |
| tagagctgagggttcctgata | SEQ ID NO: 52 |
| tctgagaggaggaacatgtc | SEQ ID NO: 53 |
| tcacctgcaagacagatagtg | SEQ ID NO: 54 |
| tgatgacccaRactccact | SEQ ID NO: 55 |
| cctgtcagtcttggagatca | SEQ ID NO: 56 |
| tttgtcggttaccattggacaa | SEQ ID NO: 57 |
| gcttgtgctctggatccc | SEQ ID NO: 58 |
| SRgatattgtgatgacgcagg | SEQ ID NO: 59 |
| ctgctgctctgggttcc | SEQ ID NO: 60 |
| attgtgctgacccaatctcc | SEQ ID NO: 61 |
| cagcttcctgctaatcagtg | SEQ ID NO: 62 |
| aWtgtKctcacccagtctcc | SEQ ID NO: 63 |
| ctcagatccttggacttHtg | SEQ ID NO: 64 |
| gtctccagccaccctgtc | SEQ ID NO: 65 |
| tggagtcacagacYcagg | SEQ ID NO: 66 |
| tgatgacccagtctcMcaaat | SEQ ID NO: 67 |
| tggagtttcagacccagg | SEQ ID NO: 68 |
| gcctgtgcagacattgtgat | SEQ ID NO: 69 |
| ctgctMtgggtatctggt | SEQ ID NO: 70 |
| cctgtggggacattgtgatg | SEQ ID NO: 71 |
| cWtcttgttgctctggtttc | SEQ ID NO: 72 |
| acatccRgatgacYcagtct | SEQ ID NO: 73 |
| gatgtcctctgctcagttc | SEQ ID NO: 74 |
| ccagatgtgatatccagatg | SEQ ID NO: 75 |
| cctgctgagttccttggg | SEQ ID NO: 76 |
| gccagatgtgatgtYcaaatg | SEQ ID NO: 77 |
| ctgctgctgtggcttaca | SEQ ID NO: 78 |
| atccagatgactcagtctcc | SEQ ID NO: 79 |
| ccttctcaacttctgctct | SEQ ID NO: 80 |
| cctgatatgtgacatccRVat | SEQ ID NO: 81 |
| agggcccYtgctcagttt | SEQ ID NO: 82 |
| Magatgacccagtctccatc | SEQ ID NO: 83 |
| atgagggtccttgctgag | SEQ ID NO: 84 |
| tgagatgtgacatccagatga | SEQ ID NO: 85 |
| gaggttccaggttcaggt | SEQ ID NO: 86 |
| ccagtgtgatgtccagataac | SEQ ID NO: 87 |
| ccatgaccatgYtctcact | SEQ ID NO: 88 |
| acaactgtgacccagtctcc | SEQ ID NO: 89 |
| atggaaactccagcttcattt | SEQ ID NO: 90 |
| acacaggctccagcttctct | SEQ ID NO: 91 |
| atgagaccgtctattcagtt | SEQ ID NO: 92 |
| gtgctcagtgtgacatccag | SEQ ID NO: 93 |
| tStacttacgttttBatttcca | SEQ ID NO: 94 |
| tttBatttccagcttggtScc | SEQ ID NO: 95 |
| tcaagaagcacacgac | SEQ ID NO: 96 |
| gcacctccagatgttaactg | SEQ ID NO: 97 |
| gatggtgggaagatggatac | SEQ ID NO: 98 |
| gcctggaYttcacttatactc | SEQ ID NO: 99 |
| tcccaggctgttgtgactc | SEQ ID NO: 100 |
| tggcctggactcctctctt | SEQ ID NO: 101 |
| caacttgtgctcactcagtc | SEQ ID NO: 102 |
| actcagccaagctctgtg | SEQ ID NO: 103 |
| ctctaggaagcacagtcaaac | SEQ ID NO: 104 |
| gYcactYacctaggacag | SEQ ID NO: 105 |
| aaactacttacctaggacag | SEQ ID NO: 106 |
| taggacagtcagtttggttcc | SEQ ID NO: 107 |
| aggacagtgaccttggttcc | SEQ ID NO: 108 |
| acaccagtgtggcYtt | SEQ ID NO: 109 |
| agctcctcagRggaaggtg | SEQ ID NO: 110 |
| gaaacacggtgagWgtggg | SEQ ID NO: 111 |
| gaaacagggtgactgatgg | SEQ ID NO: 112 |

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

The invention claimed is:

1. A set of oligonucleotides for assaying rearrangement of immunoglobulin genes for identifying clonality of cells, cancer cells, hypermutation in immunoglobulin gene, antibody isotype producing cell and/or assaying B cell repertoire in a sample, wherein the set comprises:
   a. 5' oligonucleotides as set forth in SEQ ID NO: 1-34, SEQ ID NO: 55-93 and SEQ ID NO: 99-104; and
   b. 3' oligonucleotides as set forth in SEQ ID NO: 35-37, SEQ ID NO: 94-95 and SEQ ID NO: 105-108; or 3' oligonucleotides as set forth in SEQ ID NO: 38-54, SEQ ID NO: 96-98 and SEQ ID NO: 109-112.

2. A process of assaying rearrangement of immunoglobulin genes for identifying clonality of cells, cancer cells, hypermutation in immunoglobulin gene, antibody isotype producing cell and/or assaying B cell repertoire in a sample, wherein said process comprises:
   a. providing a sample;
   b. providing 5' oligonucleotides as set forth in SEQ ID NO: 1-34, SEQ ID NO: 55-93 and SEQ ID NO: 99-104;
   c. providing 3' oligonucleotides as set forth in SEQ ID NO: 35-37, SEQ ID NO: 94-95 and SEQ ID NO: 105-108; or 3' oligonucleotides as set forth in SEQ ID NO: 38-54, SEQ ID NO: 96-98 and SEQ ID NO: 109-112;
   d. performing a polymerase chain reaction; and
   e. detecting presence of an amplified product.

3. A process of assaying rearrangement of immunoglobulin genes for identifying clonality of cells, cancer cells, hypermutation in immunoglobulin gene, antibody isotype producing cell and/or assaying B cell repertoire in a sample; said process comprising
   a. providing a sample;
   b. providing a first set of oligonucleotides as set forth in SEQ ID NO: 1, SEQ ID NO: 2, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 55, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 99, SEQ ID NO: 101, SEQ ID NO: 103, SEQ ID NO: 105 and SEQ ID NO: 106;

c. performing a first round of polymerase chain reaction to obtain first product;

d. performing second round of polymerase chain reaction using said first product and oligonucleotides as set forth in SEQ ID NO: 3, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 37, SEQ ID NO: 56, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 100, SEQ ID NO: 102, SEQ ID NO: 104, SEQ ID NO: 107 and SEQ ID NO: 108; and e. detecting presence of an amplified product;

or said process comprising:

a. providing a sample;

b. performing reverse transcription reaction using oligonucleotides as set forth in SEQ ID NO: 38, SEQ ID NO: 39, SEQ ID NO: 40, SEQ ID NO: 41, SEQ ID NO: 42, SEQ ID NO: 96 and SEQ ID NO: 109;

c. providing a first set of oligonucleotides as set forth in SEQ ID NO: 1, SEQ ID NO: 2, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 43, SEQ ID NO: 45, SEQ ID NO: 46, SEQ ID NO: 49, SEQ ID NO: 51, SEQ ID NO: 53, SEQ ID NO: 55, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 97, SEQ ID NO: 99, SEQ ID NO: 101, SEQ ID NO: 103, and SEQ ID NO: 110;

d. performing a first round of polymerase chain reaction using cDNA to obtain first product;

e. performing second round of polymerase chain reaction using said first product and oligonucleotides as set forth in SEQ ID NO: 3, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 44, SEQ ID NO: 47, SEQ ID NO: 48, SEQ ID NO: 50, SEQ ID NO: 52, SEQ ID NO: 54, SEQ ID NO: 56, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 98, SEQ ID NO: 100, SEQ ID NO: 102, SEQ ID NO: 104, SEQ ID NO: 111 and SEQ ID NO: 112; and f. detecting presence of an amplified product.

4. The process of claim 2 or 3, wherein said cancer is B cell lymphoma.

5. The process of claim 2 or 3, wherein said cell is a hybridoma cell and/or a B cell.

6. A process for constructing a library of polynucleotides encoding immunoglobulin genes, said process comprising:

a. amplifying immunoglobulin genes using a set of oligonucleotides comprising 5' oligonucleotides as set forth in SEQ ID NO: 1-34, SEQ ID NO: 55-93 and SEQ ID NO: 99-104 and 3' oligonucleotides as set forth in SEQ ID NO: 35-37, SEQ ID NO: 94-95 and SEQ ID NO: 105-108; or 5' oligonucleotides as set forth in SEQ ID NO: 1-34, SEQ ID NO: 55-93 and SEQ ID NO: 99-104 and 3' oligonucleotides as set forth in SEQ ID NO: 38-54, SEQ ID NO: 96-98 and SEQ ID NO: 109-112 to obtain amplified product;

b. cloning said amplified product in an expression vector to obtain a recombinant expression vector; and c. transforming said recombinant expression vector in a host cell.

7. The process of claim 6, wherein the vector is a prokaryotic expression vector and the host cell is *E. coli*.

8. A kit for assaying rearrangement of immunoglobulin genes for identifying clonality of cells, cancer cells, hypermutation in immunoglobulin gene, antibody isotype producing cell and/or assaying B cell repertoire in a sample, wherein said kit comprises a set of oligonucleotides comprising 5' oligonucleotides as set forth in SEQ ID NO: 1-34, SEQ ID NO: 55-93 and SEQ ID NO: 99-104 and 3' oligonucleotides as set forth in SEQ ID NO: 35-37, SEQ ID NO: 94-95 and SEQ ID NO: 105-108; or 5' oligonucleotides as set forth in SEQ ID NO: 1-34, SEQ ID NO: 55-93 and SEQ ID NO: 99-104 and 3' oligonucleotides as set forth in SEQ ID NO: 38-54, SEQ ID NO: 96-98 and SEQ ID NO: 109-112.

* * * * *